(12) United States Patent
Michaud et al.

(10) Patent No.: US 10,433,141 B2
(45) Date of Patent: Oct. 1, 2019

(54) COMMUNICATION SYSTEM IN A MINE, A NODE, AND METHOD

(71) Applicant: STRATA PRODUCTS WORLDWIDE, LLC, Sandy Springs, GA (US)

(72) Inventors: Tom Michaud, Norcross, GA (US); Michael Berube, Marietta, GA (US); Brian Dunkin, Boulder, CO (US); David W. Hakins, Aldie, VA (US); Michael W. Bertosh, Bethel Park, PA (US); Cody T. Lawler, Upper St. Clair, PA (US); Richard Hurst, Princeton, IN (US)

(73) Assignee: Strata Products Worldwide, LLC, Sandy Springs, GA (US)

( * ) Notice: Subject to any disclaimer, the term of this patent is extended or adjusted under 35 U.S.C. 154(b) by 513 days.

(21) Appl. No.: 14/507,225

(22) Filed: Oct. 6, 2014

(65) Prior Publication Data

US 2015/0163652 A1   Jun. 11, 2015

Related U.S. Application Data

(63) Continuation-in-part of application No. 14/325,028, filed on Jul. 7, 2014, now Pat. No. 9,712,949, which is a continuation-in-part of application No. 14/290,755, filed on May 29, 2014, now Pat. No. 9,992,610.

(60) Provisional application No. 61/887,768, filed on Oct. 7, 2013, provisional application No. 61/847,846, filed on Jul. 18, 2013, provisional application No. 61/832,259, filed on Jun. 7, 2013.

(51) Int. Cl.
| | |
|---|---|
| *G01N 33/00* | (2006.01) |
| *H04W 4/90* | (2018.01) |
| *H04W 4/38* | (2018.01) |
| *H04W 76/12* | (2018.01) |

(52) U.S. Cl.
CPC .......... *H04W 4/90* (2018.02); *G01N 33/0004* (2013.01); *H04W 4/38* (2018.02); *H04W 76/12* (2018.02)

(58) Field of Classification Search
None
See application file for complete search history.

(56) References Cited

U.S. PATENT DOCUMENTS

| | | | |
|---|---|---|---|
| 2008/0137589 A1* | 6/2008 | Barrett | H04M 3/42348 370/327 |
| 2011/0037599 A1* | 2/2011 | Johnson, Jr. | H04W 4/043 340/632 |
| 2011/0133927 A1* | 6/2011 | Humphrey | A62B 9/006 340/539.11 |

* cited by examiner

*Primary Examiner* — Robert M Morlan
*Assistant Examiner* — Pamit Kaur
(74) *Attorney, Agent, or Firm* — Ansel M. Schwartz

(57) ABSTRACT

A communication system in a mine having a data network, a wireless network and a plurality of nodes. A communication node of a data network and a wireless network in a mine. A method for communicating in a mine.

10 Claims, 40 Drawing Sheets

THEORY OF OPERATION

OUTPUT CONFIGURATION

INPUT CONFIGURATION

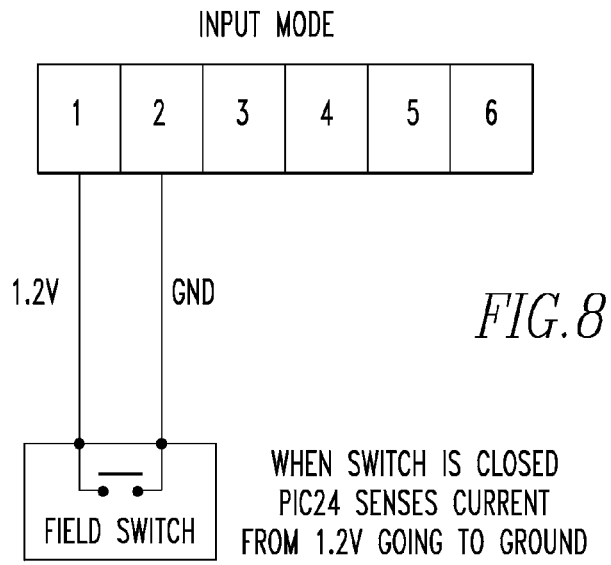

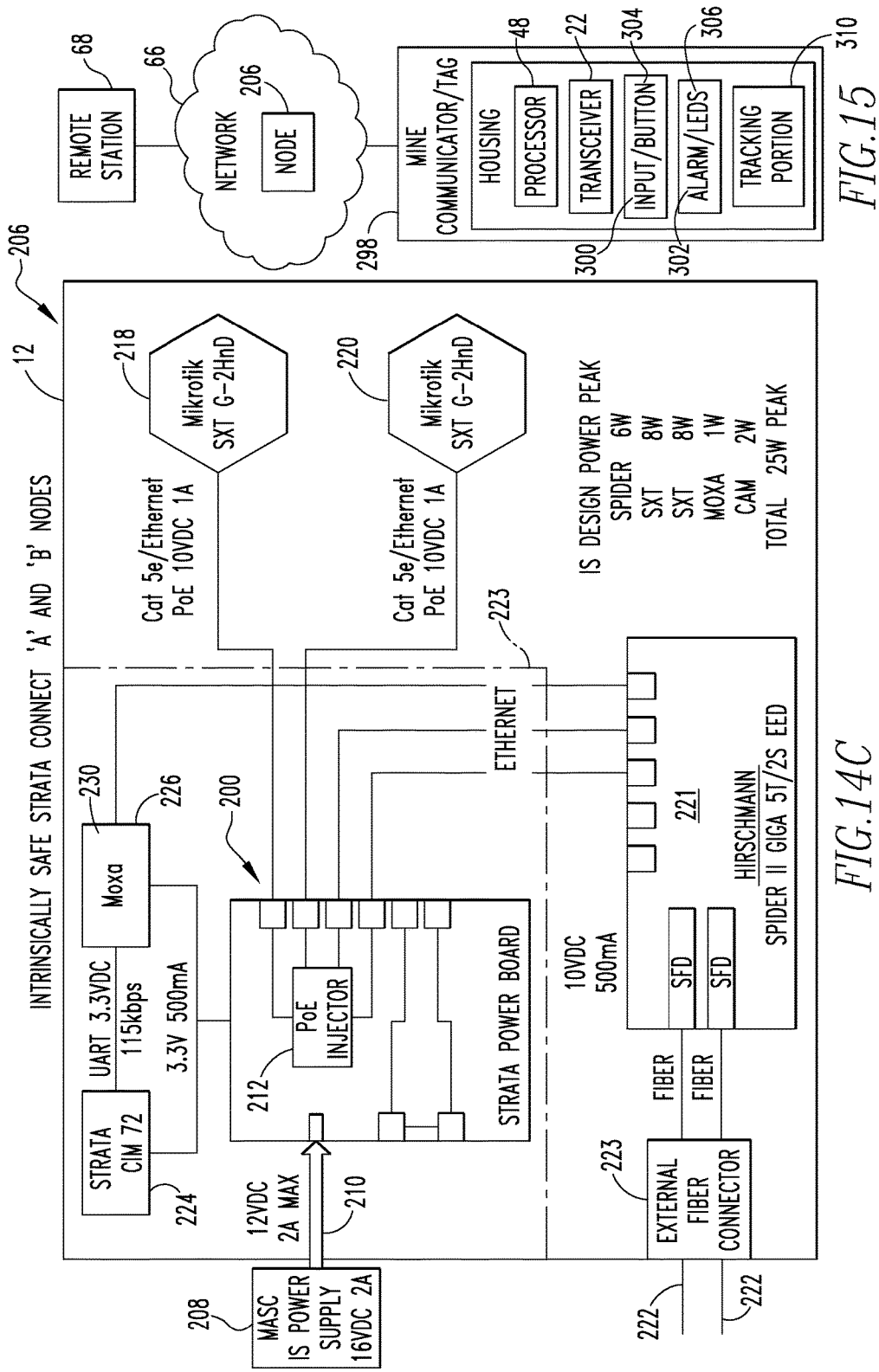

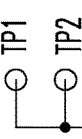
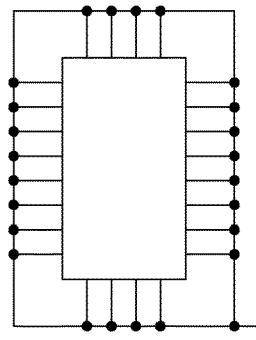
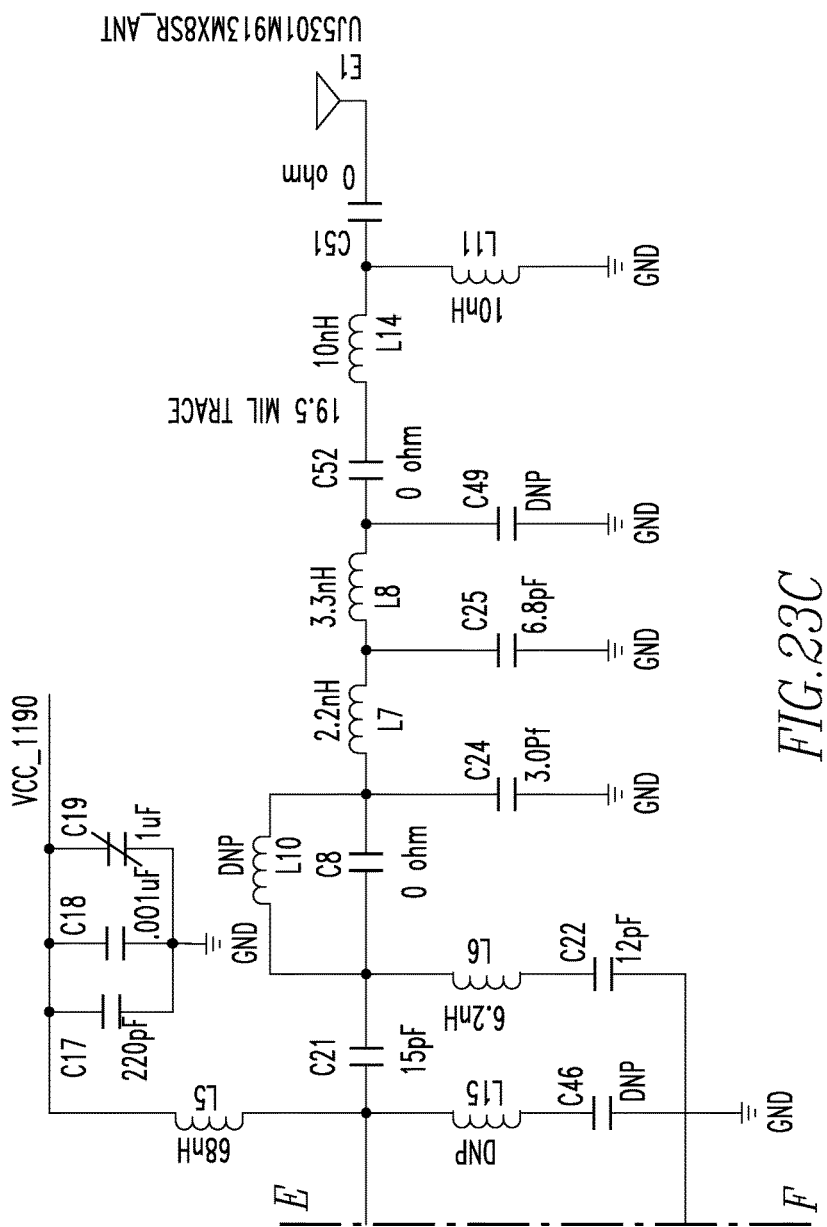
FIG. 23C
FIG. 23D
FIG. 23E

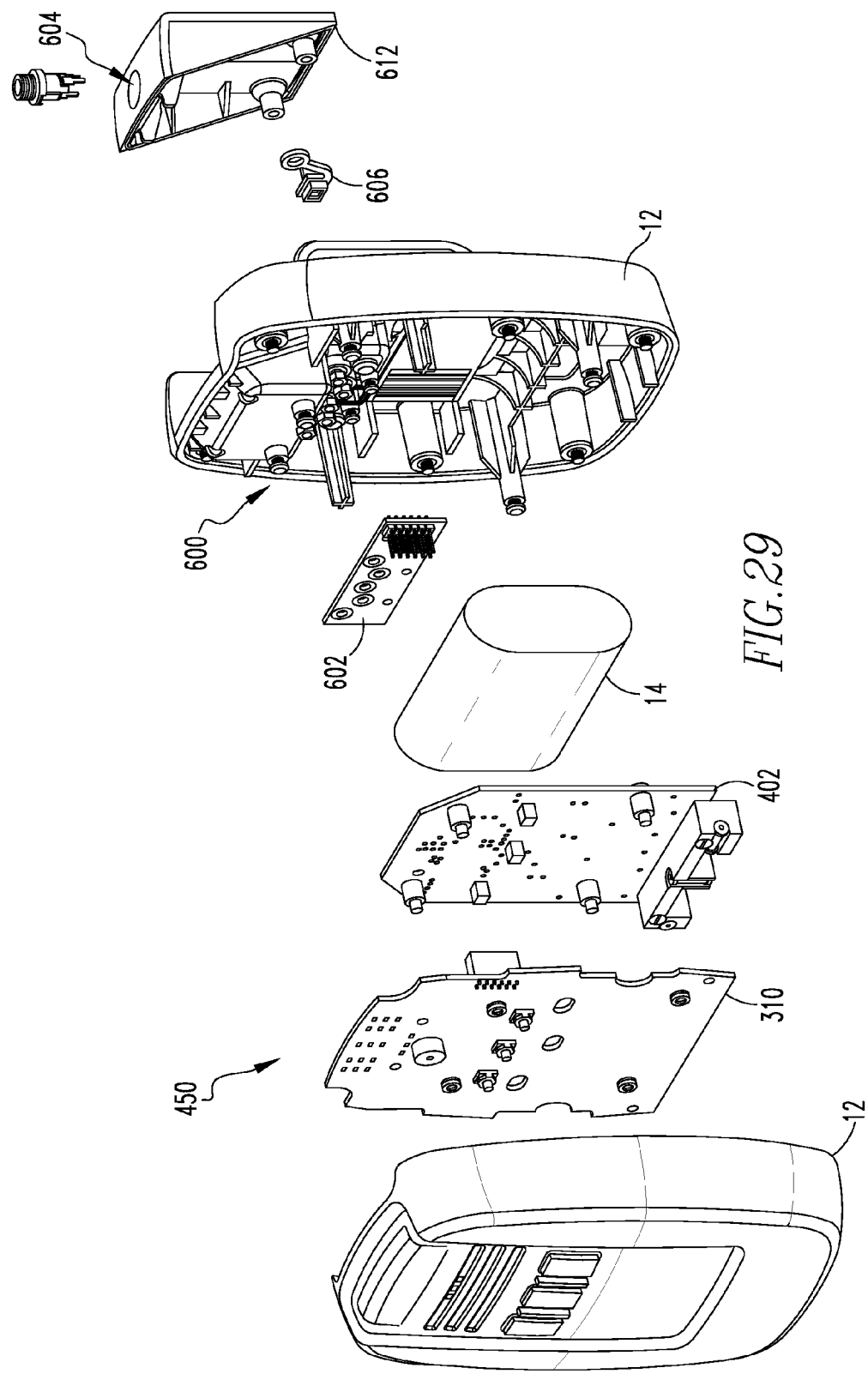

COMMUNICATION SYSTEM IN A MINE, A NODE, AND METHOD

CROSS-REFERENCE TO RELATED APPLICATIONS

This is a nonprovisional of U.S. provisional application Ser. No. 61/887,768 filed Oct. 7, 2013; and is a continuation-in-part of U.S. patent application Ser. No. 14/325,028 filed on Jul. 7, 2014, which is a nonprovisional of U.S. provisional application Ser. No. 61/847,846 filed on Jul. 18, 2013; and is a continuation-in-part of U.S. patent application Ser. No. 14/290,755 filed on May 29, 2014, which is a nonprovisional of U.S. provisional application Ser. No. 61/832,259 filed Jun. 7, 2013, all of which are incorporated by reference herein.

FIELD OF THE INVENTION

The present invention is related to monitoring of gas where the value of the gas is transmitted wirelessly. (As used herein, references to the "present invention" or "invention" relate to exemplary embodiments and not necessarily to every embodiment encompassed by the appended claims.) More specifically, the present invention is related to monitoring of gas in an underground environment or an oil or gas rig with an apparatus where the value of the gas is transmitted wirelessly from the apparatus and an alarm is activated at the apparatus when the value of the gas is above a predetermined value, or an input signal from an input of the apparatus is transmitted wirelessly from the apparatus.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Atmospheric Monitoring Systems, herein after referred to as AMS, and their requirements are thoroughly described in The Mine Safety Health Administration's 30 CFR § 75.351. http://www.msha.gov/30CFR/75.351.htm Historically, AMS consisted of gas monitors connected over a hardwired network all communicating to a central area as described in the above requirement in section (b)(1). As the mine expanded and additional monitors were needed, lengths of cable were added to facilitate communications and power to new monitoring locations. As technology progressed, wireless and battery powered solutions became available. Extensive lengths of cable providing data and power were no longer needed. Mines now have the option of running a hardwired system or a hybrid of both hardwired with wireless. This becomes especially effective when the mine monitoring requirement consists of both permanent and temporary monitoring needs. Areas along the beltways are typically unchanging and are best suited for hardwired monitoring where developing areas of the mine are better suited for a wireless/battery powered solution. Aside from the existing hardwired network, a wireless communication network is still needed to transmit data from the wireless monitors to the designated central area. This could be served with a device that acts as an access point for the wireless monitor data to enter the existing hardwired network or an entirely separate true wireless network such as Strata Products Worldwide, LLC's CommTrac system.

As taken from section (c)(2) of the above requirement, an AMS must have the ability to "Automatically provide visual and audible signals at the designated surface location when the carbon monoxide concentration or methane concentration at any sensor reaches the alert level as specified in § 75.351(i). These signals must be of sufficient magnitude to be seen or heard by the AMS operator."

The detail of importance in this section is the mention of "methane". Traditional AMS hardwired systems offer methane monitoring but only in the 0-5% by volume range using catalytic bead technology. Methane concentrations above 5% will cause catalytic technology to be permanently damaged. In the event of a disaster and mine ventilation is lost, methane levels can easily exceed 5% concentration. Existing technology cannot provide atmospheric information that is critical during rescue efforts. No wireless or hardwired option exists to fulfill this need. Furthermore, the available wireless gas monitoring devices only offer carbon monoxide as a detectable gas and only in the 100 PPM maximum range.

As taken from section (c)(4) of the above requirement, an AMS must have the ability to "Automatically provide visual and audible signals at all affected working sections and at all affected areas where mechanized mining equipment is being installed or removed when the carbon monoxide, smoke, or methane concentration at any sensor reaches the alarm level as specified in § 75.351(i). These signals must be of sufficient magnitude to be seen or heard by miners working at these locations. Methane signals must be distinguishable from other signals."

Traditional AMS hardwired systems offer this ability through a hybrid monitor/alarming unit although no wireless options for this requirement exist currently. Mines are often forced to run a separate control network if using a wireless monitoring solution to satisfy the section alarming requirement.

Similar to mines, oil and gas rigs need to monitor the atmosphere for dangerous levels of various gases without the need of cables and wiring cluttering the rig. In places such as oil and gas rigs, there is also the risk of dangerous gases and the need to monitor the atmosphere for these dangerous gases. Typically, gas monitors were connected by cabling and wiring throughout the rig has been used to monitor dangerous gases on a rig. The presence of all of these cables and wires distributed throughout a rig creates the problem of properly organizing and positioning the cables and wires so they do not interfere with the operation of the rig nor can be damaged so that connection is lost with the monitor during operation. If connection is lost with a monitor, then the monitor as well as the entire length of the cable or wire that connects the monitor to a remote station for monitoring must be examined to correct the loss of communication with the monitor. Such cabling and wiring could extend quite a long distance and be located in difficult positions to examine and can become a significant issue to correct.

In addition, in a mine, it is important to be able to track and communicate with a miner in ideally the most unobtrusive way possible. Besides the mine environment being a dangerous place in and of itself, the more equipment a miner carries, the more difficult it is for the miner to perform his functions and move through the mine. What is desired is a simple way to alert a miner of a dangerous or emergency condition, as well as for the miner to inform a remote station of the miner's condition and the miner's location.

To further provide for the safety of a miner, the miner is required to carry a light, such as a cap lamp that the miner wears on his head, as well as is required to be tracked in the mine, and also be protected from contact with machinery so as not to be injured by the machinery by accidentally contacting the machinery during operation. The latter protection is afforded with the use of a proximity device carried by a miner and proximity sensors positioned on machinery which, when determining that a proximity device carried by a miner is within a predetermined location of the proximity sensor, the machine is turned off so the miner is not injured. As the light is already required to be carried by a miner, and the proximity device is commonly carried by a miner, it would be desirable to combine tracking with these functions since they are already present on the miner.

To provide communication to and from the miner to inform the miner of important information or to track the miner or to enable the miner to communicate with the remote station, communication networks are critical throughout the mine. Since the mine is a very difficult environment for communication networks, redundancy, as well as data networks that ideally work best to transmit data, and voice networks that ideally work best to transmit voice bidirectionally, in which also can transmit data, and work in combination are desired.

BRIEF SUMMARY OF THE INVENTION

The present invention pertains to a monitor for gases and a mine. The monitor comprises a housing. The monitor comprises a battery disposed in the housing. The monitor comprises a gas sensor portion powered by the battery and in electrical communication with the battery which detects a first gas and at least a second gas different from the first gas in the mine. The monitor comprises an alarm portion disposed in the housing, powered by the battery and in electrical communication with the battery which emits a visual alert and an audible alert when the gas sensor portion senses that either the first or second gas is above a predetermined threshold. The monitor comprises a wireless communication portion disposed in the housing, powered by the battery and in electrical communication with the battery and the sensor portion, which sends a wireless signal from the housing that the gas sensor portion has sensed of either the first or second gas. The monitor comprises a processor disposed in the housing, powered by the battery and in electrical communication with the wireless communication portion, alarm portion, sensor portion and battery.

The present invention pertains to a method for monitoring gases in a mine. The method comprises the steps of detecting with a gas sensor portion a first gas and at least a second gas different from the first gas in the mine, the gas sensor portion powered by a battery and in electrical communication with the battery, the gas sensor portion and the battery disposed in the housing. There is the step of emitting with an alarm portion powered by the battery, disposed in the housing and in electrical communication with the battery a visual alert and an audible alert when the gas sensor portion senses that either the first or second gas is above a predetermined threshold. There is the step of sending with a wireless communication portion disposed in the housing, powered by the battery and in electrical communication with the battery and the sensor portion a wireless signal from the housing that the gas sensor portion has sensed either the first or second gas.

The present invention pertains to a monitor for gases in a mine. The monitor comprises a housing. The monitor comprises a battery disposed in the housing. The monitor comprises a gas sensor portion powered by the battery and in electrical communication with the battery which detects a first gas and at least a second gas different from the first gas in the mine. The monitor comprises a terminal portion that has two states, an output configuration state in which an output signal is sent from the processor to a first device, and an input configuration state in which an input signal is received from a second device. The monitor comprises a wireless communication portion disposed in the housing, powered by the battery and in electrical communication with the battery and the sensor portion, which sends a wireless signal from the housing that the gas sensor portion has sensed of either the first or second gas. The monitor comprises a processor disposed in the housing, powered by the battery and in electrical communication with the wireless communication portion, alarm portion, sensor portion and battery.

The present invention pertains to a monitor for gases and a mine. The monitor comprises a housing. The monitor comprises a battery disposed in the housing. The monitor comprises a gas sensor portion powered by the battery and in electrical communication with the battery which detects a first gas and at least a second gas different from the first gas in the mine. The monitor comprises a wireless communication portion disposed in the housing, powered by the battery and in electrical communication with the battery and the sensor portion, which sends a wireless signal from the housing that the gas sensor portion has sensed of either the first or second gas. The monitor comprises at least one input for connection to a remote device which provides a status signal regarding the remote device which is transmitted by the wireless communication portion from the detector. The monitor comprises a processor disposed in the housing, powered by the battery and in electrical communication with the wireless communication portion, the input, sensor portion and battery.

The present invention is related to a system for monitoring gases underground. The system comprises a monitor which detects a gas located in a tunnel underground and determines a gas value of the gas. The monitor has an audio alarm and a visual alarm which is activated what the detected gas is above a predetermined value, and a transceiver which transmits the gas value. The system comprises a wireless telecommunications network on which the gas value is transmitted from the apparatus. The system comprises a remote station which receives the gas value from the network.

The present invention pertains to a system for monitoring gases on an oil or gas rig. The system comprises a monitor which detects a gas at the rig and determines a gas value of the gas. The monitor having an audio alarm and a visual alarm, which is activated when the detected gas is above a predetermined value, and a transceiver which transmits the gas value. The system comprises a wireless telecommunications network on which the gas value is transmitted from the monitor. The system comprises a remote station which receives the gas value from the network.

The present invention pertains to a remote station which receives gas values of gas monitors from a wireless network. The remote station comprises a receiver which receives the gas values wirelessly from the network. The remote station comprises a processor in communication with the receiver which receives the gas values from the receiver. The remote station comprises a display in communication with the processor on which the processor displays an alarm indication when the gas value is above a predetermined level.

The present invention pertains to a communication system. The system comprises a data network on which solely data is sent. The system comprises a wireless network on which voice and data is sent bidirectionally. The system comprises a plurality of nodes distributed and apart from each other that form the data network and the wireless network. Each node has a data portion which receives and sends data on the data network, a wireless portion which receives and sends voice signals on the wireless network, and a power supply portion in electrical communication with the data portion and the wireless portion which powers the data portion and the wireless portion.

The present invention pertains to a communication node of a data network and a wireless network. The node comprises a data portion which receives data wirelessly on the data network. The node comprises a wireless portion which receives and sends voice signals on the wireless network. The node comprises a power supply portion in electrical communication with the data portion and the wireless portion which powers the data portion and the wireless portion. The node comprises a data converter in communication with the data portion and the wireless portion which converts the data from the data network into a transmission signal that is transmitted on the wireless network.

The present invention pertains to a method for communicating in a mine. The method comprises the steps of receiving data wirelessly at a data portion or a first node of a plurality of nodes 206 from a data network on which solely data is sent. The plurality of nodes distributed and apart from each other and form the data network and a wireless network. There is the step of converting with a data converter in communication with the data portion the data from the data network into a transmission signal that is transmitted on the wireless network. The wireless network transmitting and receiving voice and data bidirectionally. There is the step of transmitting the transmission signal from the first node on the wireless network with a wireless portion of the first node. There is the step of powering the data portion and the wireless portion with a power supply portion in electrical communication with the data portion and the wireless portion.

The present invention pertains to a miner communicator in a communications network. The communicator comprises a housing. The communicator comprises a processor disposed in the housing. The communicator comprises a transceiver disposed in the housing and in communication with the processor and the network to send to and receive from the network only data but not including text. The communicator comprises an input disposed on the housing and in communication with the processor which provides a trigger signal to the processor. The communicator comprises an alarm in contact with the housing and in communication with the processor that is activated by the processor when an alarm signal is received by the transceiver. The communicator comprises a position portion disposed in the housing and in communication with the processor which determines a location of the communicator and provides a location to the processor, the processor provides the location and an ID of the communicator to the transceiver which transmits the ID and location to the network to a communication node, ideally the closest node, and then to the remote station.

The present invention pertains to a method for communicating with a miner in a mine. The method comprises the steps of sending an alarm signal wirelessly through a wireless communication network to a miner communicator carried by a miner in the mine. The communicator is only able to receive data but not voice. There is the step of receiving the alarm signal by the communicator. There is the step of activating an alarm of the communicator by a processor of the communicator in response to the communicator receiving the alarm signal. There is the step of activating a button of the communicator to cause the transmitter to transmit from the communicator to the network an indicator signal regarding the miner's status, and with the indicator signal is an id of the communicator and position of the communicator the communicator not having a display or a keyboard.

The present invention pertains to a miner apparatus of a wireless network. The apparatus comprises a housing which is carried by the miner. The apparatus comprises a tracking portion disposed in the housing which determines the miner's location and transmits the location wirelessly to the network. The apparatus comprises a battery disposed in the housing and connected to the tracking portion which powers the tracking portion. The apparatus comprises a cap lamp electrically connected to the battery which is powered by the battery to provide light, the cap lamp worn by the miner.

The present invention pertains to a miner apparatus of a wireless network. The apparatus comprises a housing which is carried by the miner. The apparatus comprises a tracking portion disposed in the housing which determines the miner's location and transmits the location wirelessly to the network. The apparatus comprises a battery disposed in the housing and connected to the tracking portion which powers the tracking portion. The apparatus comprises a proximity device electrically connected to the battery and disposed in the housing which is powered by the battery to provide a detectable presence to a proximity detector when the miner gets too close to the proximity detector, the proximity device worn by the miner.

The present invention pertains to a miner apparatus of a wireless network. The apparatus comprises a housing which is carried by the miner. The apparatus comprises a tracking portion disposed in the housing which determines the miner's location and transmits the location wirelessly to the network. The apparatus comprises a battery disposed in the housing and connected to the tracking portion which powers the tracking portion. The apparatus comprises a proximity device electrically connected to the battery and disposed in the housing which is powered by the battery to provide a detectable presence to a proximity detector when the miner gets too close to the proximity detector, the proximity device worn by the miner. The apparatus comprises a cap lamp electrically connected to the battery which is powered by the battery to provide light. The cap lamp is worn by the miner.

The present invention pertains to a method for a miner to move through a mine. The method comprises the steps of powering a light of a cap lamp on the miner's head with a battery in a housing carried by the miner. There is the step of sending location information from the housing so the miner can be tracked as the miner moves through the mine. There is the step of stopping a machine with a proximity sensor connected to the machine, because the proximity sensor has sensed a proximity device in the housing has come within a predetermined distance to the proximity device.

The present invention pertains to a proximity detector attached to a machine. The detector for detecting a miner's presence comprises a generator which produces a magnetic field. The detector comprises a processor. The detector comprises a transceiver for sending a message produced by the processor having information about the generator's health and an ID of a PAD of a miner that has triggered a warning or hazard that has effectively stopped operation of the machine.

BRIEF DESCRIPTION OF THE SEVERAL VIEWS OF THE DRAWING

In the accompanying drawings, the preferred embodiment of the invention and preferred methods of practicing the invention are illustrated in which:

FIG. 8 is a representation of the terminal connectivity regarding input mode of the claimed invention.

FIG. 9 is a representation of the terminal connectivity regarding output mode of the claimed invention.

FIG. 10 is a representation of the terminal.

FIGS. 14B and 14C are block diagrams of a shared power supply of a node.

FIG. 15 is a block diagram of a miner communicator.

FIGS. 22A-22K and 23A-23E are circuit diagrams of the miner communicator of the present invention.

FIG. 29 is an exploded view of the miner apparatus.

DETAILED DESCRIPTION OF THE INVENTION

Figure 1A:
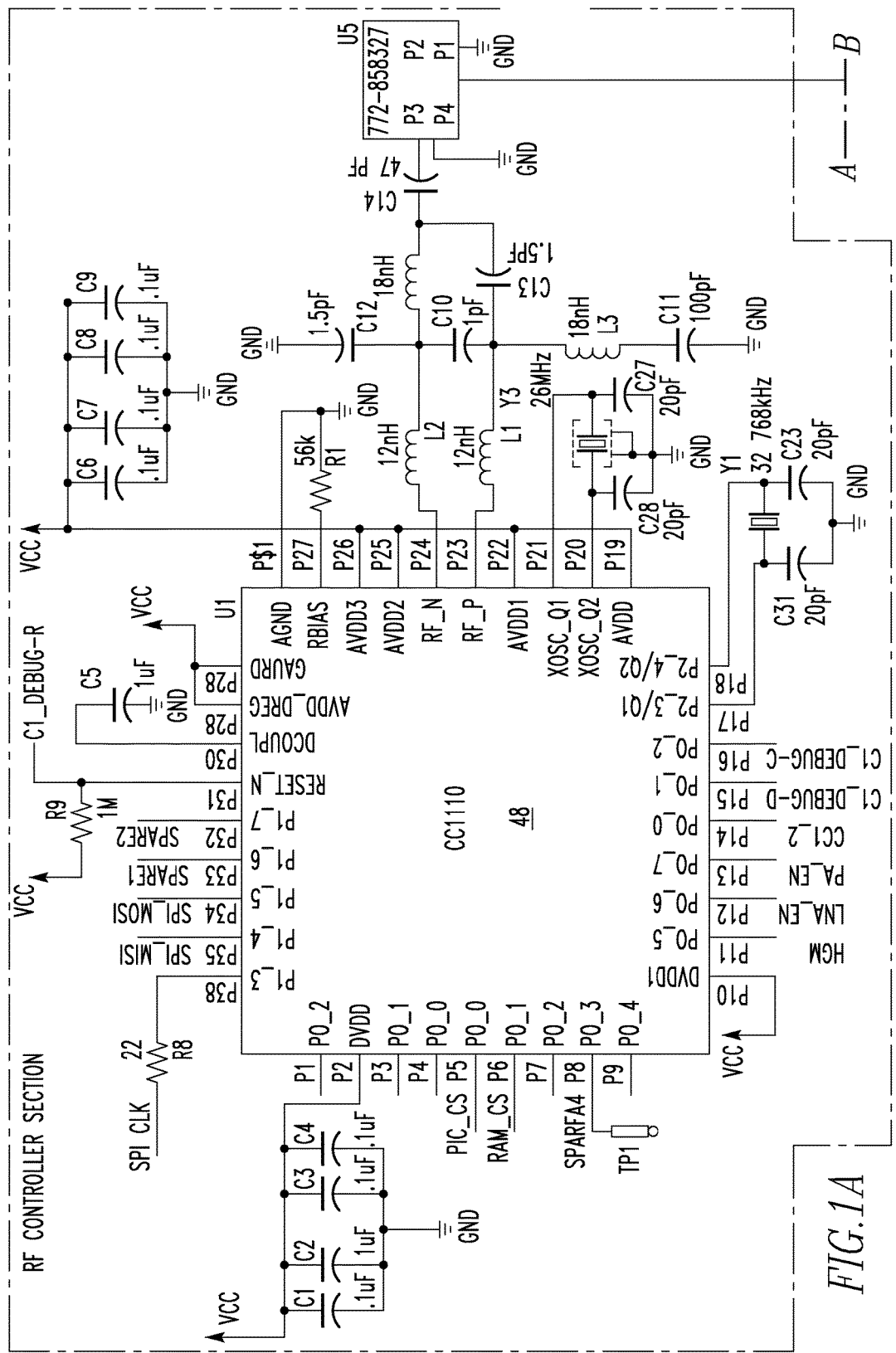
FIGS. 1A, 1AA, 1B and 2A-2E are engineering schematic diagrams of the wireless communications portion, the alarm portion and the battery of the present invention.
Figure 1A:
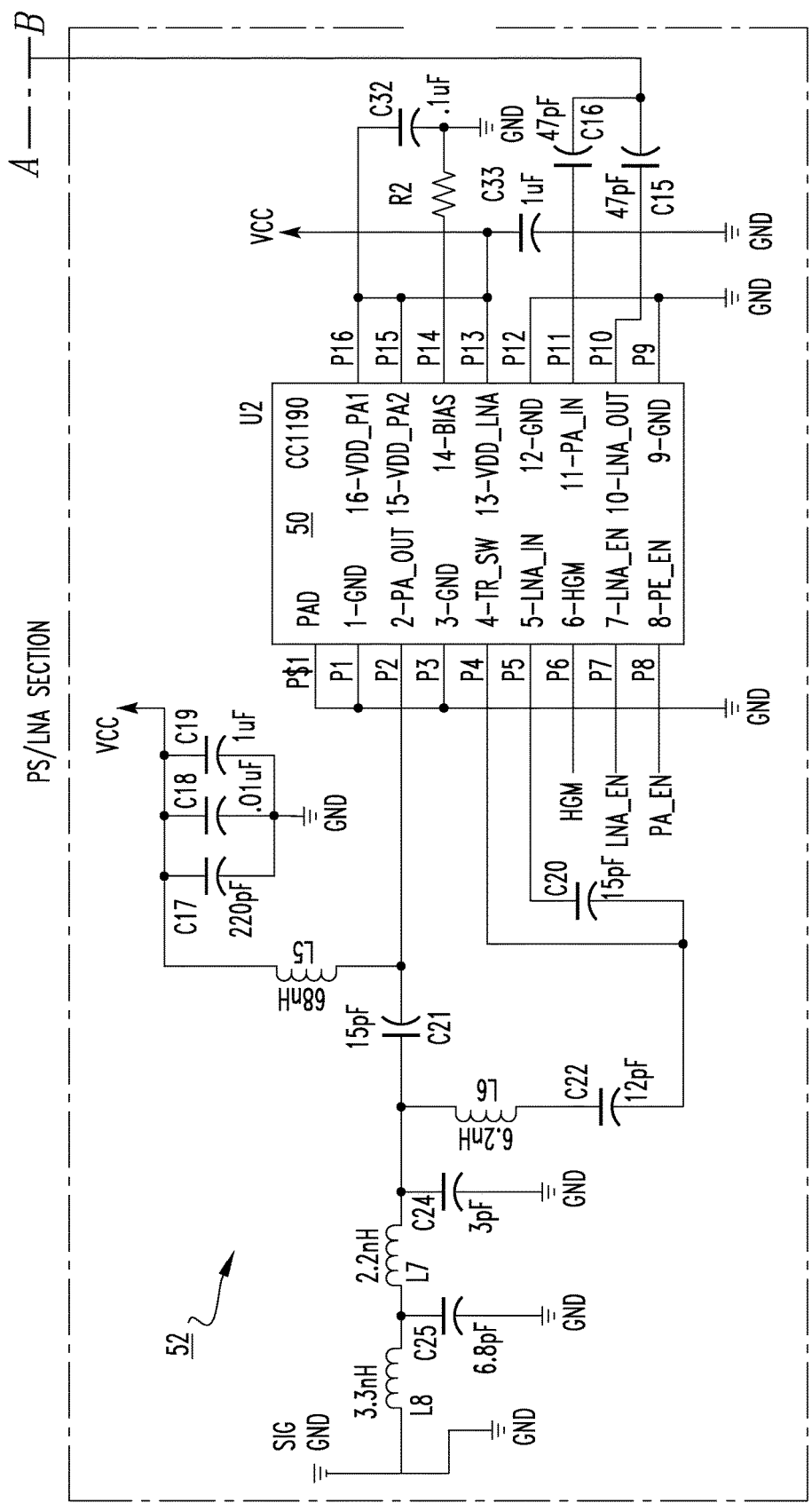

Referring now to the drawings wherein like reference numerals refer to similar or identical parts throughout the several views, and more specifically to FIGS. 1A-5, 11, 12 and 13 thereof, there is shown a monitor 10 for gases in a mine. The monitor 10 comprises a housing 12. The monitor 10 comprises a battery 14 disposed in the housing 12. The monitor 10 comprises a gas sensor portion 16 powered by the battery 14 and in electrical communication with the battery 14 which detects a first gas and at least a second gas different from the first gas in the mine. The monitor 10 comprises an alarm portion 18 disposed in the housing 12, powered by the battery 14 and in electrical communication with the battery 14 which emits a visual alert and an audible alert when the gas sensor portion 16 senses that either the first or second gas is above a predetermined threshold. The monitor 10 comprises a wireless communication portion 20 disposed in the housing 12, powered by the battery 14 and in electrical communication with the battery 14 and the sensor portion, which sends a wireless signal from the housing 12 that the gas sensor portion 16 has sensed of either the first or second gas. The monitor 10 comprises a processor 22 disposed in the housing 12, powered by the battery 14 and in electrical communication with the wireless communication portion 20, alarm portion 18, sensor portion and battery 14.

Figure 11:
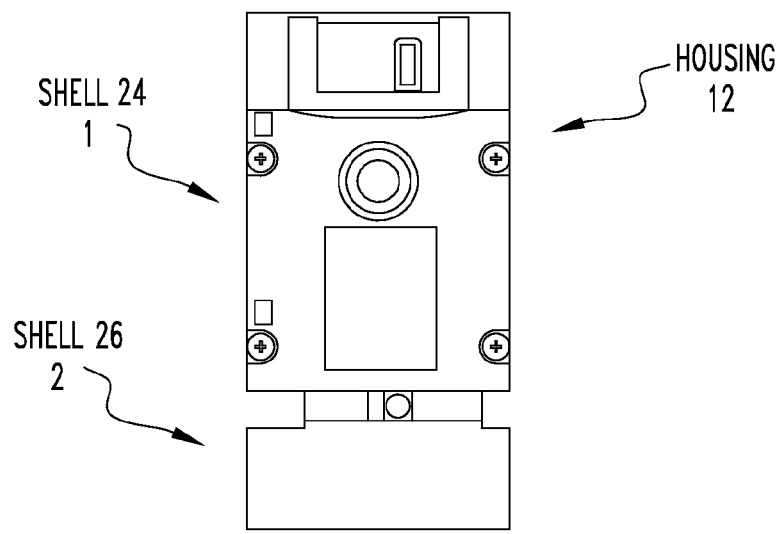
FIG. 11 shows the apparatus having a housing with a first shell and a second shell.
Figure 12:
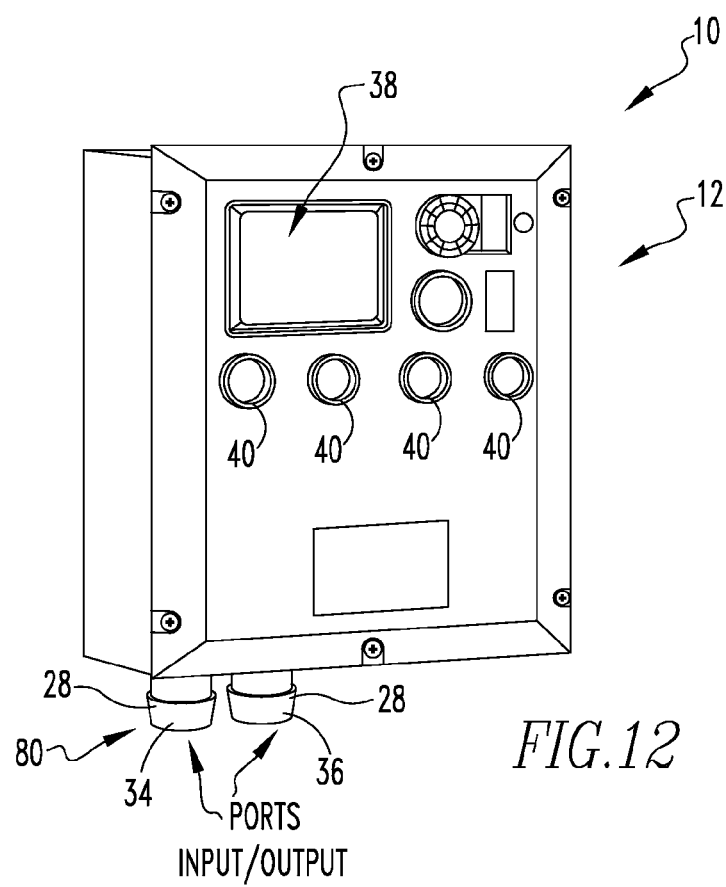
FIG. 12 shows the apparatus having a first port and a second port for inputs or outputs.

The housing 12 may be one single shell or a combination of shells that are effectively engaged together, as shown in FIGS. 11 and 12. For instance, audio and visual (AV) alarms of the alarm portion 18 may be in a separate or second shell 26 from the processor 22 and the wireless communication portion 20 which is in a first shell 24 separate from the second shell 26, with the AV alarms electrically connected by wires which extend through MSHA approved glands 28 and the first and second shells 24, 26 may be held together with screws or rivets. The gas monitoring portion may be in a separate shell from the processor 22 and wireless communication portion 20 and be in electrical communication through wires passing through a gland(s) 28. FIG. 11 shows the apparatus having a housing 12 with a first shell 24 and a second shell 26. The second shell 26 has the AV alarms. FIG. 12 shows the apparatus having a first port 34 and a second port 36 with glands 28 for inputs 54 or outputs 56. FIG. 12 also shows an embodiment of the apparatus with the capability of monitoring and detecting four different gases, for instance here Nitric Oxide, Methane, Oxygen and Carbon Monoxide, as shown in a display 38 of the housing 12. Here, there are four openings 40, one for each gas being sensed, in fluid communication for the respective gas module monitoring and detecting the respective gas.

The gas sensor portion 16 may include a full range by volume between zero and 100% methane sensor 42 and the wireless communication portion 20 transmits wirelessly from the housing 12 a methane value of methane in the mine sensed by the sensor portion. The gas sensor portion 16 may include a carbon monoxide sensor 44 and a H2S sensor 46 and the wireless communication portion 20 transmits wirelessly from the housing 12 a carbon monoxide value of carbon in the mine sensed by the sensor portion and an H2S value of H2S in the mine sensed by the sensor portion. The processor 22 may receive a gas value signal from the gas sensing portion and converts the gas value signal into a converted signal form of the gas value which can be sent wirelessly by the communication portion 20 from the housing 12.

The communication portion 20 may include a transceiver 48 in communication with the processor 22, as shown in FIGS. 1A, 1AA and 2A-2F. The communication portion 20 may include an amplifier 50 with an internal antenna 52 in communication with the transceiver 48, as shown in FIGS. 1A and 1AA. The processor 22 may provide the converted signal of the gas value to the transceiver 48 which then transmits the converted signal form of the gas value wirelessly through the amplifier 50 and the internal antenna 52 from the housing 12. The processor 22 may receive an alarm signal from the gas sensor portion 16 and activates the visual alarm 32 and the audible alarm based on the alarm signal.

Figure 13:
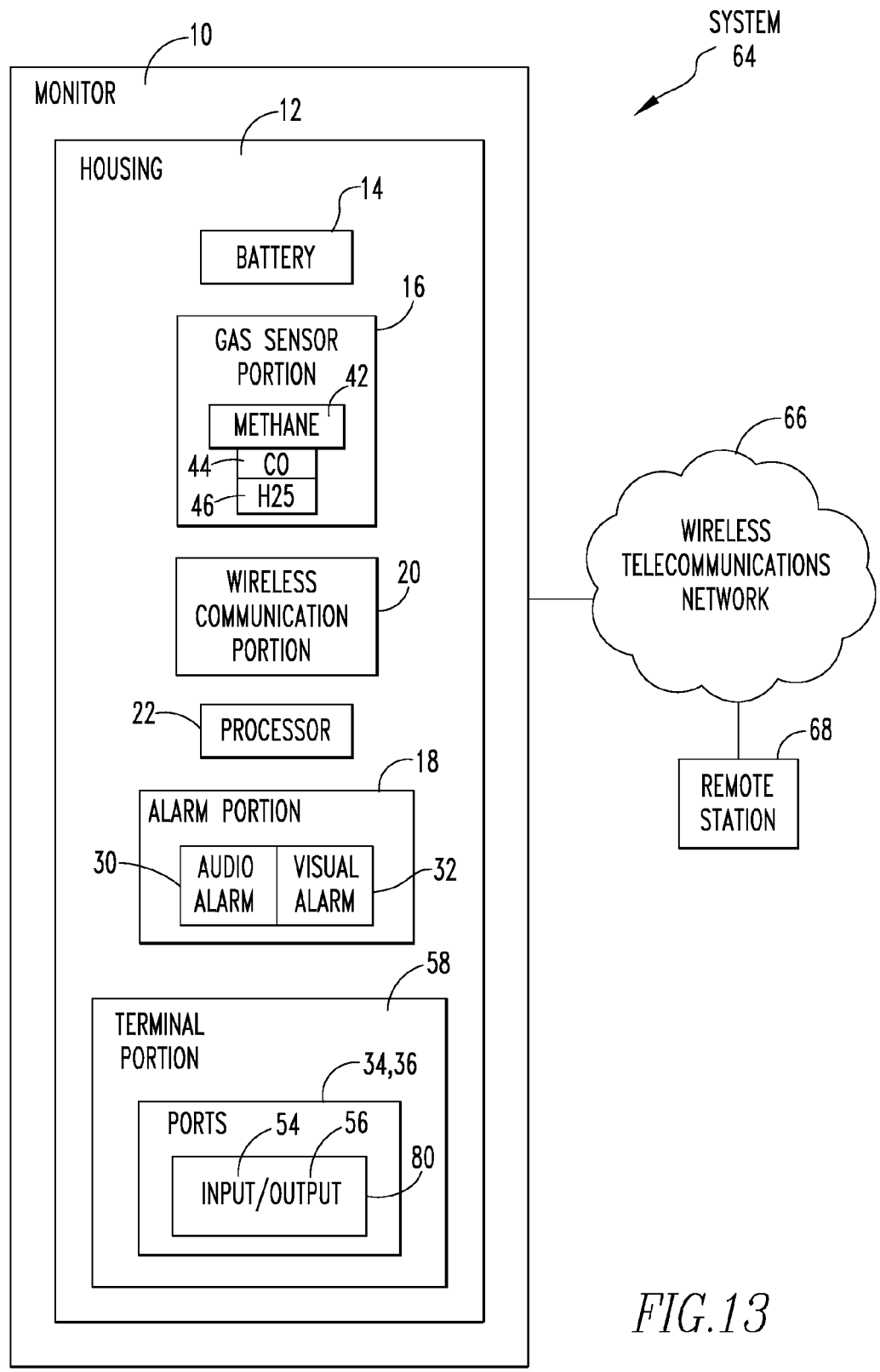
FIG. 13 is a block diagram regarding the system of the present invention.

The present invention pertains to a monitor 10 for gases and a mine, as shown in FIG. 13. The monitor 10 comprises a housing 12. The monitor 10 comprises a battery 14 disposed in the housing 12. The monitor 10 comprises a gas sensor portion 16 powered by the battery 14 and in electrical communication with the battery 14 which detects a first gas and at least a second gas different from the first gas in the mine. The monitor 10 comprises a wireless communication portion 20 disposed in the housing 12, powered by the battery 14 and in electrical communication with the battery 14 and the sensor portion, which sends a wireless signal from the housing 12 that the gas sensor portion 16 has sensed of either the first or second gas. The monitor 10 comprises at least one input 54 for connection to a remote device which provides a status signal regarding the remote device which is transmitted by the wireless communication portion 20 from the detector. The monitor 10 comprises a processor 22 disposed in the housing 12, powered by the battery 14 and in electrical communication with the wireless communication portion 20, the input 54, sensor portion and battery 14.

The present invention pertains to a method for monitoring gases in a mine. The method comprises the steps of detecting with a gas sensor portion 16 a first gas and at least a second gas different from the first gas in the mine, the gas sensor portion 16 powered by a battery 14 and in electrical communication with the battery 14, the gas sensor portion 16 and the battery 14 disposed in the housing 12. There is the step of emitting with an alarm portion 18 powered by the battery 14, disposed in the housing 12 and in electrical communication with the battery 14 a visual alert and an audible alert when the gas sensor portion 16 senses that either the first or second gas is above a predetermined threshold. There is the step of sending with a wireless communication portion 20 disposed in the housing 12, powered by the battery 14 and in electrical communication with the battery 14 and the sensor portion a wireless signal from the housing 12 that the gas sensor portion 16 has sensed either the first or second gas.

Figure 4:
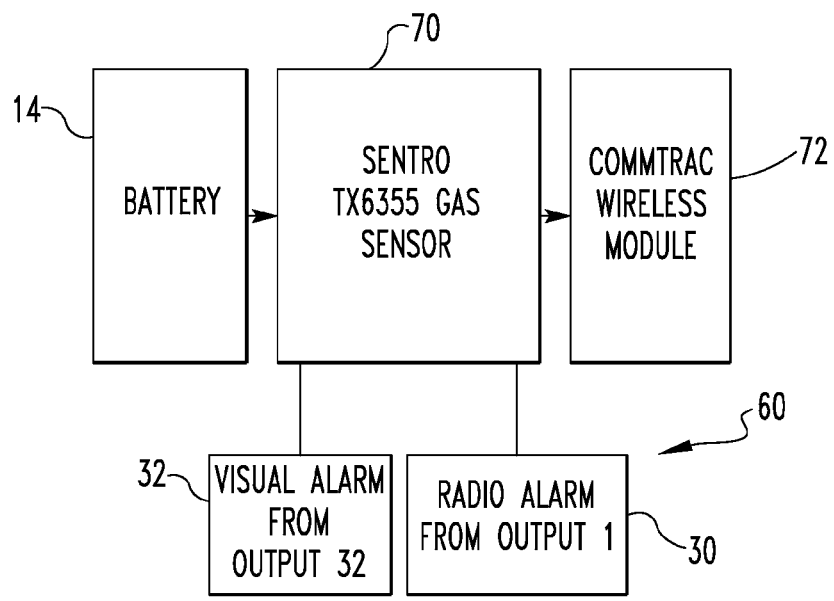
FIG. 4 is a block diagram of the wireless communications portion, the alarm portion and the battery of the present invention.
Figure 7:
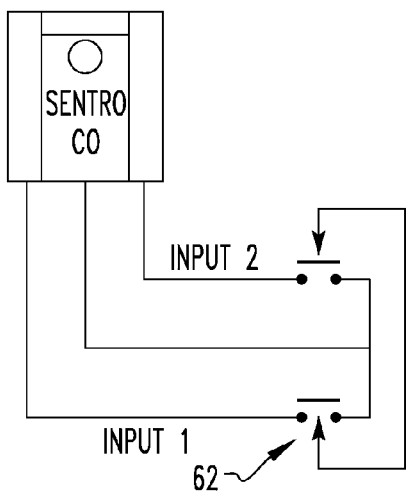
FIG. 7 is a representation of the input configuration of the claimed invention.

The present invention pertains to a monitor 10 for gases in a mine, as shown in FIG. 13. The monitor 10 comprises a housing 12. The monitor 10 comprises a battery 14 disposed in the housing 12. The monitor 10 comprises a gas sensor portion 16 powered by the battery 14 and in electrical communication with the battery 14 which detects a first gas and at least a second gas different from the first gas in the mine. The monitor 10 comprises a terminal portion 58 that has two states, an output configuration state in which an output signal is sent from the processor 22 to a first device 60, such as the audio alarm 30, as shown in FIG. 4, and an input 54 configuration state in which an input 54 signal is received from a second device 62, such as a field switch, as shown in FIG. 7. The monitor 10 comprises a wireless communication portion 20 disposed in the housing 12, powered by the battery 14 and in electrical communication with the battery 14 and the sensor portion, which sends a wireless signal from the housing 12 that the gas sensor portion 16 has sensed of either the first or second gas. The monitor 10 comprises a processor 22 disposed in the housing 12, powered by the battery 14 and in electrical communication with the wireless communication portion 20, alarm portion 18, sensor portion and battery 14.

The present invention is related to a system 64 for monitoring gases underground, as shown in FIG. 13. The system 64 comprises a monitor 10 which detects a gas located in a tunnel underground and determines a gas value of the gas. The monitor 10 has an audio alarm 30 and a visual alarm 32 which is activated what the detected gas is above a predetermined value, and a transmitter which transmits the gas value. The system 64 comprises a wireless telecommunications network 66 on which the gas value is transceiver 48 from the monitor. The system 64 comprises a remote station 68 which receives the gas value from the network 66. The transceiver may receive a signal from the network to change a set point for an alarm condition for the gas to be determined by the monitor.

Figure 3:
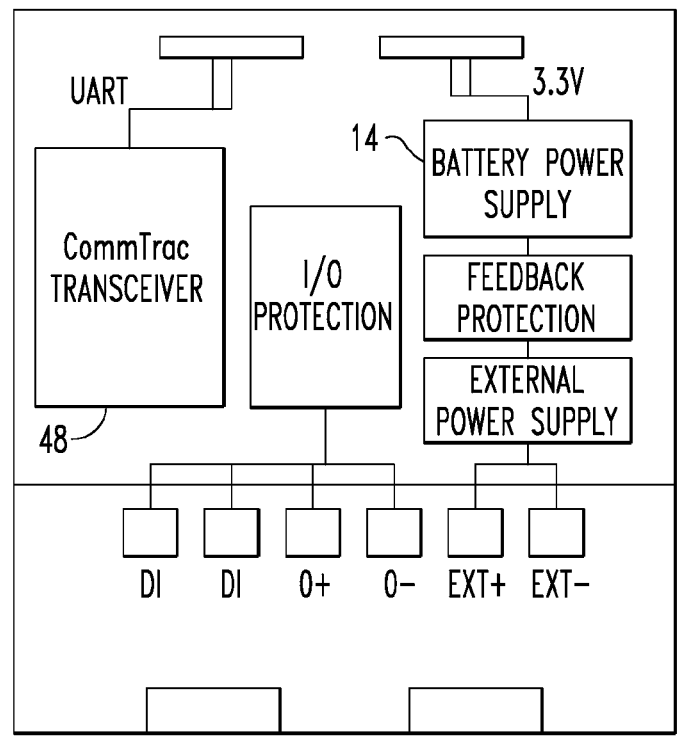
FIG. 3 is a block diagram of the present invention.

In the operation of the invention, and with reference to FIG. 13, the system 64 is a battery 14 powered CommTrac enabled gas monitor 10 to fulfill the MSHA requirements identified above and offer a truly unique solution. To meet the requirement of section (c)(2), a visual and audible alarm has been integrated into a Trolex Sentro gas detector 70 equipped with a battery 14 pack and CommTrac Interface module 72 (CIM), as shown in FIGS. 3 and 4. The alert points will allow for a completely wireless gas monitor 10 that has the ability to alert personnel in the working zones in accordance with section (c)(2). The gas concentration alert and alarm points as mentioned in sections (i)(2) and (i)(3) will trigger the integrated monitor 10 audible and visual alarms via two unique output options. The first output 74 will trigger the visual alarm 32 when an alert level is reached. Different color visual alarms 32 will be available for different gases. The second output 76 will trigger the audible alarm when an alarm level is reached. If the monitor 10 is not being configured as a section alarm, the outputs 56 can be used as remote output to control connected devices. Aside from just methane and carbon monoxide, carbon dioxide, hydrogen sulfide, nitrogen dioxide, chlorine, oxygen, nitric oxide, and hydrogen will also be available for detection. Methane will be detectable over the entire volume range using an infrared technology based sensor as opposed to the current catalytic technology. Aside from full range capabilities, infrared technology is not affected by high concentrations. Carbon monoxide will be available in 1000 PPM maximum range. Hydrogen discriminate carbon monoxide detection will also be supported along with nitrogen dioxide filtered carbon monoxide detection capabilities. Open wireless protocols such as 802.11 will also be a supported means of communication aside from the CommTrac mesh infrastructure. Ultimately, the wireless battery 14 powered gas monitor 10 can offer a complete and single system solution to the MSHA AMS requirement. The features outline above are truly unique and the first of their kind. The CommTrac network 66 already exists and is available from Strata Products Worldwide, LLC, Sandy Springs, Ga.

Figure 5:
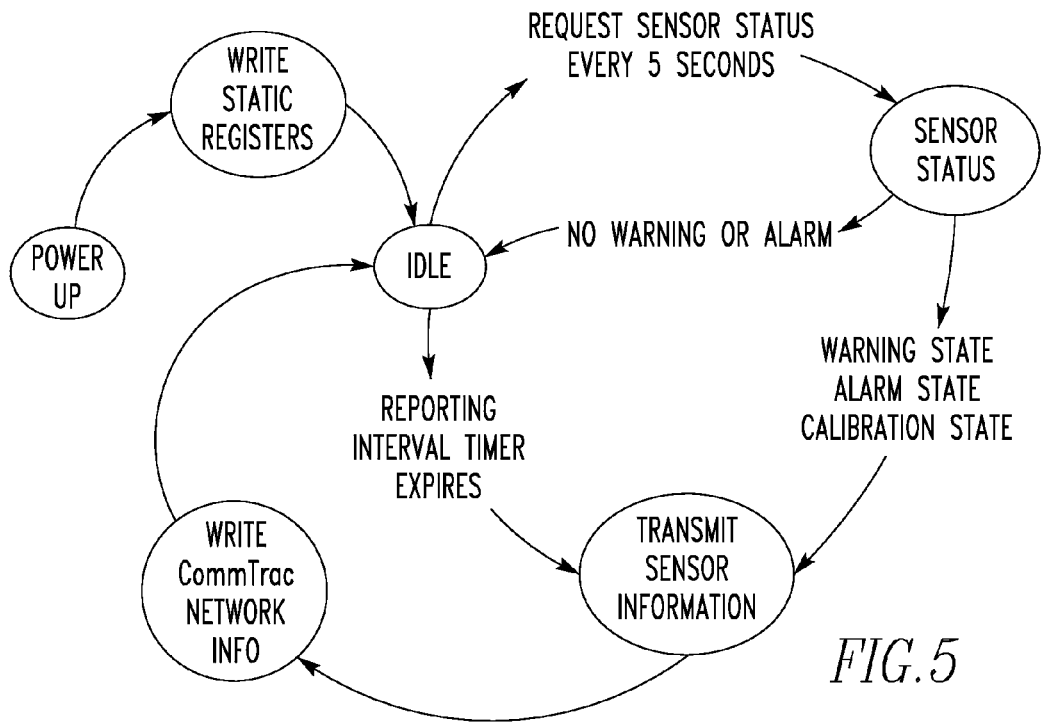
FIG. 5 is an operations diagram of the present invention.

In regard to FIG. 5, there is shown a theory of operation of the present invention. First, the monitor 10 is turned on and powered up. Then, the necessary software and functionality is written into the static registers of the monitor 10 for operation. From that point, stable operation of the monitor 10 proceeds from an idle state. From the idle state, the processor 22 requests of the gas sensor portion 16 a status report every five seconds. The gas sensor portion 16, if there is no warnings or alarms identified, reports hack to the processor 22 that there are no warnings or alarms. If there is a warning state or alarm state or calibration state that occurs, the processor 22 takes the information that it has received from the gas sensor portion 16 and prepares this information to be sent through the transceiver 48 and out the antenna 52 to the CommTrac network 66 and ultimately to the central monitoring station. In addition, if the processor 22 does not receive a response from the gas sensor portion 16 within the interval timer period after the request for sensor status has been issued, then the processor 22 also transmits through the CommTrac network 66 a signal that communication has been lost with the gas sensor portion extending. When the central monitoring station receives the signal that communication has been lost with the gas sensor portion 16, steps are then taken to investigate and review the gas sensor portion 16 to correct the problem that is causing the failure of the gas sensor portion 16 to respond to the processor 22.

In regard to FIG. 3, there is shown a block diagram of the monitor 10. The CommTrac transceiver 48 is in electrical connection over a UART connection to the antenna 52. The CommTrac transceiver 48 is also in communication with the battery 14 power supply through which power from the mine power supply is available. There is feedback protection connected to the external port connectors connected to the mine power supply. The battery 14 power supply is also connected at 3.3 V to the output 56 ports to provide power to them. There are two input 54 ports and two output 56 ports. There is also a video alarm 32 and an audio alarm 30. There is input/output protection connected to the battery 14 power supply, the CommTrac transceiver 48 and the input and output ports.

In the operation of the invention, reference is made to the parts list below which identities the parts by model number and vendor from which they can be obtained. The operation of the parts listed below, as individual components, is well known.

The gas sensor portion 16 itself is an off-the-shelf Trolex TX 6351/2 Sentro 1 universal gas detector 70. It has the ability to monitor several different gases at once. For a given gas value identified by the detector, this value is provided to the processor 22, which is a PIC 24 processor 22. The processor 22 converts the gas value into a packet form which can be transmitted wirelessly. The gas value provided from the detector 70 to the processor 22 is across a standard serial connection. It is received at pin header 6 of the processor 22, as shown in FIGS. 1B and 2A-2E. The detector 70 provides a specific gas value for a given gas being monitored by the detector 70 in response to a request sent by the processor 22 from its pin header 4. The requests for the different gases, occurs one at a time in sequence, and then is continually repeated so that the different gases being monitored by the detector 70 are continually reviewed over time by the processor 22.

The packet produced by the processor 22 for a given gas being monitored, is then sent from PIC 24 to the transceiver 48, CC 1110, as shown in FIG. 1A, where it is received at its pin 34 input 54. From the transceiver 48, the packet signal is then provided to the amplifier 50 CC 1190 which boosts the signal and then transmits it through its antenna 52. The wireless transmitted packet having the value of the gas is then transmitted over the existing CommTrac network 66. The PIC 24, CC 1110, CC 1190 and internal antenna 52 form and define the CIM 72

Signals can also be received by the antenna 52 of the amplifier 50, which modulates the received signal, and provides it to the transceiver 48 where it is outputted through transceiver 48 pin 35 back to the processor 22 that receives it at pin header 6. The signal that is received by the monitor 10 can be a signal to change the set point by the processor 22 for an alarm condition for a given gas being monitored.

In addition to the gas value that is provided by the gas detector 70 to the processor 22, along the same serial connection and same pin attachments, an alarm signal for a given gas is provided to the processor 22 when the monitor 10 gas is above a certain predetermined value. The processor 22 receives the alarm signal and then activates an audio alarm 30 as well as a visual alarm 32. The audio alarm 30 is loud enough to be heard by miners in the vicinity of the monitor 10. The visual alarm 32 is formed by a plurality of LED lights that are illuminated when the alarm occurs. A different sequence of colors, or simply different colors are illuminated for a corresponding type of gas, so for instance methane would have a different set of LED lights or different colors of lights activated then the LED lights activated for carbon dioxide. In addition, if so desired, the audio alarm 30 can be set to have a different tone or frequency corresponding to the type of gas detected if desired. The processor 22 also transmits an alarm signal through the transceiver 48 to the CommTrac network 66.

The processor 22, detector, transceiver 48 and amplifier 50 are all powered by battery 14 through a standard battery 14 selection circuit 74. Also available is an external power interface 76 that can receive wired electricity from the mine external power source.

The wireless communication portion 20 that has been added to the gas detector 70 contains a microcontroller—a CC1110 which is in electrical communication with thee PIC24 microcontroller. The PIC24 is the center of the monitor in that it communicates with the detector's microcontroller to obtain sensor information and also communicates with the CC1110 to send and receive data over the CommTrac network 66.

The software in the PIC24 polls the detector's microcontroller, here the Trolex PIC18, on a continuous basis for sensor information. It packages this sensor information and sends it to the CC1110 to be transmitted over the CommTrac system at configurable intervals. The software also monitors the information from the PIC18 on the Trolex detector for alarms and if any are generated, a message will be sent to the CC1110 for transmission via the CommTrac network 66.

Figure 6:
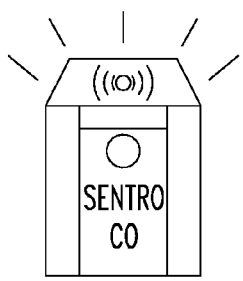
FIG. 6 is a representation of the output configuration of the claimed invention.

The software can also be configured to use the two available I/Os 80, as shown in FIGS. 12 and 13. These I/Os 80 can either be connected to audible and visual alarms 30, 32—in which case, they would be activated if an alarm condition is reported by the detector 70, as shown in FIGS. 6 and 8. Alternatively, these I/Os 80 can be used as inputs which will cause the software to send a message over CommTrac if the circuit on the I/O line is broken, (E.g. a belt stop switch), as shown in FIGS. 7 and 9. In between these activities, the software will put the CC1110 and the PIC24 into sleep mode in order to conserve power.

The CC110 transceiver 48 receives the message from the PIC 24 and places it into the transmit queue. The CC1110 is then listening for a beacon message from one of the CommTrac Communication Nodes (backbone of the network 66). When it hears a beacon message it will select a data slot to transmit the message. During the chosen slot the message is sent and it waits to receive an ack from the Communication Node during the acknowledgement slot. If the ack is properly received the message will be removed from the transmit queue. If it doesn't receive an ack then the message is resent during the next beacon cycle. The CC1190 is typically only used to amplify the transmit and receive signal to allow for greater distances when transmit/receiving.

The AV unit may be mounted beneath a Wireless Sentro Gas detector 70 with the communication portion 20 with hard wiring between the two units, as shown in FIG. 11. The sound and light alarms will be activated by switching the battery 14 supply on and off. This can be controlled by software allowing the option of pulsed light and sound alarms.

The same two outputs of the pic 24 that are used to drive the audible and visual alarms 32 can be configured using software to also be inputs 54. The configuration allows the states of various input devices such as pull cords, emergency stops buttons or fault switches to be transmitted through the CommTrac network 66 to the surface for monitoring. The states of the switches are often unrelated to the gas monitoring data that the sensors are transmitting, but the sensors are typically located in remote areas in the mine where other communication networks do not exist. It is quite attractive to give the mine the option of monitoring a remote switch through a communication network 66 that is available in remote areas. Alternately, if the apparatus is not equipped with an audible or visual alarm 30, 32, the available output 56 can be used to drive a low current consumption device that may also be located remotely in the mine where the CommTrac network 66 is available.

Figure 1B:
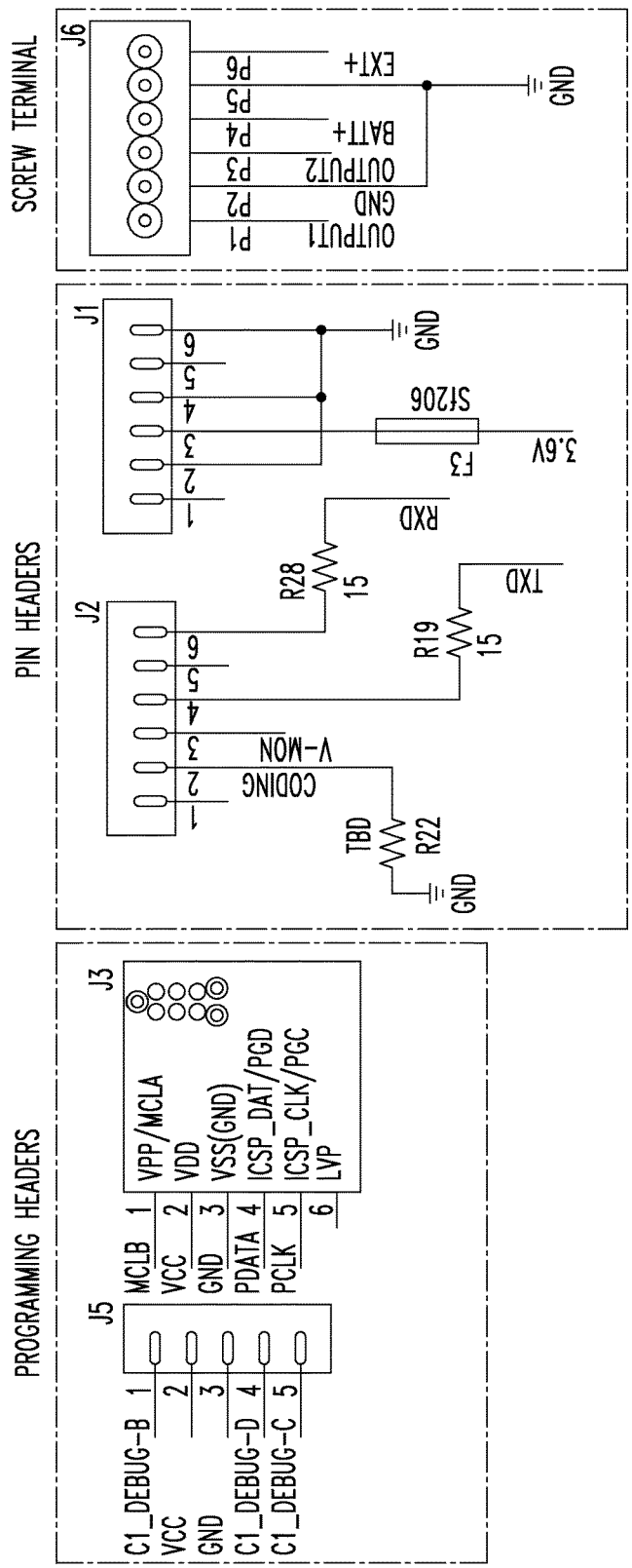
Figure 2A:
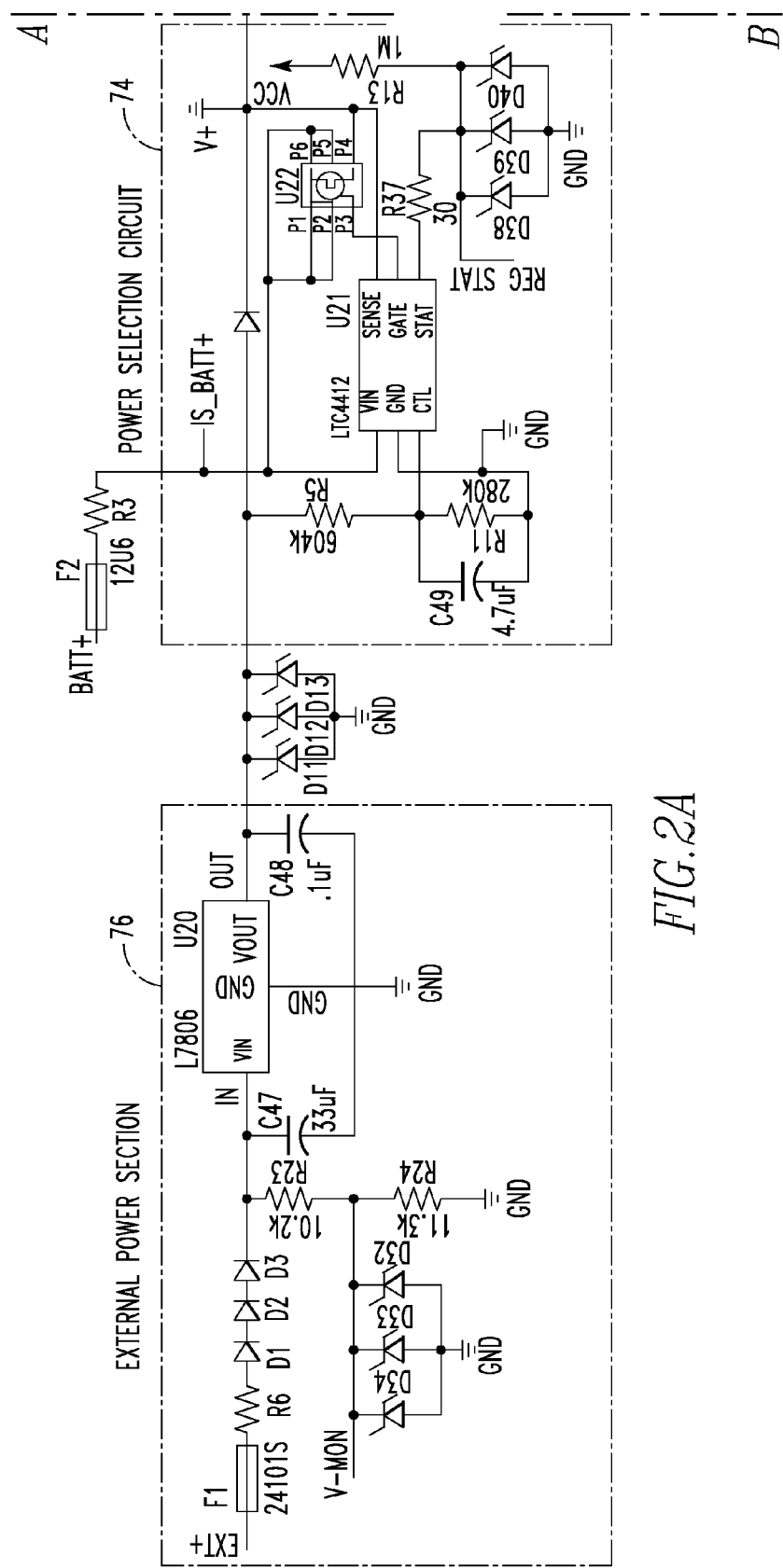
Figure 2B:
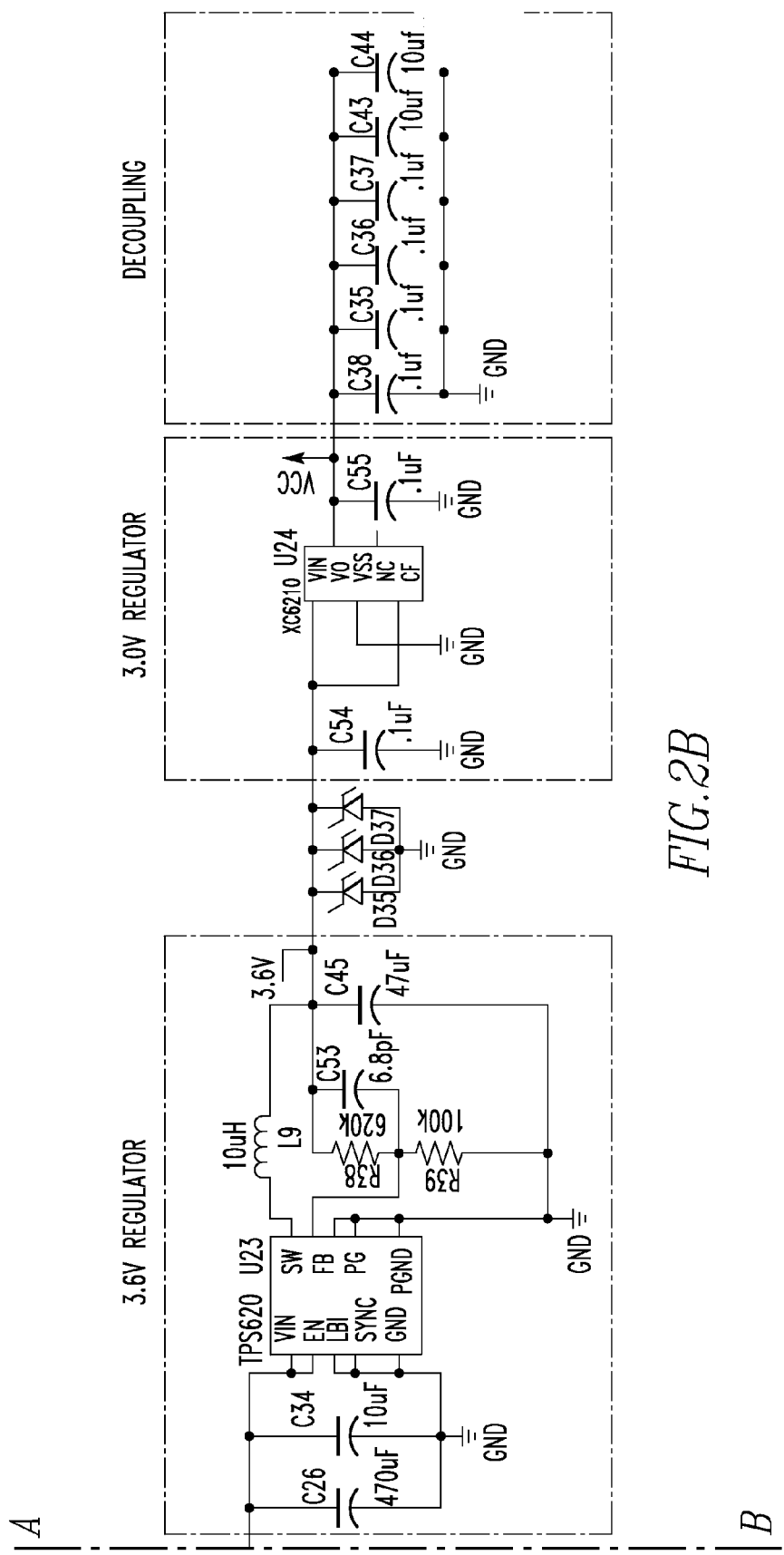
Figure 2C:
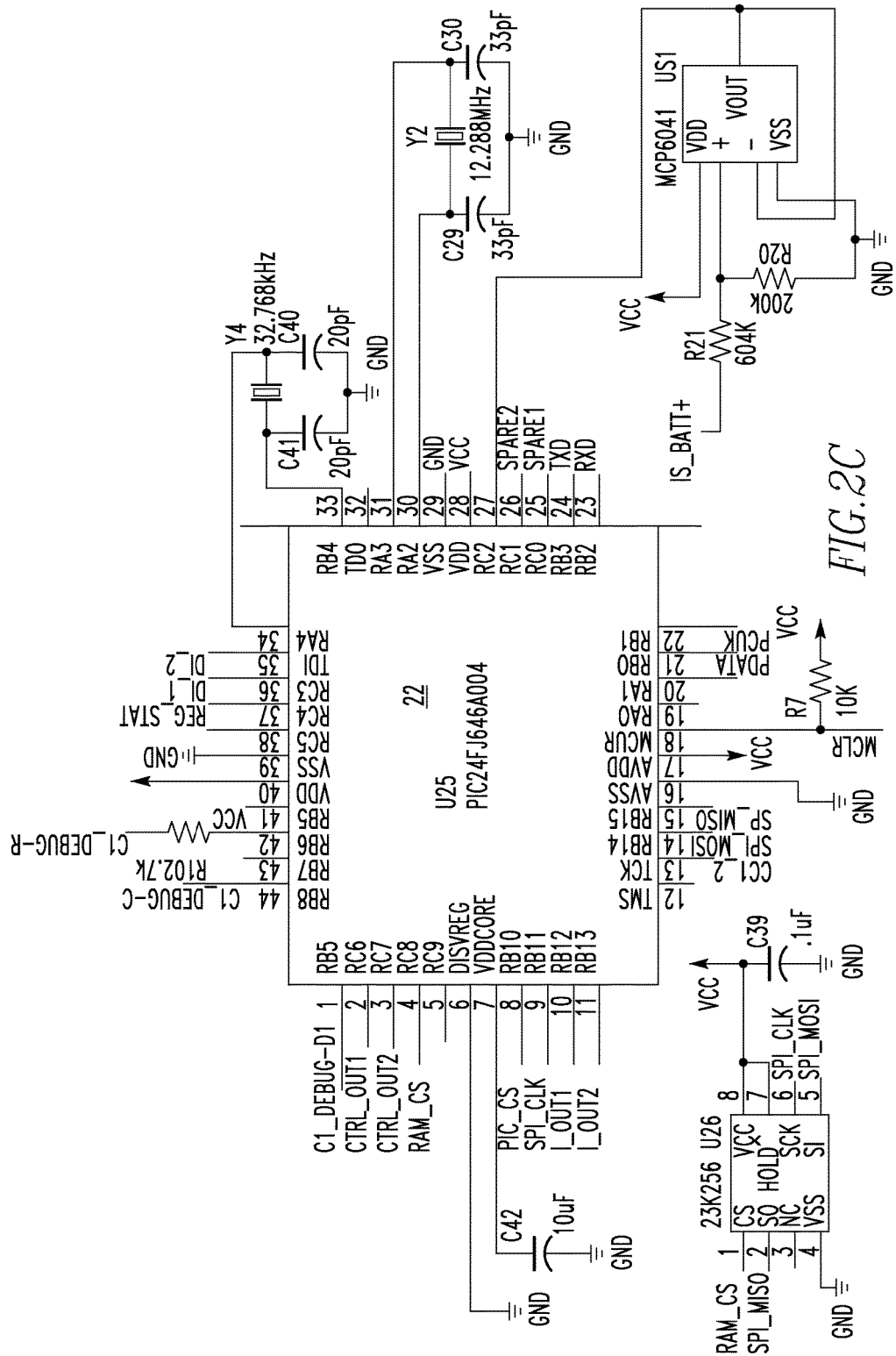
Figure 2D:
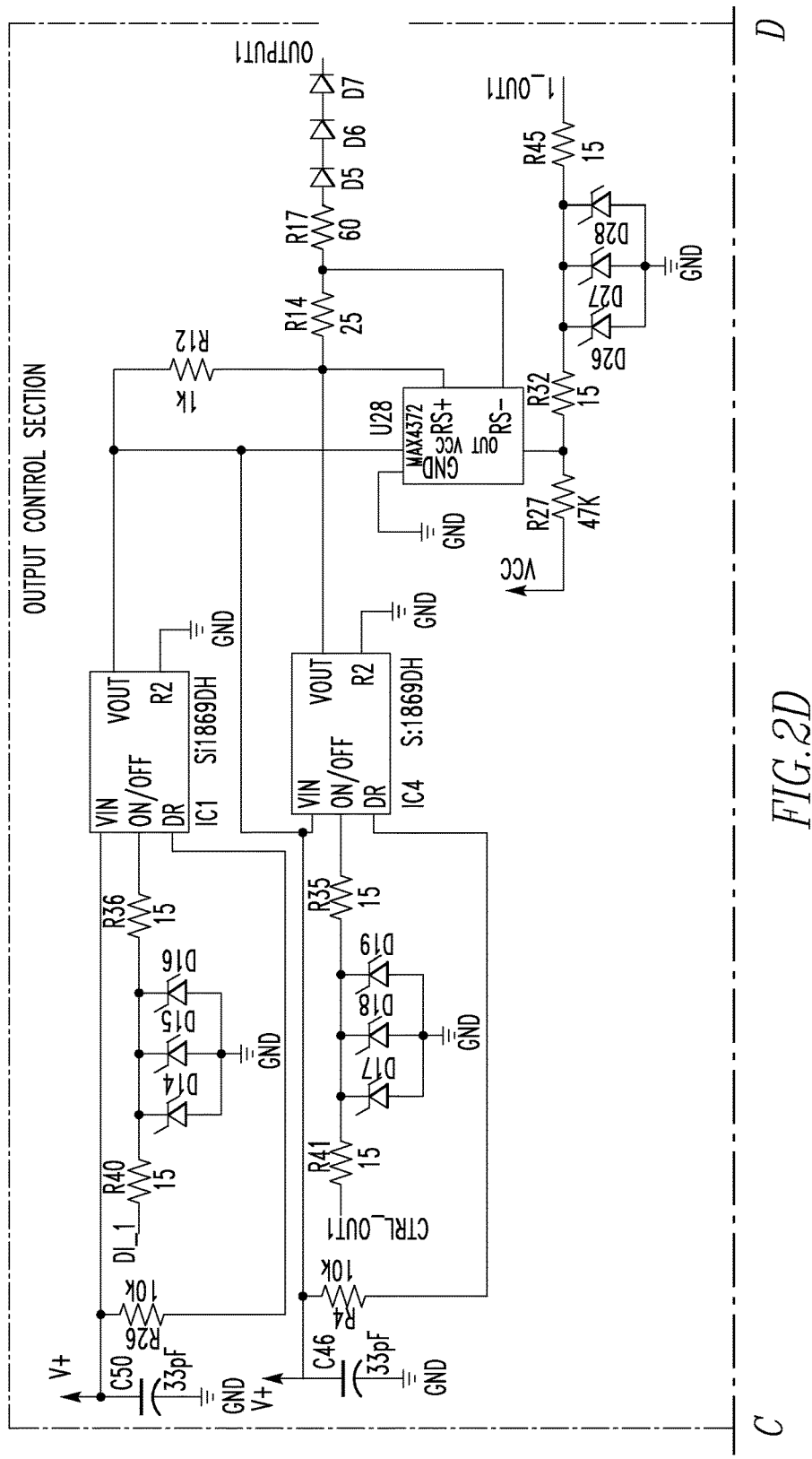
Figure 2E:
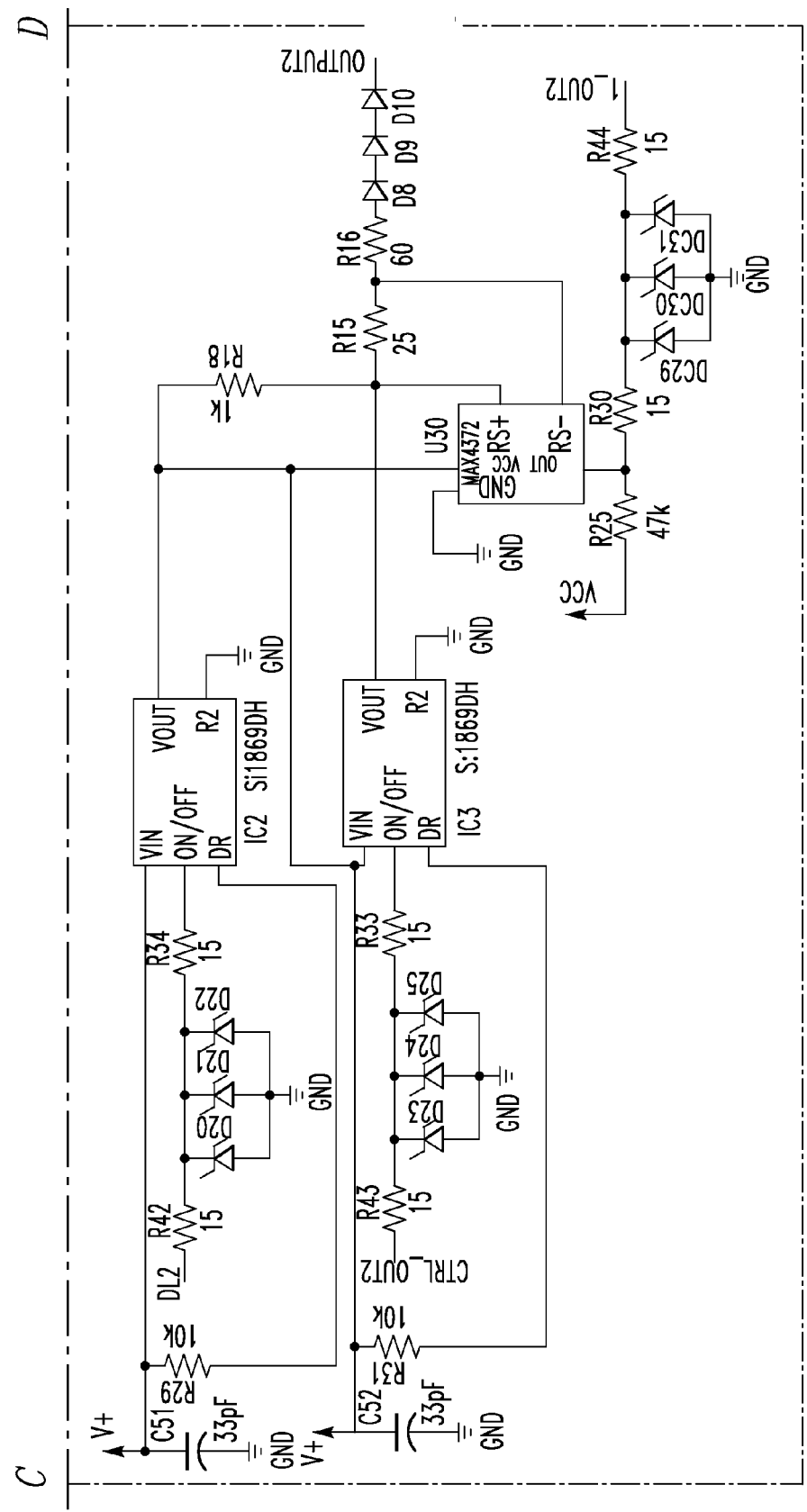

En regard to FIG. 1B, the screw terminal corresponds to the description of FIGS. 8 through 10 can connect to a given output 56 or input 54 depending on the configuration. The pin headers connect to the gas detection portion, here specifically the Trolex assembly card. The program headers connect to the pic 24 through J 3 into the CC1110 through J 5.

In regard to FIGS. 2A-2E, depending on whether the apparatus is in an input 54 configuration or an output configuration, the pic 24 through L out 1 and L out 2 communicates to control out 1 and control out 2, respectively, of the output control section which then is provided, for instance through output 1 and output 2, respectively, to the audio alarm 30 and the video visual alarm 32, respectively, if in the output configuration. When in the input 54 configuration, the outputs 56 are reversed and are inputs 54, so the pic 24 receives input 54 signals from input 1 (instead of output 1) and from input 2 (instead of output 2) and these input signals follow a reverse direction back to the pic 24 from that described above in the output direction, that is to control out 1 and control out 2, respectively, to L out 1 and L out 2, respectively, of pic 24.

As explained above, and with reference to FIG. 6, when in the output configuration, output 1 is used for the visual alarm 32, and output 2 is used for the audible alarm. In the output mode, and with reference to FIG. 9, terminal 1 has a voltage, for instance 1.2 V, connected to the visual alarm 32 load, and terminal 2 is connected to ground and the visual alarm 32 load. The 1.2 V energizes the visual alarm 32 when the switch is closed. Similarly, output 3 has 1.2 V and energizes the audible alarm, and either terminal 5 or terminal 2 is connected to ground and the audible alarm. In this configuration, the operation of the alarms is as described above.

If the monitor 10 is desired to be in the input 54 configuration, as shown in FIG. 7, the monitor 10 is used to monitor 10 whatever the device, such as a field switch or pull cord or emergency stop, is connected to it. Here, terminal 1 has 1.2 V on it and is connected to the device being monitored, here a field switch, as shown in FIG. 8. Terminal 2 is connected to ground and to the field switch. When the switch is closed, pic 24 senses the 1.2 V going to ground and produces a field switch signal that is then converted by the pic 24 into a form that can be sent wirelessly by the apparatus, as described above in regard to the description of the gas value being sent wirelessly from the apparatus.

Similarly, and with reference to FIG. 8, a second device 62, such as a pull cord, can be in electrical connection with terminal 3 having 1.2 V. Terminal 5, which is ground, is electrically connected to the second device 62, such as the pull cord, and the same description is applicable in sending a signal involving the pull cord being pulled occurs as described for the field switch connected to terminals 1 and 2.

As shown in FIG. 10, the terminal is a six position terminal disposed on the housing 12 and accessible from outside the monitor 10. Terminal 1 is either the first output 74 or input, terminal 2 is ground, terminal 3 is the second output 76 or input, terminal 4 is electrically connected to the battery 14, terminal 5 is ground, and terminal 6 is connected to external power for the apparatus to receive external power.

Accordingly, when in the input 54 configuration, which is established prior to the monitor 10 being positioned at a desired location in the mine, input 1 and input 2 of the terminal can receive signals through hardwired connections with various types of devices, to allow for the devices to be monitored. In the output configuration, the same terminals having input 1 and input 2 are now output 1 and output 2 and are configured as described above, for the pic 24 to send alarm signals to activate the audible and visual alarms 30, 32.

The following are features of the apparatus.
Sound Output Level: >90 dB at 12 inches
  Constant tone in range of 2,000-4,000 Hz
  Dual sounders and horns for 180 degree coverage
Visual Alarm: Constantly on high intensity LEDs; color selected by jumper on board
  Red for CO; Green for CH4; Blue for H2S
Supply Voltage: Typically 3.9 VDC, Min 3.5 VDC, Max 6 VDC
Supply Current: <80 ma consumption of simultaneous AV operation
Control Signal: Power will be switch on/off from Sentro Gas detector 70
Mounting Arrangement: Mounted under the Sentro-1 Wireless Sensor using the two cable glands 28 for fixing and routing the wiring. The module must allow for external 12-30 VDC to be connected to the Sentro-1 terminals.
Powered from commercially available batteries giving 40 to 45 days operating life.
Wireless output board with internal antenna 52.
Measures CO, H2S, CH4 options for other gases
Able to interrogate Modbus registers via wireless system
Large LCD screen
Programmable set points
Option to monitor external relay contacts and to report their state via the wireless system
Wireless operation removes need for expensive setup and maintains wired setup.
Measures gas concentrations every 1 second and reports status every 90 seconds, except under warning and alert conditions when changes reported immediately.
Display backlight is turned on whenever control button is pressed. A warning or alert triggers the screen to flash.
Sensors draw minimum power to maximize battery 14 life.
Dual-wall housing 12 gives maximum impact strength.
Housing 12 cover can be removed with power applied for module replacement and servicing.
Simultaneously monitor up to 8 different gases, together with levels of temperature, air velocity, pressure, smoke and fire.
Power Conditioning
  (M) provide power conditioning from a (4) D-Cell EN95 battery pack
  (M) monitor the voltage of the battery pack (M) provide 3.3V 50 ma to the controller and display boards
(M) power CommTrac transceiver
(D) powered from external power voltage
(D) measure the external power voltage
Communications (CommTrac Transceiver)
(M) Support DART communications with Trolex board
(M) Write and Read Mod-Bus registers from the Trolex board
(M) Contain an internal antenna
I/O
(D) Input from a dry contact (state open/closed)
(D) Output power to contact (Batt or Ext Pwr)
Integrated I/O Module The following are a list of parts with reference to FIGS. 1a, 1b and 2), all of which are individually alone well-known and are identifiable by their part number, description and manufacturer.

| Line Item | Reference Designator | Quantity | Manufacturer | Part Number | Description | Alt Part Number |
|---|---|---|---|---|---|---|
| 1 | U$2 | 1 | Linx Technologies, Inc. | CONSMA001-SMD | CONN SMA JACK STR 50 OHM SMD | CONSMA001-SMD-ND |
| 2 | | | | | | |
| 3 | F2 | 1 | | | 1206 SMD, xxA Vfast, fuse | |
| 4 | U1 | 1 | Texas Instruments | CC1110F32RSPR | cc1110, QLP | 296-22740-1-ND |
| 5 | U2 | 1 | Texas Instruments | CC1190RGVT | cc1190, VQFN | 296-25826-2-ND |
| 6 | U25 | | Microchip Technology | PIC24FJ64GA004-E/JL | | PIC24FJ64GA004-E/ML-ND |
| 7 | R3 | 1 | | | RESISTOR, xxOMH 1206 SMD | |
| 8 | C31, C23, C27, C28, C40, C41 | 5 | Kemet | CBR04C200F5GAC | CAP CER 20PF 50 V 1% NP0 P402 | 399-8786-1-ND |
| 9 | C1, C2, C3, C4, C6, C7, C8, C9, C32, C33, C35, C36, C37, C38, C39 | 15 | TDK Corporation | C1005X5R1A104K050BA | CAP CER 0.1UF 10 V 10% X5R 0402 | 445-1265-1-ND |
| 10 | C5, C19 | 2 | TDK Corporation | C1005X5R1C105K050BC | CAP CER 1UF 16 V 10% X5R 0402 | 445-4978-1-ND |
| 11 | C18 | 1 | TDK Corporation | C1005X7R1C103K050BA | CAP CER 10000PF 16 V 10% X7R 0402 | 445-1262-1-ND |
| 12 | C17 | 1 | | 250R07N221JV4T | CAP CER 220PF 25 V 5% NP0 0402 | 709-1125-1-ND |
| 13 | C26 | 1 | | F950J337MBAAQ2 | CAP TANT 330UF 6.3 V 20% 1210 | 493-5795-1-ND |
| 14 | C25, C53 | 2 | TDK Corporation | CGA2B2C0G1H6R8D050BA | CAP CER 6.8PF 50 V NP0 0402 | 445-5580-1-ND |
| 15 | C24 | 1 | TDK Corporation | CGJ2B2C0G1H030C050BA | CAP CER 3PF 50 V NP0 0402 | 445-13278-1-ND |
| 16 | C15, C16, C14 | 3 | TDK Corporation | C1005C0G1H470J050BA | CAP CER 47PF 50 V 5% NP0 0402 | 445-1243-1-ND |
| 17 | C10 | 1 | TDK Corporation | C1005C0G1H010C050BA | CAP CER 1PF 50 V NP0 0402 | 445-4855-1-ND |
| 18 | C11 | 1 | TDK Corporation | C1005C0G1H101J050BA | CAP CER 100PF 50 V 5% NP0 0402 | 445-1247-1-ND |
| 19 | C12, C13 | 2 | TDK Corporation | C1005C0G1H1R5B050BA | CAP CER 1.5PF 50 V NP0 0402 | 445-4858-1-ND |
| 20 | C42, C43, C44, C34 | 4 | TDK Corporation | C1608X5R1C106M080AB | CAP CER 10UF 16 V 20% X5R 0603 | 445-9065-1-ND |
| 21 | C22 | 2 | Johanson Dielectrics, Inc. | 500R07S120GV4T | CAP CER 12PF 50 V 2% NP0 0402 | 712-1256-1-ND |
| 22 | C29, C30, C46, C50, C51, C52 | 6 | TDK Corporation | C1005C0G1H330J050BA | CAP CER 33PF 50 V 5% NP0 0402 | 445-1241-1-ND |
| 23 | C20, C21 | 2 | TDK Corporation | C1005NP01H150J050BA | CAP CER 15PF 50 V 5% NP0 0402 | 445-13788-1-ND |
| 24 | L1, L2 | 2 | TDK Corporation | MLG1005S12NJ | INDUCTOR MULTILAYER 12NH 0402 | 445-3060-1-ND |
| 25 | .3, L4 | 2 | TDK Corporation | MLG1005S18NJ | INDUCTOR MULTILAYER 18NH 0402 | 445-3062-1-ND |
| 26 | L5 | 1 | Pulse Electronics Corporation | PE-0603CD680JTT | INDUCTOR WW RF 68NH 600 MA 0603 | 553-1027-1-ND |
| 27 | L8 | 1 | TDK Corporation | MLG1005S3N3S | INDUCTOR MULTILAYER 3.3NH 0402 | 445-3047-1-ND |
| 28 | L6 | 1 | TDK Corporation | MLG1005S2N2S | INDUCTOR MULTILAYER 6.2NH 0402 | 445-3043-1-ND |
| 29 | L7 | 1 | TDK Corporation | MLK1005S2N2S | INDUCTOR MULTILAYER 2.2NH 0402 | 445-1459-1-ND |

-continued

| Line Item | Reference Designator | Quantity | Manufacturer | Part Number | Description | Alt Part Number |
|---|---|---|---|---|---|---|
| 30 | R4, R7, R26, R29, R31 | 5 | Panasonic Electronic Components | ERJ-2RKF1002X | RES 10.0K OHM 1/10 W 1% 0402 SMD | P10.0KLCT-ND |
| 31 | R1 | 1 | Panasonic Electronic Components | ERJ-2RKF5602X | RES 56.0K OHM 1/10 W 1% 0402 SMD | P56.0KLCT-ND |
| 32 | R2 | 1 | Panasonic Electronic Components | ERJ-2GEJ332X | RES 3.3K OHM 1/10 W 5% 0402 SMD | P3.3KJCT-ND |
| 33 | R8 | 1 | Panasonic Electronic Components | ERJ-2RKF22R0X | RES 22.0 OHM 1/10 W 1% 0402 SMD | P22.0LCT-ND |
| 34 | R10 | 1 | Panasonic Electronic Components | ERJ-2RKF2701X | RES 2.70K OHM 1/10 W 1% 0402 SMD | P2.70KLCT-ND |
| 35 | Y2 | 1 | ECS, INC. | ECS-122.8-20-5PX-TR | CRYSTAL 12.288 MHZ 20PF SMD | XC1278CT-ND |
| 36 | Y1, Y4 | 2 | Abracon Corporation | ABS06-32.768KHZ-T | CRYSTAL 32.768 KHZ 12.5PF SMD | 535-10104-1-ND |
| 37 | Y3 | 1 | CTS- Frequency-Controls | 403C11A26M00000 | CRYSTAL 26.0 MHZ 10PF SMD | CTX951CT-ND |
| 38 | U26 | 1 | Microchip Technology | 23K256-I/ST | IC SRAM 256KBIT 20 MHZ 8TSSOP | 23K256-I/ST-ND |
| 39 | U3 | 1 | TRiQuent Semiconductor | 856327 | Signal Conditioning 915/26 MHz Filter | 772-856327 (mouser) |
| 40 | U24 | 1 | Torex Semiconductor | XC6210B332MR-C | IC REG LDO 3 V 0.7 A SOT25 | 893-1074-1-ND |
| 41 | U20 | 1 | STMicroelectronics | L7806ABD2t-TR | IC REG LDO 6 V 1.5 A D2PAK | 497-1172-1-ND |
| 42 | U23 | 1 | Texas Instruments | TPS62050DGSR | IC REG BUCK SYNC ADJ 0.8 A 10MSOP | 296-14392-1-ND |
| 43 | U21 | 1 | Linear Technology | LTC44121S6#TRMPBF | IC OR CTRLR SRC SELECT TSOT23-6 | LTC44121S6#TRMPBFCT-ND |
| 44 | U22 | 1 | Faichild Semiconductor | FDC638P | MOSFET P-CH 20 V 4.5 A SSOT-6 | FDC638PCT-ND |
| 45 | F1 | 1 | | | FUSE, xxA, 2410 | |
| 46 | R6 | 1 | | | RESISTOR, 2010 | |
| 47 | D1, D2, D3 | 3 | | | DIODE, SHOTTKY, 1206 | |
| 48 | R23 | 1 | | | RESISTOR, xxK. 2010 | |
| 49 | R24 | 1 | | | RESISTOR, xxK, 2010 | |
| 50 | C47 | 1 | TDK Corporation | C1608X5R1E334M080AC | CAP CER 0.33UF 25 V 20% X5R 0603 | 445-5143-1-ND |
| 51 | U31 | 1 | Microchip Technology | MCP6041T-E/OT | IC OPAMP 1.4 V SNGL R-R SOT23-5 | MCP6041T-E/OTCT-ND |
| 52 | IC1, IC2, IC3, IC4 | 4 | Vishay Siliconix | S11869DH-T1-E3 | IC LOAD SW LVL SHIFT 20 V SC70-6 | S11869DH-T1-E3CT-ND |
| 53 | R5 | 1 | Panasonic Electronic Components | ERJ-8ENF6043V | RES 604K OHM 1/4 W 1% 1206 SMD | P604KFCT-ND |
| 54 | C49 | 1 | | GRM188C81E475KE11D | CAP CER 4.7UF 25 V 10% X6S 0603 | 490-7199-1-ND |
| 55 | R11 | 1 | Panasonic Electronic Components | ERJ-2RKF2803X | RES 280K OHM 1/10 W 1% 0402 SMD | P280KLCT-ND |
| 56 | | | | | | |
| 57 | R13 | 1 | Panasonic Electronic Components | ERJ-3GEYJ473V | RES 47K OHM 1/10 W 5% 0603 SMD | P47KGCT-ND |
| 58 | D4 | 1 | | | DIODE, SCHOTTKY | |
| 59 | R9 | 1 | Panasonic Electronic Components | ERJ-3GEYJ105V | RES 1M OHM 1/10 W 5% 0603 SMD | P1.0MGCT-ND |
| 60 | R25, R27 | 2 | Panasonic Electronic Components | ERJ-2GFJ473X | RES 47K OHM 1/10 W 5% 0402 SMD | P47KJCT-ND |
| 61 | | | | | | |
| 62 | | | | | | |
| 63 | D14, D15, D16, D17, D18, D19, D20, D21, D22, D23, D24, D25, D26, D27, D28, D29, D30, D31, D32, D33, D34, D38, D39, D40 | 24 | | | DIODE, ZENER. 6.2 V, SOT-23 | |

-continued

| Line Item | Reference Designator | Quantity | Manufacturer | Part Number | Description | Alt Part Number |
|---|---|---|---|---|---|---|
| 64 | D35, D36, D37 | 3 | Micro Commercial Co. | SMBJ5341B-TP | DIODE, ZENER, 6.2 V, 5 W, DO-214 AC | |
| 65 | L9 | 1 | Wurth Electronics, Inc. | 7445510 | INDUCTOR POWER 10UH 1.2 A SMD | 732-1335-1-ND |
| 66 | C45 | 1 | Kemet | C1210C476M4PACTU | CAP CER 47UF 16 V 20% X5R 1210 | 399-5514-1-ND |
| 67 | C54, C55, C48 | 3 | TDK Corporation | C1608X7R1H104K080AA | CAP CER 0.1UF 50 V 10% X7R 0603 | 445-1314-1-ND |
| 68 | U28, U30 | 2 | Maxim Integrated | MAX4372HECK + T | IC AMP CURRENT SENSE SOT23-5 | MAX4372HEUK + TCT-ND |
| 69 | R18, R19 | 2 | | | RESISTOR, XXXK, 0402 | |
| 70 | R15, R14 | Na | | | RESISTOR, 1 OHM, 1206 | |
| 71 | R16, R17 | 2 | | | RESISTOR, XXXK, 1206 | |
| 72 | D5, 36, D7, D8, D9, D10 | 6 | | | DIODE, SHOTTKY, 0603, 50 V | |
| 73 | R20 | 1 | | ERJ-2RKF2803X | RES 280K OHM 1/10 W 1% 0402 SMD | P280KLCT-ND |
| 74 | R21 | 1 | | ERJ-2RKF6043X | RES 604K OHM 1/10 W 1% 0402 SMD | P604KLCT-MD |
| 75 | R22 | 5 | | | RESISTOR, XXXXK, 1206 | |
| 76 | J1, J2 | 2 | | | HEADER, MALE, .1, 6POS | |
| 77 | J6 | 1 | | | HEADER, SCREW TERMINAL, 6 POS | |
| 78 | J5 | 1 | | | HEADER, MALE, .1, 5 POS | |
| 79 | D11, D12, D13 | 3 | Vishay Semiconductor | BZG03C10TR | DIODE, ZENER 10 V, D0-214 AC | BZG03C10CT-ND |
| 80 | | | | | | |
| 81 | R38 | 1 | Panasonic Electronic Components | ERJ-2GEJ624X | RES 620K OHM 1/10 W 5% 0402 SMD | P620KJCT-ND |
| 82 | R39 | 1 | Panasonic Electronic Components | ERJ-2GEJ104X | RES 100K OHM 1/10 W 5% 0402 SMD | P100KJCT-ND |

The present invention pertains to a system 64 for monitoring gases on an oil or gas rig, as shown in FIG. 13. The system comprises a monitor 10 which detects a gas at the rig and determines a gas value of the gas. The monitor 10 having an audio alarm 30 and a visual alarm 32, which is activated when the detected gas is above a predetermined value, and a transceiver 48 which transmits the gas value. The system 64 comprises a wireless telecommunications network 66 on which the gas value is transmitted from the monitor 10. The system 64 comprises a remote station 68 which receives the gas value from the network 66.

The remote station 68 may include a receiver which receives the gas value from the network 66, a processor 22 in communication with the receiver which receives the gas value from the receiver, and a display 38 in communication with the processor 22 on which the processor 22 displays an alarm indication when the gas value is above a predetermined level.

The present invention pertains to a remote station 68 which receives gas values of gas monitors from a wireless network 66. The remote station 68 comprises a receiver which receives the gas values wirelessly from the network 66. The remote station 68 comprises a processor 22 in communication with the receiver which receives the gas values from the receiver. The remote station 68 comprises a display 38 in communication with the processor 22 on which the processor 22 displays an alarm indication when the gas value is above a predetermined level.

The station 68 may include a housing 12 and the processor 22 and the receiver are disposed in the housing 12 and the display 38 is disposed on a face of the housing 12.

When the monitors 10 are used on an oil or gas rig, the monitors 10 are placed at various locations throughout the rig. A single communication node, such as a CommTrac node is placed with the central control station on the rig, where all of the monitors 10 are monitored. On the rig, since there are no seams or earth to interfere in any way with the transmission and reception of signals by the monitors 10, typically just a single communication node 206 is all that is needed for communication with the monitors 10. The communication node 206 essentially forms a hub network 66 with the monitors 10. The network 66 can be a CommTrac network 66 where data signals are sent over the network 66 as described above between the CommTrac communication node 206 and the monitors 10.

Figure 16:
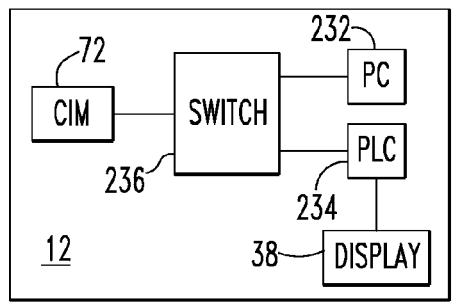
FIG. 16 is a block diagram of a remote station which receives gas values of gas monitors.

In one embodiment, as shown in FIG. 16, the receiver of the remote station 68 is part of the transceiver 48 of the CIM 72 described above, disposed in a housing 12 of the remote station 68. The gas value from each of the monitors 10 on the rig is received over the CommTrac network 66 at the CIM 72. The CIM 72 provides the gas values the CIM 72 has received to the Moxa 230 Miineport, as described above in regard to the shared power supply 200, which converts the serial data signal from the CIM 72 into an Ethernet format signal. The Ethernet signal is provided to a switch 236 which in turn provides it to a Beagle Bone PC 232 through the switch 236 that prepares the signal for a modbus PLC 234.

Figure 17:
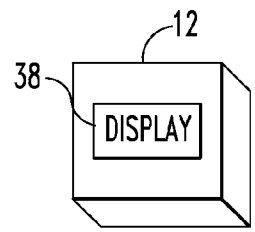
FIG. 17 is a perspective view of a housing of the remote station

The PC 232 provide the prepared signal through the switch 236 to the PLC 234 which then causes the prepared signal to be displayed on the display 38 on the housing 12 face, as shown in FIG. 17. The status of all the monitors 10 are displayed at once on the display 38. The value of the gas, such as methane, at each monitor 10 is displayed as well as an alarm indication at a monitor 10 if the gas value at the monitor 10 is above a predetermined level.

Regarding the protocol for the gas monitor, the message the monitor 10 sends out at predetermined times, or when queried, to the network 66 may have a byte for battery level. The message may have a byte for external voltage level. The message may have a byte for status. The message may have a byte for gas reading. The message may have a byte for node address. The message may have a byte for serial number.

Figure 14A:
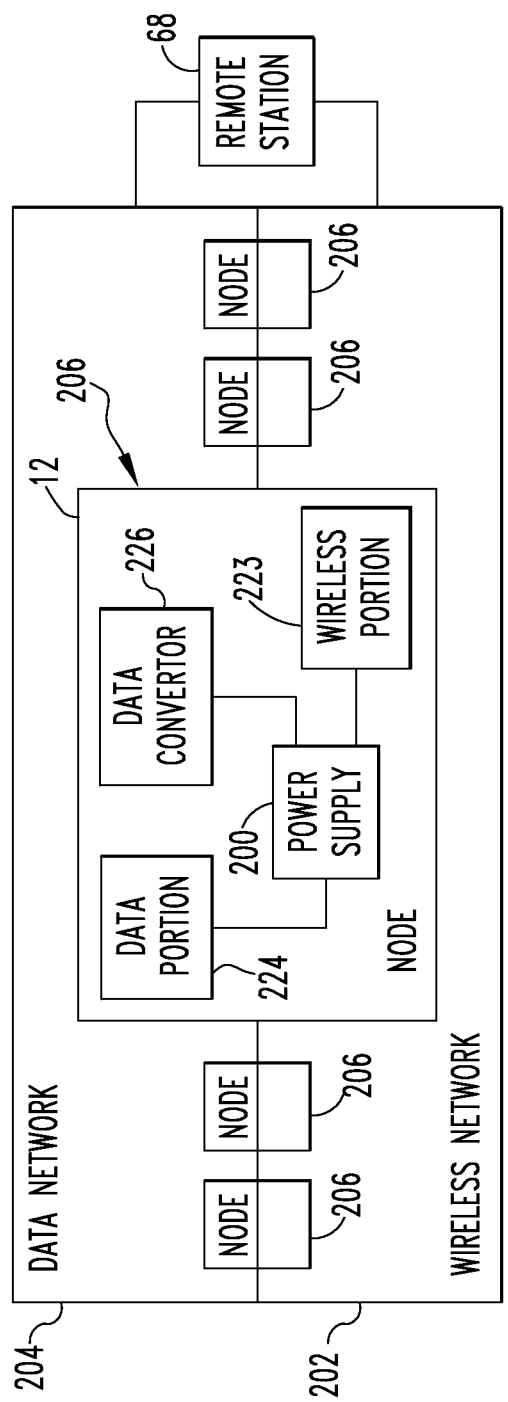
FIG. 14A is a schematic representation of a communication system of the present invention.
Figure 14B:
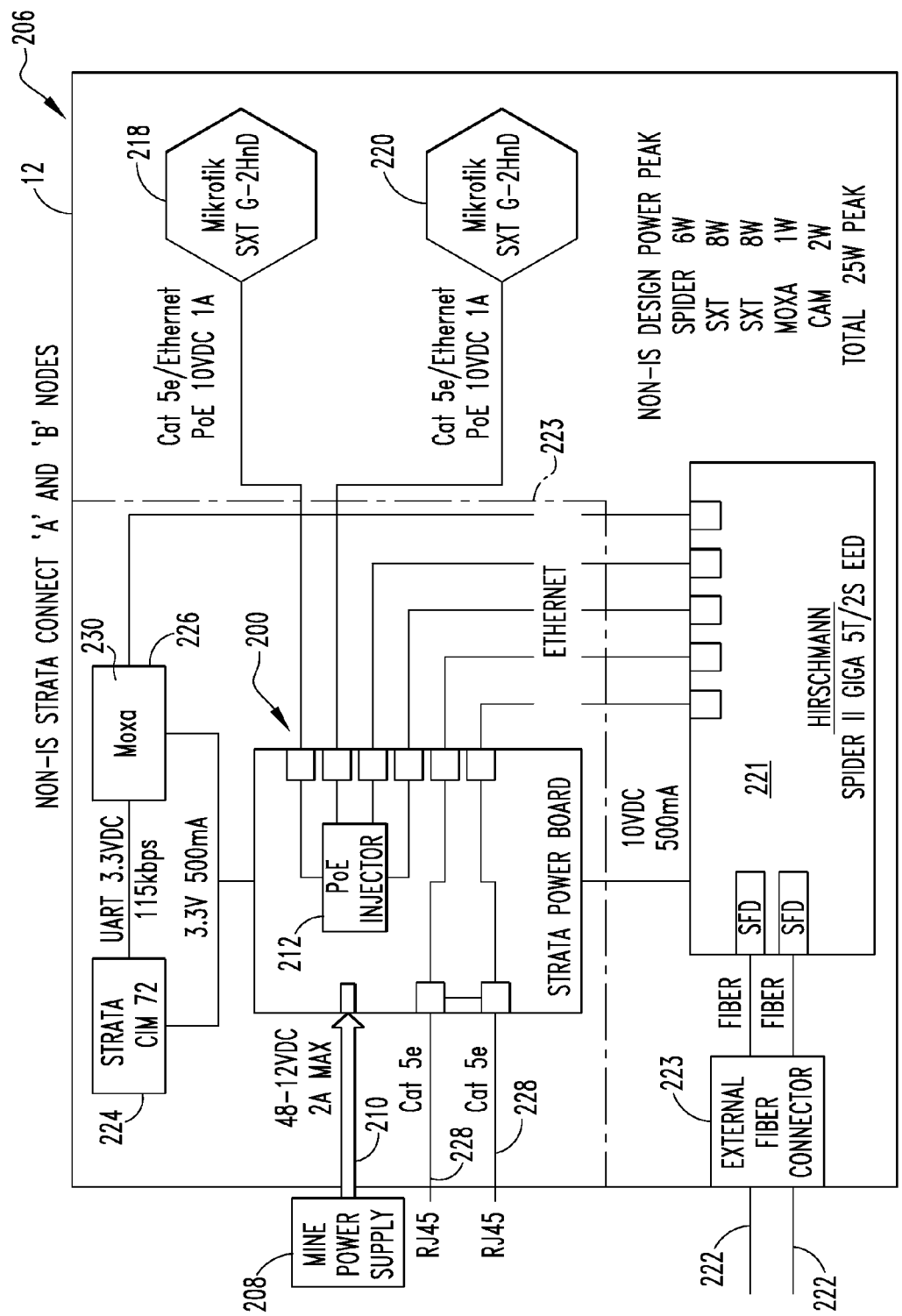

The present invention pertains to a communication system 64, as shown in FIGS. 14a and 14b. The system 64 comprises a data network 204 on which solely data is sent. The system 64 comprises a wireless network 202 on which voice and data is sent bidirectionally. The system 64 comprises a plurality of nodes 206 distributed and apart from each other that form the data network 204 and the wireless network 202. Each node 206 has a data portion 223 which receives and sends data on the data network 204, a wireless portion 224 which receives and sends voice signals on the wireless network 202, and a power supply portion 200 in electrical communication with the data portion 224 and the wireless portion 223 which powers the data portion 224 and the wireless portion 223.

Data on the data network 204 may include tracking information of an individual. The data on the data network 204 may be sent and received at least one node 206 of the plurality of nodes 206 and the data network 204 is bidirectional. The data from the data network 204 may be sent on the data network 204 and the wireless network 202. Each node 206 may include a data converter 226 in communication with the data portion 224 and the wireless portion 223 which converts the data from the data network 204 into a transmission signal that is transmitted on the wireless network 202.

The present invention pertains to a communication node 206 of a data network 204 and a wireless network 202, as shown in FIGS. 14a and 14h. The node 206 comprises a housing 12. The node 206 comprises a data portion 224 disposed in the housing 12 which receives data wirelessly on the data network 204. The node 206 comprises a wireless portion 223 disposed in the housing 12 which receives and sends voice signals on the wireless network 202. The node 206 comprises a power supply portion 200 disposed in the housing 12 in electrical communication with the data portion 224 and the wireless portion 223 which powers the data portion 224 and the wireless portion 223. The node 206 comprises a data converter 226 disposed in the housing 12 in communication with the data portion 224 and the wireless portion 223 which converts the data from the data network 204 into a transmission signal that is transmitted on the wireless network 202.

The wireless portion 223 may include a first radio 218 to transmit the transmission signal. The wireless portion 223 may include a switch 221 in communication with the first radio 218 and the data converter. The wireless portion 223 may include an external fiber connector 223 in communication with the switch 221 to connect with an external fiber to transmit the transmission signal.

The present invention pertains to a method for communicating in a mine. The method comprises the steps of receiving data wirelessly at a data portion 224 of a first node 206 of a plurality of nodes 206 from a data network 204 on which solely data is sent. The plurality of nodes 206 distributed and apart from each other and form the data network 204 and a wireless network 202. There is the step of converting with a data converter 226 in communication with the data portion 224 the data from the data network 204 into a transmission signal that is transmitted on the wireless network 202. The wireless network 202 transmitting and receiving voice and data bidirectionally. There is the step of transmitting the transmission signal from the first node 206 on the wireless network 202 with a wireless portion 223 of the first node 206. There is the step of powering the data portion 224 and the wireless portion 223 with a power supply portion 200 in electrical communication with the data portion 224 and the wireless portion 223.

Referring to FIG. 14B, there is shown a schematic diagram focusing on the shared power supply 200 that is shared by the wireless network 202 and the wireless data network 204 which is separate and distinct and independent from the wireless network 202, all of which is found in a single communication node 206, such as a StrataConnect node 206 A. The wireless network 202 may be that wireless network 202 as described in U.S. application Ser. No. 14/290,755, incorporated by reference herein, which supports and provides for bidirectional voice and data communication. The data network 204 may be the CommTrac network 66 sold by Strata Products Worldwide, LLC, Sandy Springs, Ga. The data network 204 may provide bidirectional data communication, as well as tracking of miners and vehicles and various devices throughout the mine. The node 206 receives data from the data network 204, processes the data so the data can be transmitted on the wireless voice network 202 with the fibers 222, and then transmits the processed data on to the remote station 68, either through the Wi-Fi network 202 with the fibers 222.

A node 206 having the functionality of the CommTrac network 66 and the wireless network 202 receives power from the mine power supply 208 at power input 210. The power from the mine power supply 208 is at between 12 and 48 VDC. The power input 210 is electrically connected to a POE injector 212 which converts the power to 10 VDC to power the components inside the node 206. Power from the injector 212 at 10 VDC and 1 amp is provided to the first radio 218 and second radio 220 over a Cat5/Ethernet connection connected to each radio. Power from the injector 212 at 10 VDC and 500 mA is provided to the switch 221 in the node 206. Also connected to the switch 221 are external fibers 222 through external fiber connectors 223 over which transmission and reception of communication signals occur. The injector 202 powers the data connection portion 224, here preferably the CommTrac portion 224, such as a CIM 72 that communicates with the CommTrac network 66 and a data converter 226, such as a serial to Ethernet converter 226, and specifically a Moxa 230, at 3.3 V and 500 mA.

The CommTrac portion 224 connects with the serial to Ethernet converter 226 through a UART connection at 3.3 VDC and at 115 kb per second which provides the data signal received by the CommTrac portion 224 to the serial to Ethernet converter 226. The serial to Ethernet converter 226 converts the data signal received by it from the CommTrac portion 224 into a form that can then be transmitted through the fibers 222 or through the radios and provides the converted signal to the switch 221. The switch 221 then transmits the converted signal that was originally received by the CommTrac portion 224 through the fibers 222, or if the fiber connection is not available, through the radios.

In addition, the node 206 may also receive power from another node 206 through a Cat 5 connection 228 and also provide power to another node through a Cat 5 connection 228 to form a daisy chain of nodes 206. Each of the Cat 5 power connections 228 are RJ45 connectors. The power level of the Cat 5 connections 228 coming in or going out of the node 206 is the same as the power level received by the node 206 from the mine power supply 208.

FIG. 14B shows a non-IS node 206. FIG. 14C shows a node 206 that is IS. The node 206 operates essentially the same as the node 206 of FIG. 14B, except that certain power levels are different, as indicated, and the external Cat 5 connections 228 are omitted.

The present invention pertains to a miner communicator 298 in a communications network 66, as shown in FIG. 15. The communicator 298 comprises a housing 12. The communicator 298 comprises a processor 22 disposed in the housing 12. The communicator 298 comprises a transceiver 48 disposed in the housing 12 and in communication with the processor 22 and the network 66 to send to and receive from the network 66 only data but not including text. The communicator 298 comprises an input 300 disposed on the housing 12 and in communication with the processor 22 which provides a trigger signal to the processor 22. The communicator 298 comprises an alarm 302 in contact with the housing 12 and in communication with the processor 22 that is activated by the processor 22 when an alarm 302 signal is received by the transceiver 48. The communicator 298 comprises a tracking portion 310 disposed in the housing 12 which provides a tracking signal that is transmitted by the transceiver to the network from which the location of the housing in the mine is determined along with an ID of the communicator 298. The transceiver 48 transmits the ID and tracking signal to the network 66 to a communication node 206, ideally the closest node 206, and then to the remote station 68. The tracking portion 310 may be part of the CC 1110. The CC 1110 is an off the shelf transceiver that is purchased and also provides tracking ability by measuring the signal strength of the CommTrac node 205 ideally closest to the transceiver 48, whose location is known and stored in a server in the remote station 68. The signal strength is sent through the network 66 to the server and using triangulation by the server, which receives the signal strength, determines the location of the transceiver 48, as is more fully explained below and is already part of the Comm rac network 66.

The input 300 may be a single button 304. The alarm 302 may be a first LED 306 that illuminates when the alarm 302 signal is received by the transceiver 48. The alarm 302 may be a plurality of LEDs 306 which is illuminated when the alarm 302 signal is received by the transceiver 48. There may be no display 38 and no key board or key pad, only the single button 304.

The trigger signal may be a fixed shape signal whose duration corresponds to how long the button 304 is activated. The alarm 302 may be activated only when an alarm 302 signal is received during to listening intervals in a listening period by the transceiver 48. The activation of the button 304 may cause the processor 22 to produce an indicator signal to the network 66 through the transceiver 48 corresponding to the activation length and activation frequency of the button 304.

The transceiver 48 may have its settings changed by the processor 22 when the communicator 298 is within a predetermined distance of a communication node so the transceiver 48 is not saturated by the communication node. When the communicator 298 transitions from an area of surface communication nodes to only underground communication nodes, the processor 22 may transmit to the network 66 through the transceiver 48 a check in message that the communicator 298 is present in the mine.

The present invention pertains to a method for communicating with a miner in a mine. The method comprises the steps of sending an alarm 302 signal wirelessly through a wireless communication network 66 to a miner communicator 298 carried by a miner in the mine. The communicator 298 is only able to receive data but not voice. There is the step of receiving the alarm 302 signal by the communicator 298. There is the step of activating an alarm 302 of the communicator 298 by a processor 22 of the communicator 298 in response to the communicator 298 receiving the alarm 302 signal. There is the step of activating a button 304 of the communicator 298 to cause the transmitter to transmit from the communicator 298 to the network 66 an indicator signal regarding the miner's status, and with the indicator signal is an id of the communicator 298 and information associated with the position of the communicator 298, The communicator 298 does not have a display 38 or a keyboard.

The communicator 298 for communicating with a user, such as a miner, provides for limited but important information transfer between the user and a monitoring station. This limited information transfer is bidirectional to provide the remote station 68 with information about the user, and to provide the user with critical emergency alert information. The communicator 298 is very lightweight so that it is easily carried or worn by the user and is battery powered.

The communicator 298 sends position messages that report the ID, the current position data by providing the signal strength of signals received by the communicator 298 from a closest operable communication node 206 in the mine to the communicator 298, the ID of the closest communication node 206 and possibly battery level, and event information at predetermined intervals wirelessly over a network 66 to the remote station 68 so the miner can be tracked. The network 66 can be the CommTrac network 66 or the StrataConnect network 66, which is comprised of the CommTrac network 66 and a WiFi network 66, as described above. The communicator 298 will listen for any messages sent to it at different predetermined intervals.

The communicator 298 includes a processor 22, such as a PIC 24, and a transceiver 48, such as a CC1110, and can be the CIM 72, the operation of which is already described above in regard to the operation of the wireless gas monitor 10. The CommTrac network 66 is synchronized with the communicator 298 so that when the communicator 298 sends information or receives information at the appropriate predetermined intervals, the CommTrac network 66 knows to send or receive the respective information in the appropriate timeframe.

When the communicator 298 is within a predetermined distance of a CommTrac node, the transceiver 48 is attenuated by about 10 db, and its RSSI values are adjusted upward by the same amount. This is to deal with the condition of a CommTrac node being very close to the communicator 298 and saturating the transceiver 48. The transmission power of the transceiver 48 is also reduced by 10 db if the communicator 298 is close to the CommTrac node so as to prevent saturating the CommTrac node transceiver 48.

During listening periods by the communicator 298 to receive information, a mine-wide alert state bit is used to determine that an emergency condition exists. This bit must be detected in at least two listening intervals within a predetermined listening period to be considered valid. By requiring information received by the communicator 298 in at least two listening intervals in a predetermined listening period to have this bit, it reduces the possibility of false alarms. When none of the listening intervals in the predetermined listening period have this hit, the alert state is considered no longer present.

A light on the apparatus will flash, preferably in a distinct pattern, when the mine-wide alert is recognized by the communicator 298. After a mine-wide alert is recognized; the miner will press a button 304 one, two or three times to indicate the miner's status. For instance, if the button 304 is pushed once, it means the miner is fine. If the button 304 is placed twice in succession, it means the miner is trapped. If the miner pushes the button 304 three times in succession, it means the miner is injured. The miner can push the button 304 twice, then wait a few seconds and push it again three times to indicate he is trapped and injured. The communicator 298 will send an emergency response acknowledgment with the position message to indicate the miner's response. The light may be several LEDs 306 of different color.

A quick press on the button 304 performs a communication check and battery status update. Holding down the button 304 for an extended period of time or multiple presses of the button 304 during a short period of time is used to trigger an emergency message. Holding down the button 304 for an extended period of time shall remove this condition. Two quick presses of the button 304 turn the LED 306 flasher on or off. In response to a mine-wide alert message, one, two or three presses indicate the user's response condition.

One bit of received information in a listening interval is used to indicate if the CommTrac node is a surface node. Transitioning from an area of surface nodes to only underground nodes triggers the apparatus to issue a check in message. A checkout message is transmitted when transitioning in the other direction-transmitting a checkout message when only surface nodes are heard and the apparatus is formally in a "check in" state. The apparatus only waits for the network 66 level acknowledgment that indicates the check in/out message made it successfully to the CommTrac node. The apparatus does not need to wait for check in/out acknowledgment.

For a communication check, after the button 304 is quickly pressed, the LEDs 306 flash once immediately to provide feedback. After a short pause, a series of 1-3 LED 306 flashes indicate battery life (1—needs replacing soon, 2—middle life, 3—new). Alter another pause, a second series of flashes indicate strength of node (1—weak, 3—strong). The LEDs 306 will flash in a pattern indicative of an emergency state. For example, a—flash with pauses in between will indicate an emergency state. The LEDs 306 will flash in a basic pattern used only for visual warning. During a mine-wide alert message, the LEDs 306 blink in a pattern making it very clear the apparatus is in an alert state.

The housing of the communicator 298 has a l×w×h of less than 110 mm×210 mm×50 mm and is preferably about 72 mm×165 mm×20 mm. It has a weight of less than 150 gm and is preferably about 75 gm.

Figure 18:
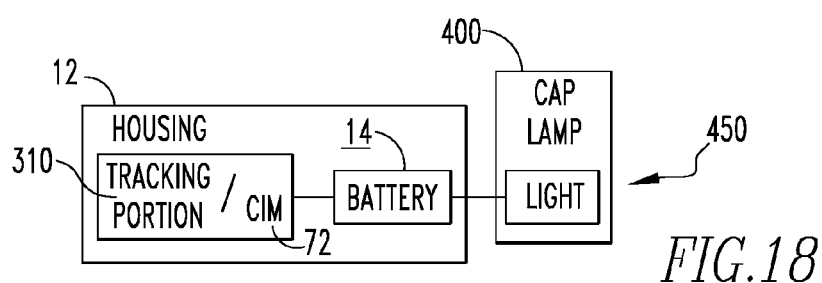
FIG. 18 is a block diagram of a miner apparatus with a cap lamp and tracking.
Figure 21:
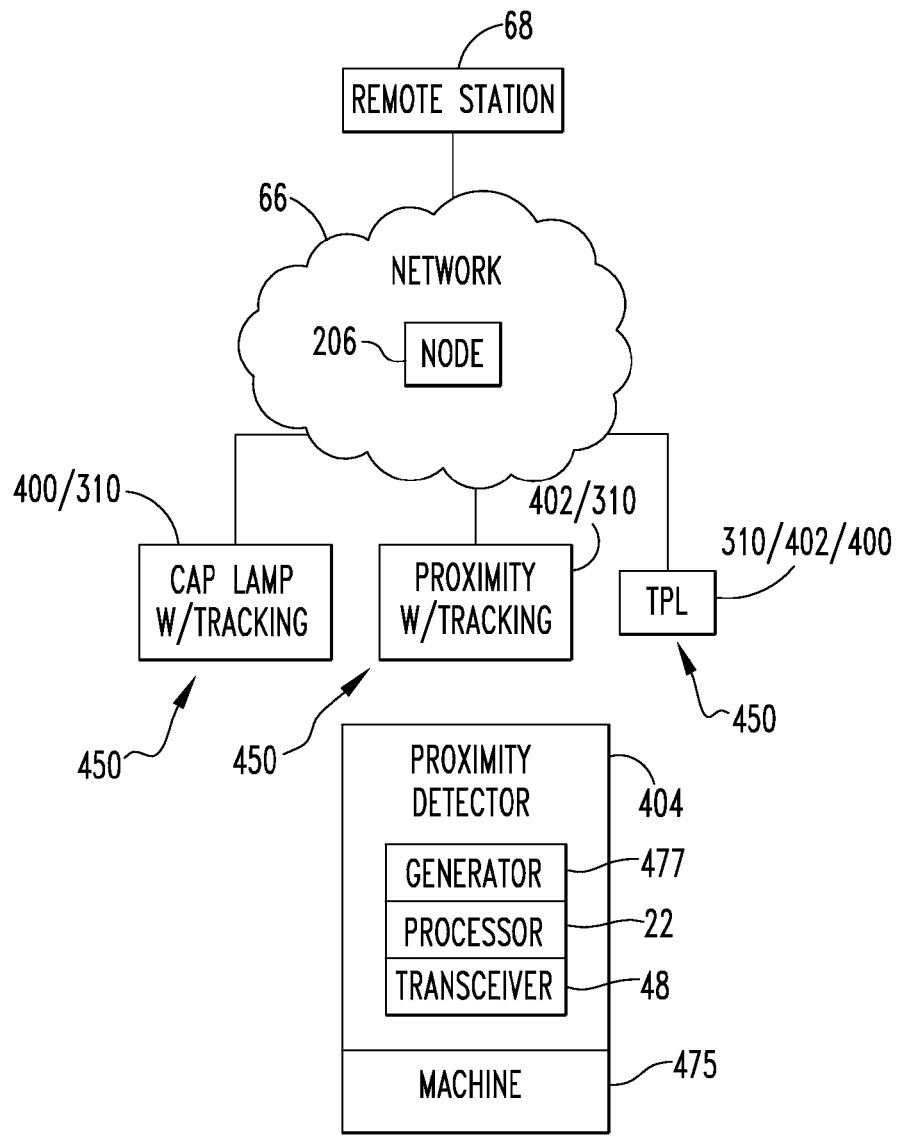
FIG. 21 is a representation of a system for a miner.
Figure 22A:
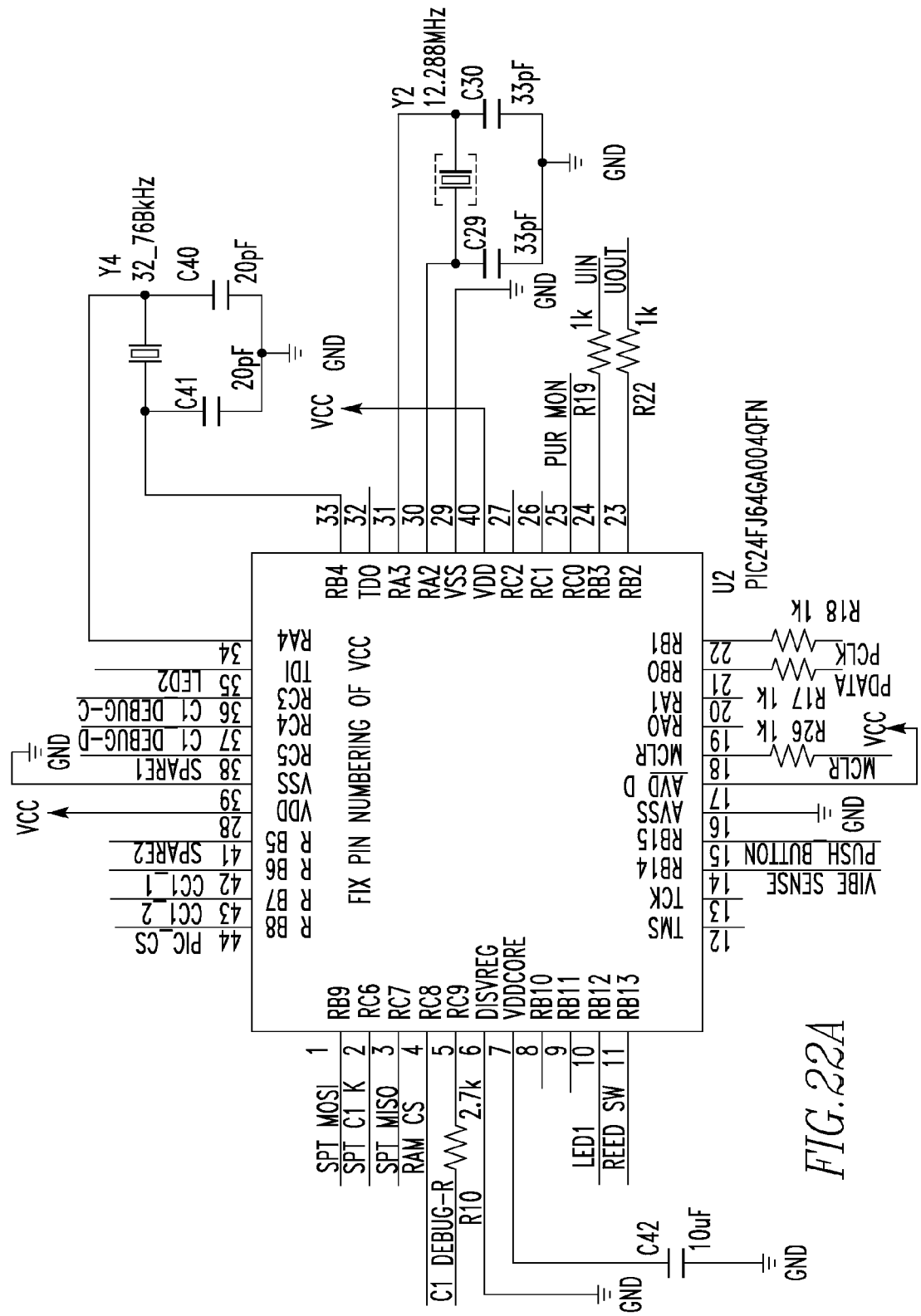
Figures 22B, 22C:
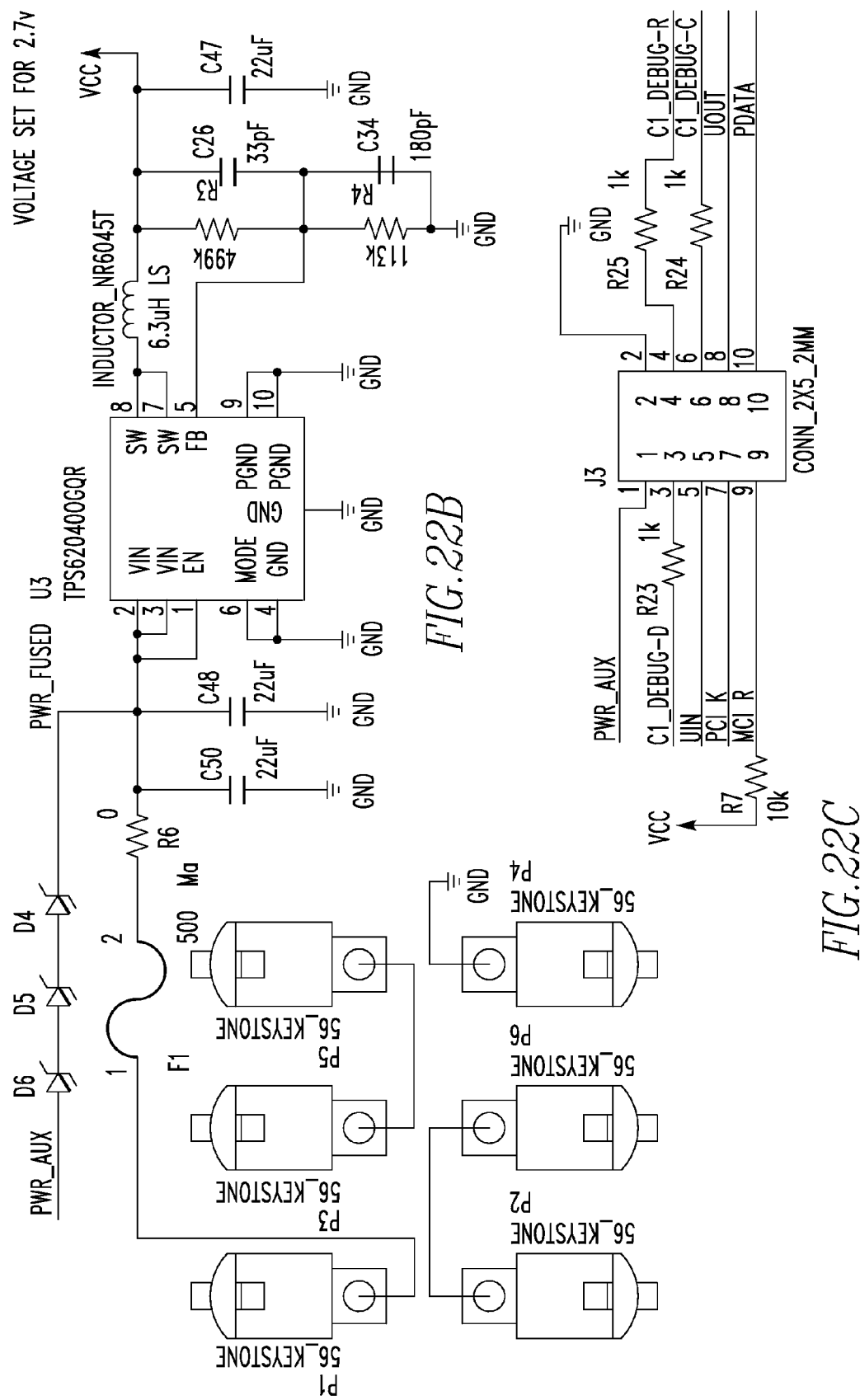
Figure 22D:
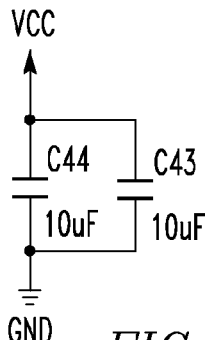
Figure 22E:
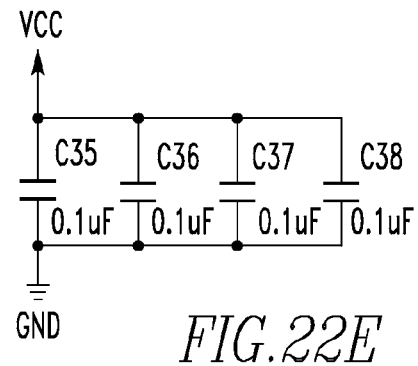
Figure 22F:
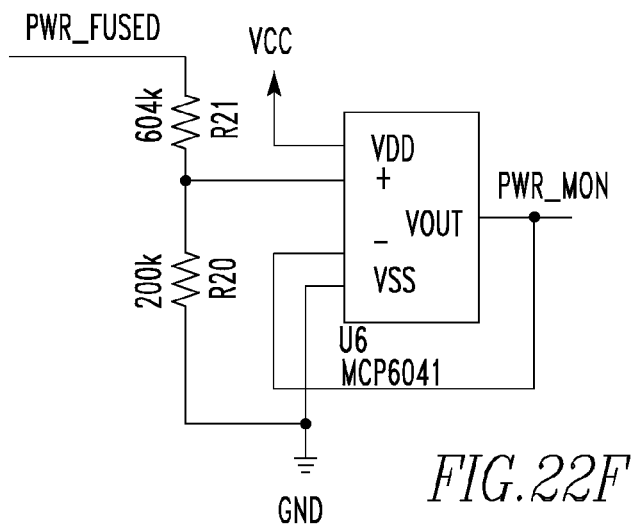
Figure 22G:
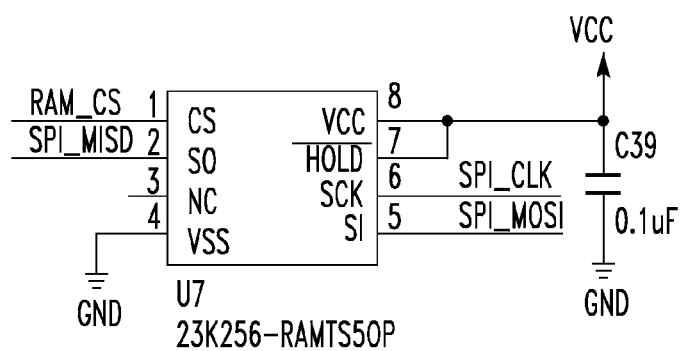
Figure 22H:
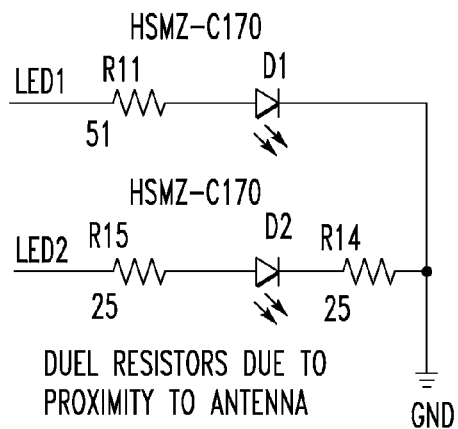
Figure 22I:
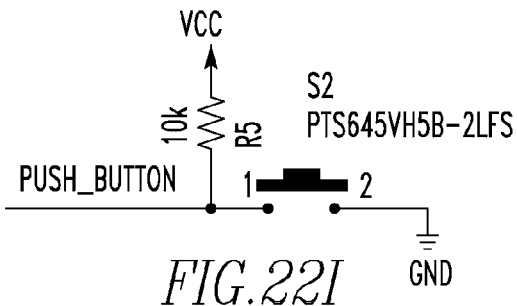
Figure 22J:
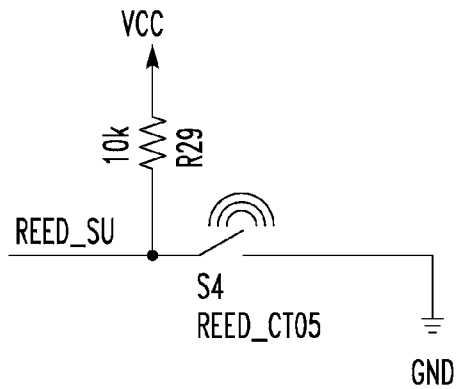
Figure 22K:
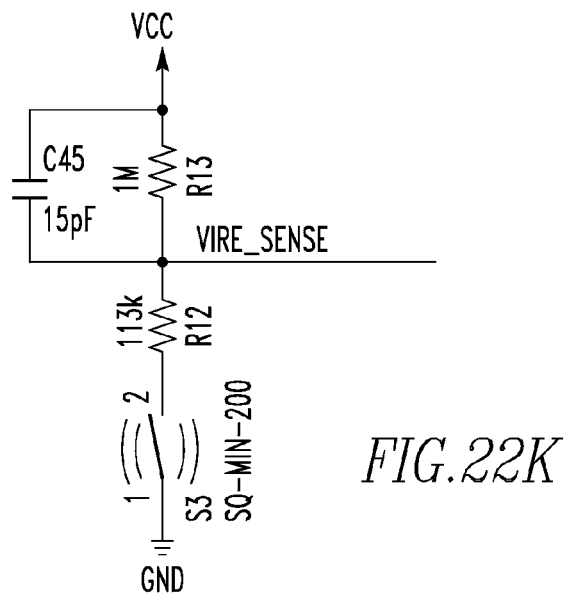

Then present invention pertains to a miner apparatus 450 of a wireless network, as shown in FIG. 18 and FIG. 21. The apparatus 450 comprises a housing 12 which is carried by the miner. The apparatus 450 comprises a tracking portion 310 disposed in the housing 12 which transmits information associated with the miner's location wirelessly to the network 66. The apparatus 450 comprises a battery 14 disposed in the housing 12 and connected to the tracking portion 310 which powers the tracking portion 310. The apparatus 450 comprises a cap lamp 400 electrically connected to the battery 14 which is powered by the battery 14 to provide light. The cap lamp 400 is worn by the miner.

The tracking portion 310 may be part of a transceiver 48, described above, and the location of the housing 12 is determined, as described.

Figure 19:
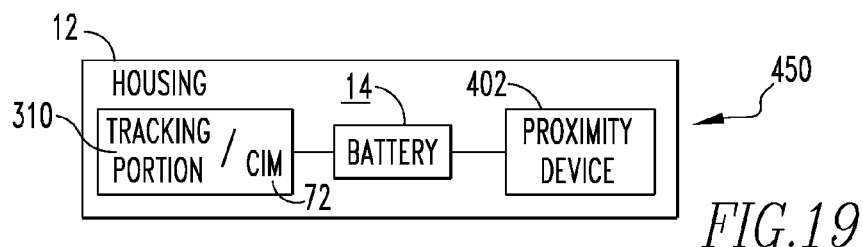
FIG. 19 is a block diagram of a miner apparatus with a proximity device and tracking.

The present invention pertains to a miner apparatus 450 of a wireless network 66, as shown in FIG. 19 and FIG. 21. The apparatus 450 comprises a housing 12 which is carried by the miner. The apparatus 450 comprises a tracking portion 310 disposed in the housing 12 which transmits information associated with the miner's location wirelessly to the network. The apparatus 450 comprises a battery 14 disposed in the housing 12 and connected to the tracking portion 310 which powers the tracking portion 310. The apparatus 450 comprises a proximity device 402 electrically connected to the battery 14 and disposed in the housing 12 which is powered by the battery 14 to provide a detectable presence to a proximity detector 404 when the miner gets too close to the proximity detector 404, the proximity device 402 worn by the miner.

Figure 20:
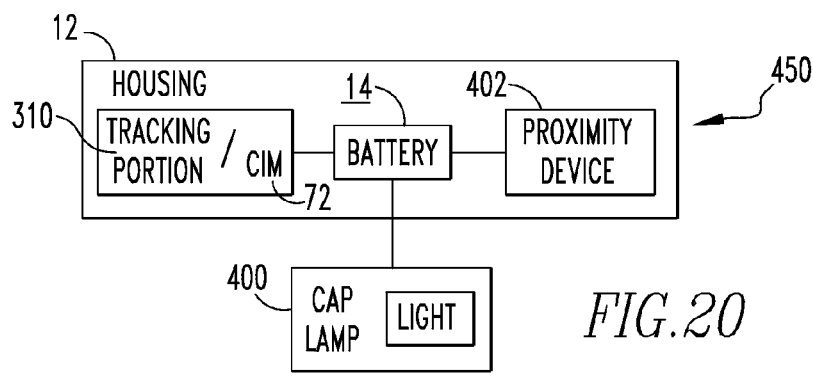
FIG. 20 is a block diagram of a miner apparatus with a cap lamp, proximity device and tracking.

The present invention pertains to a miner apparatus 450 of a wireless network, as shown in FIG. 20 and FIG. 21. The apparatus 450 comprises a housing 12 which is carried by the miner. The apparatus 450 comprises a tracking portion 310 disposed in the housing 12 which transmits information associated with the miner's location wirelessly to the network 66. The apparatus 450 comprises a battery 14 disposed in the housing 12 and connected to the tracking portion 310 which powers the tracking portion 310. The apparatus 450 comprises a proximity device electrically connected to the battery 14 and disposed in the housing 12 which is powered by the battery 14 to provide a detectable presence to a proximity detector when the miner gets too close to the proximity detector. The proximity device is worn by the miner. The apparatus 450 comprises a cap lamp 400 electrically connected to the battery 14 which is powered by the battery 14 to provide light. The cap lamp 400 is worn by the miner. Together these components of tracking, light and proximity are referred to as TPL.

The present invention pertains to a method for a miner to move through a mine. The method comprises the steps of powering a light of a cap lamp 400 on the miner's head with a battery 14 in a housing 12 carried by the miner. There is the step of sending information associated with location information of the miner's location in the mine from the housing 12 identified with a tracking portion 310 in the housing so the miner can be tracked as the miner moves through the mine. There is the step of stopping a machine with a proximity sensor connected to the machine, because the proximity sensor has sensed a proximity device in the housing 12 has come within a predetermined distance to the proximity device.

The following information may be contained in a message sent from the proximity detector 404. The message may include at least one byte regarding the health of a generator of the proximity detector 404. The message may include at least one byte that a miner has moved close enough to the proximity detector 404 that a warning has occurred. The message may include at least one byte that a miner has moved close enough to the proximity detector 404 that a hazard has occurred which has effectively stopped the operation of the machine associated with the proximity detector 404. The message may include at least one byte which identifies the magnetic field strength of a generator. The message may include at least one byte that identifies the ID of a proximity device 402, such as a personal alarm device (PAD), of a miner which has triggered a warning or hazard depending on how close the proximity device 402 is to the proximity detector 404. The message may include at least one byte which identifies the battery strength of the proximity device 402 which has triggered a warning or a hazard. The proximity device 402 and the proximity detector 404 themselves are sold by Strata Products Worldwide, LLC, Sandy Springs, Ga., USA. The PAD sends an ID signal to the proximity detector 404 so the proximity detector 404 knows the ID of the PAD that has caused a warning or a hazard which effectively turns the machine off.

The present invention pertains to a proximity detector 404 attached to a machine 475, as shown in FIG. 21. The detector 404 for detecting a miner's presence comprises a generator 477 which produces a magnetic field. The detector 404 comprises a processor 22. The detector 404 comprises a transceiver 48 for sending a message produced by the processor 22 having information about the generator's health and an ID of a PAD of a miner that has triggered a warning or hazard that has effectively stopped operation of the machine 475.

Preferably, the tracking portion 310 is a CIM 72 and the wireless network 66 is the CommTrac network 66. In one embodiment the CIM 72 and the battery 14 are in the housing 12 and the housing 12 is attached to the cap lamp 400 with wiring extending from the housing 12 to the lamp through a socket in the cap to power the lamp. In another embodiment, the housing 12 is positioned in a pocket or on a belt held with a buckle of the miner, and wiring extends from the battery 14 through the housing 12 up to the back of the cap lamp 400 and attached to a socket of the cap to power the lamp. The cap may be a standard miner helmet modified to have the socket to receive the power wire from the battery IA in the housing 12.

In an alternative embodiment, the CIM 72 and the battery 14 are disposed in the housing 12 along with a proximity device 402. The battery 14 powers the CIM 72 and the proximity device 402 so that proximity detection and tracking of the miner are located in the housing 12 which is carried by the miner.

In yet another embodiment, the CIM 72, the battery 14 and the proximity device 402 are all disposed in the housing 12, with the battery 14 powering the CIM 72 and the proximity device 402. In addition, wiring extending from the battery 14 and out through the housing 12 to the back of a cap lamp 400 worn by a miner to power the lamp.

Figure 23A:
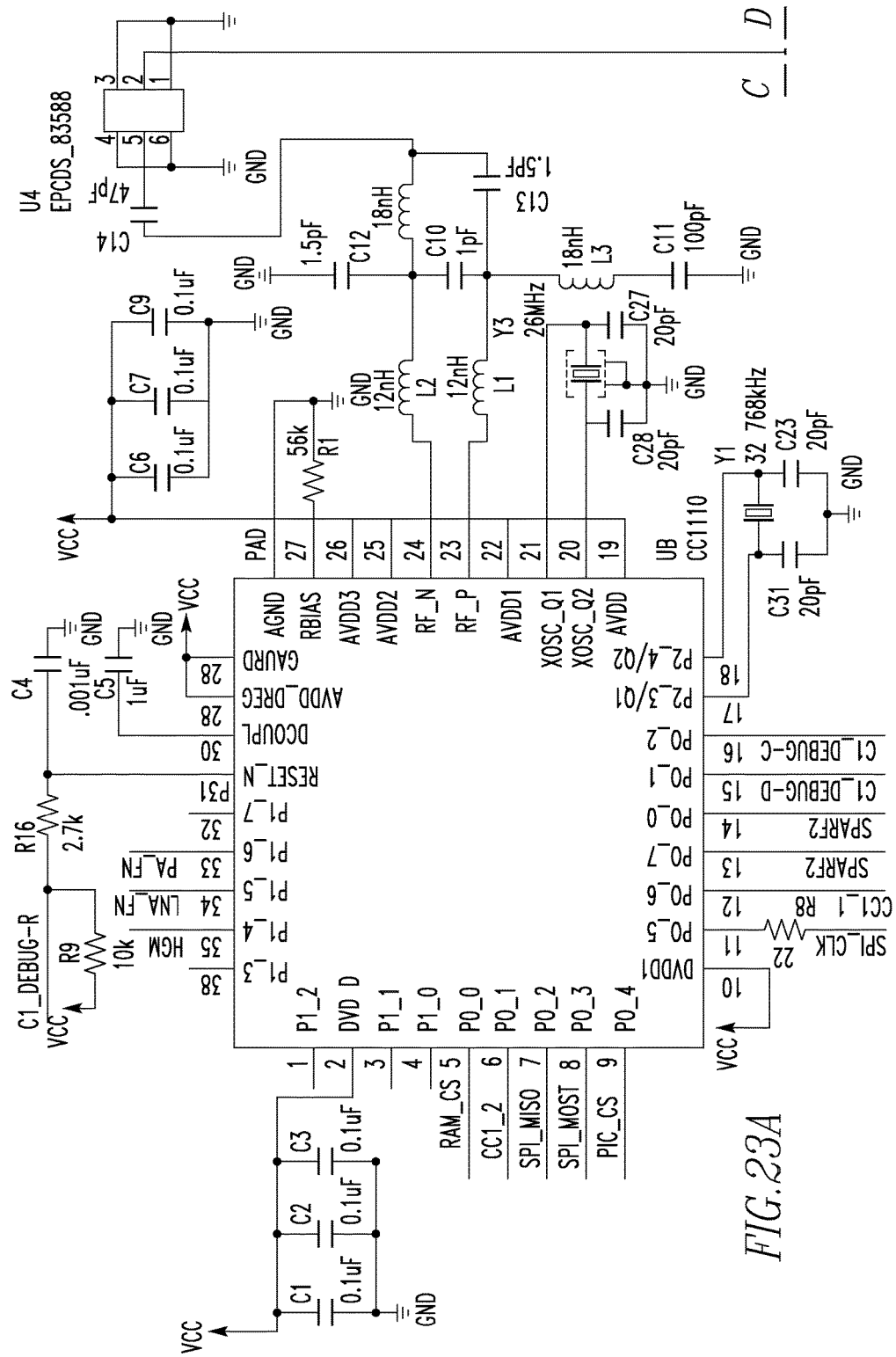
Figure 23B:
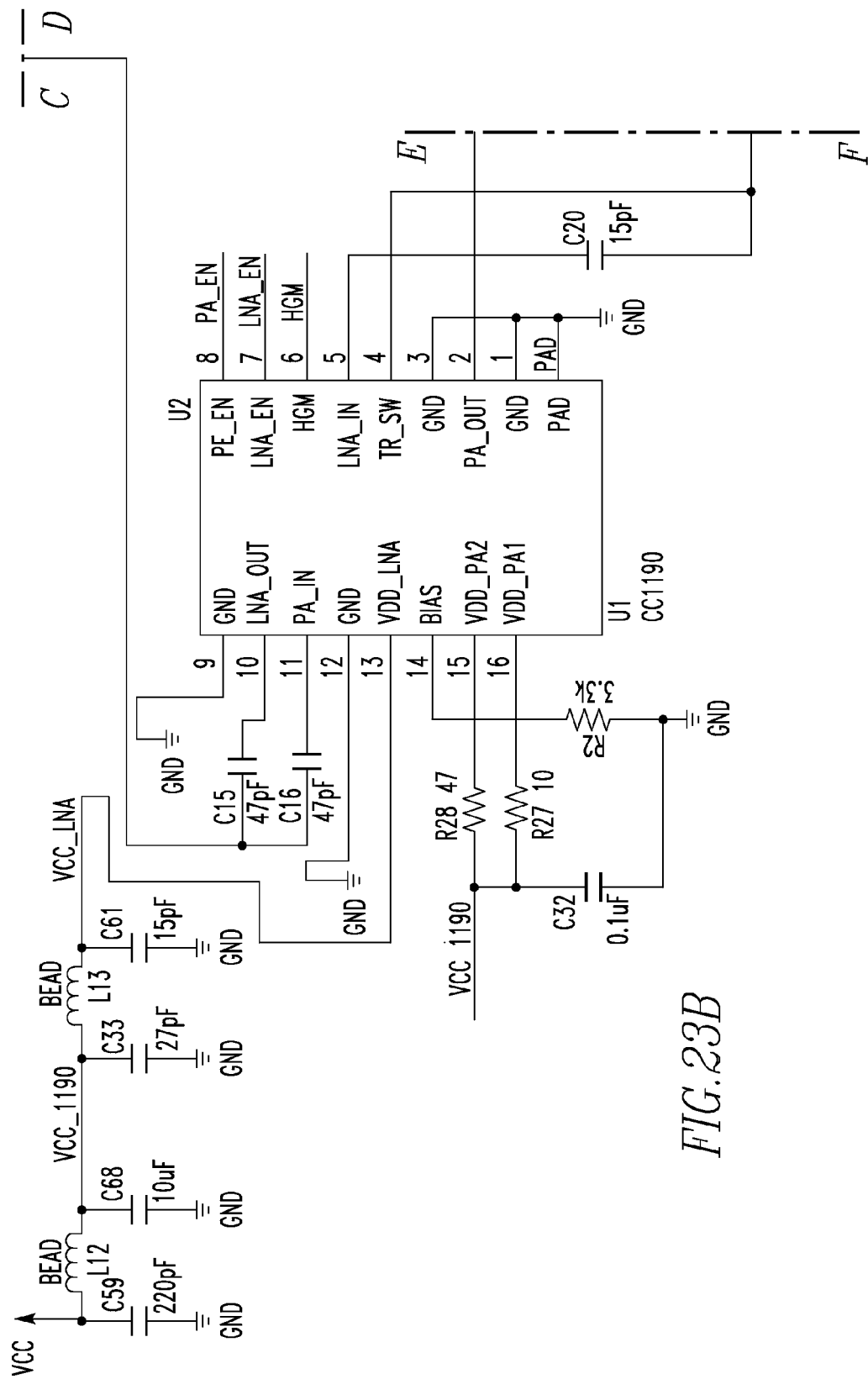
Figure 24:
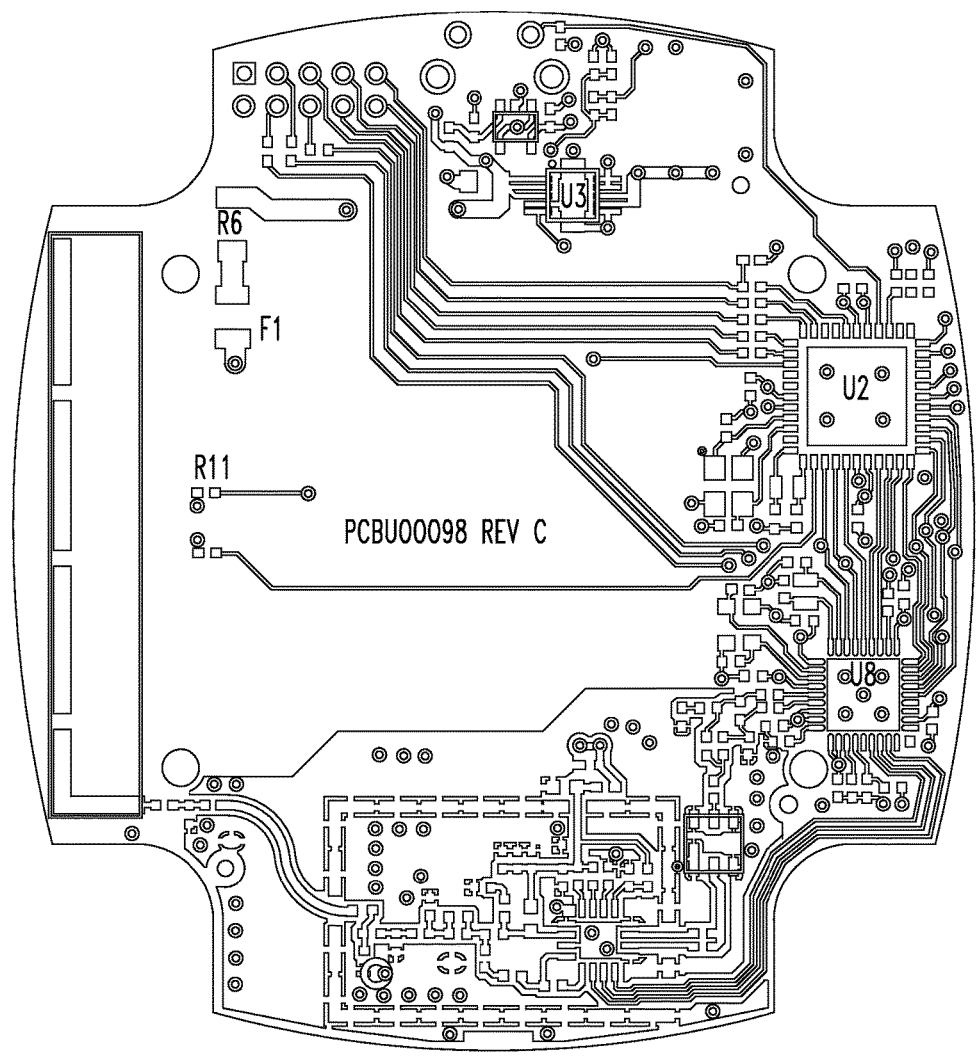
FIG. 24 shows an overhead view of the circuit board having the circuitry described in FIGS. 22A-23E.
Figure 25A:
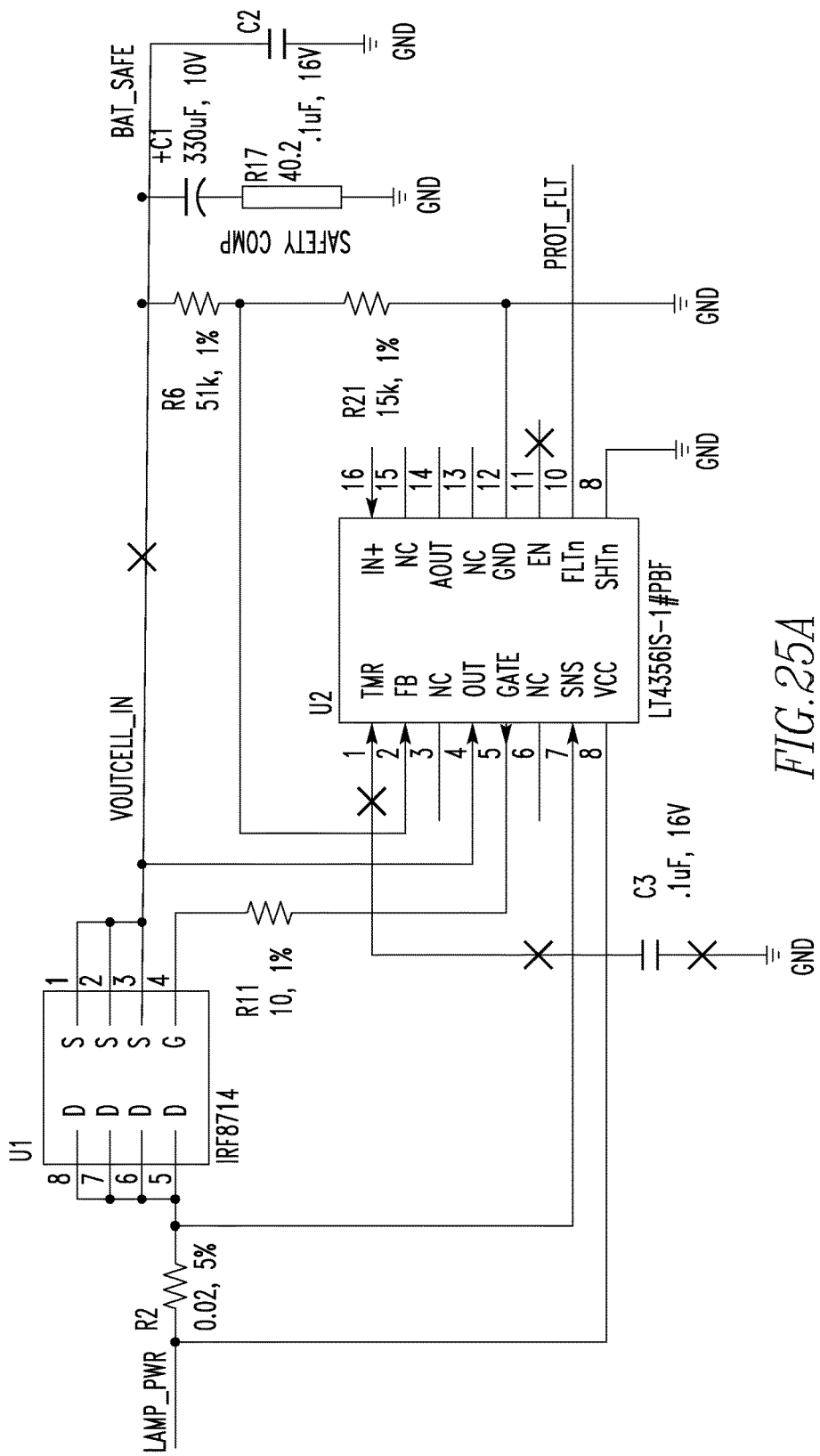
FIGS. 25A-25J, 26A-26F, 27A-27L, 28A and 28B are circuit diagrams of the miner apparatus of the present invention.
Figure 25B:
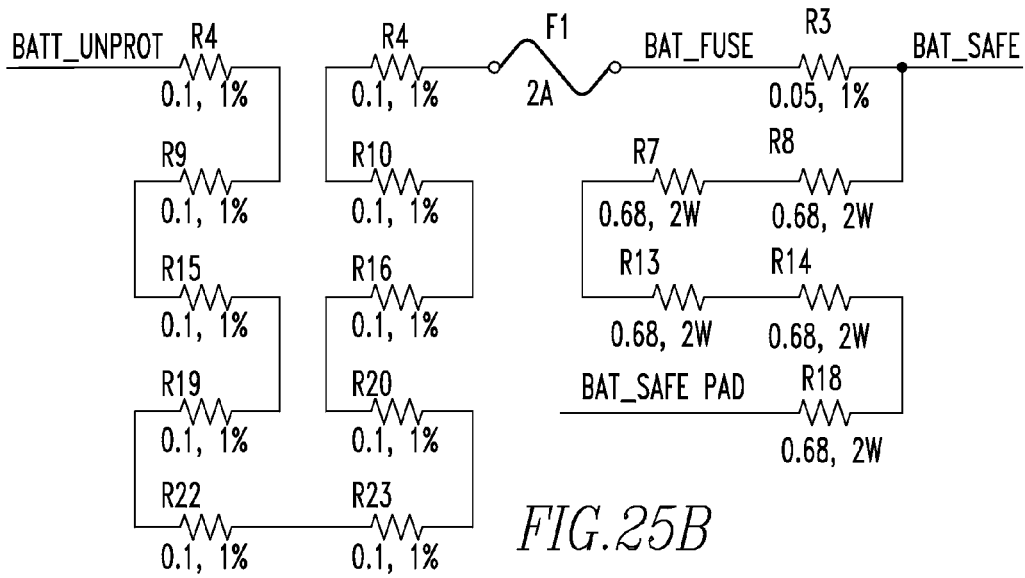
Figure 25C:
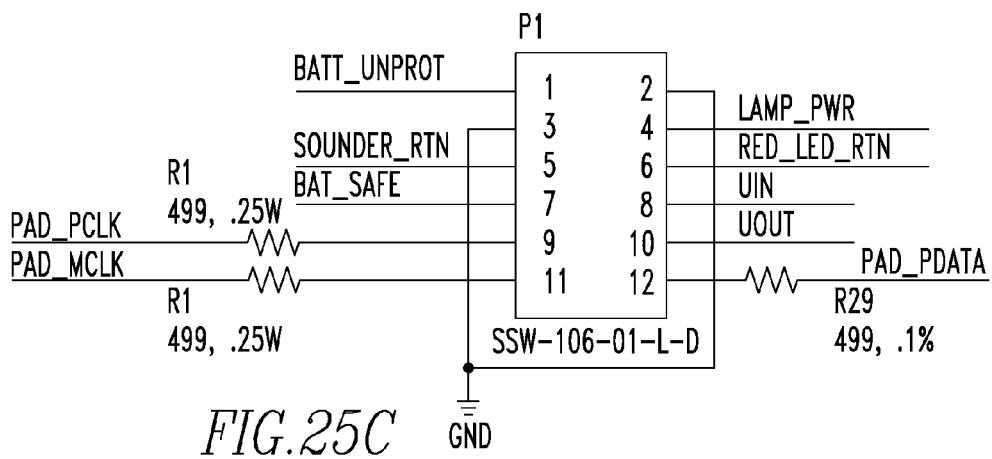
Figure 25D:
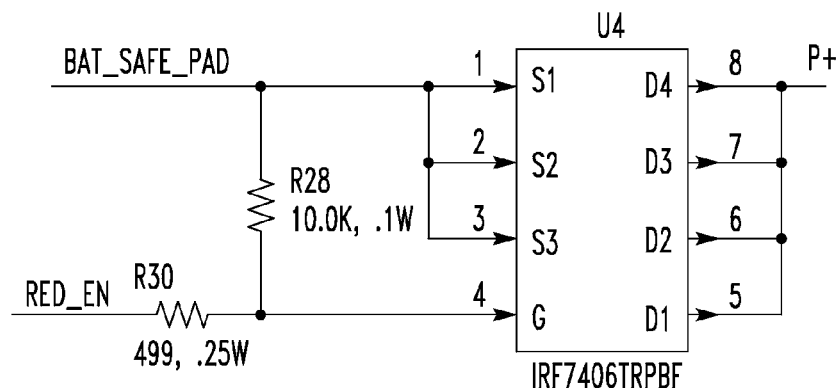
Figure 25E:
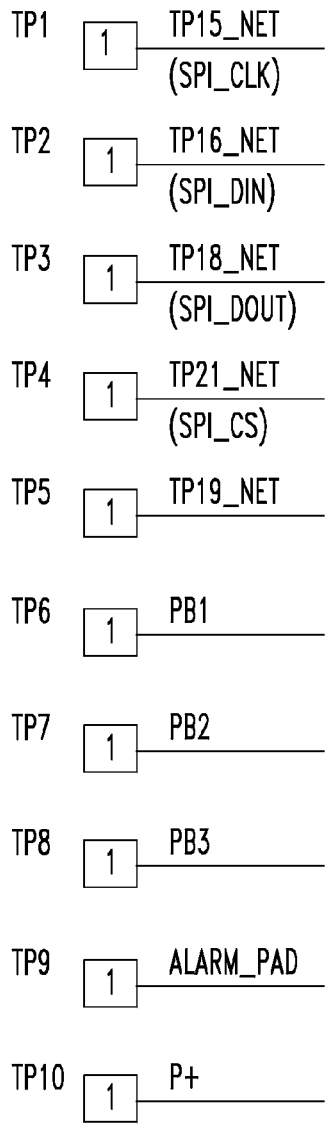
Figure 25F:
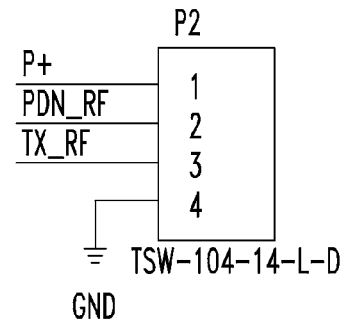
Figure 25G:
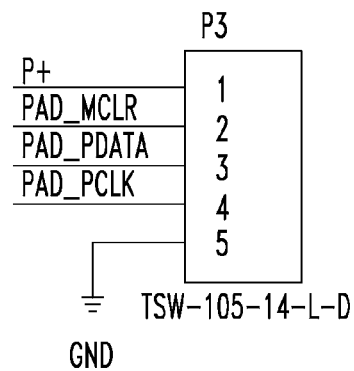
Figure 25H:
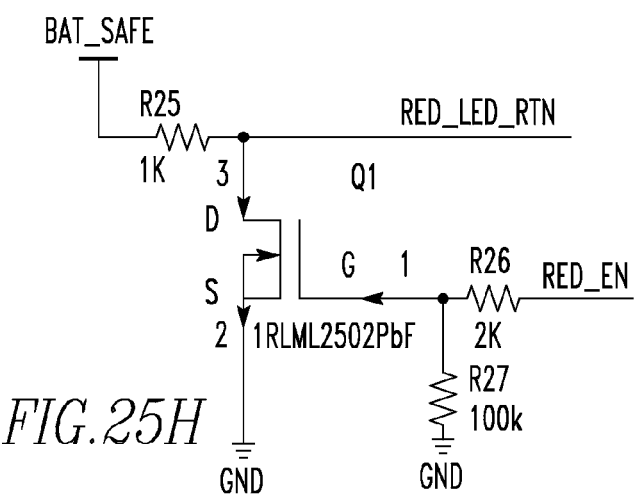
Figure 25I:
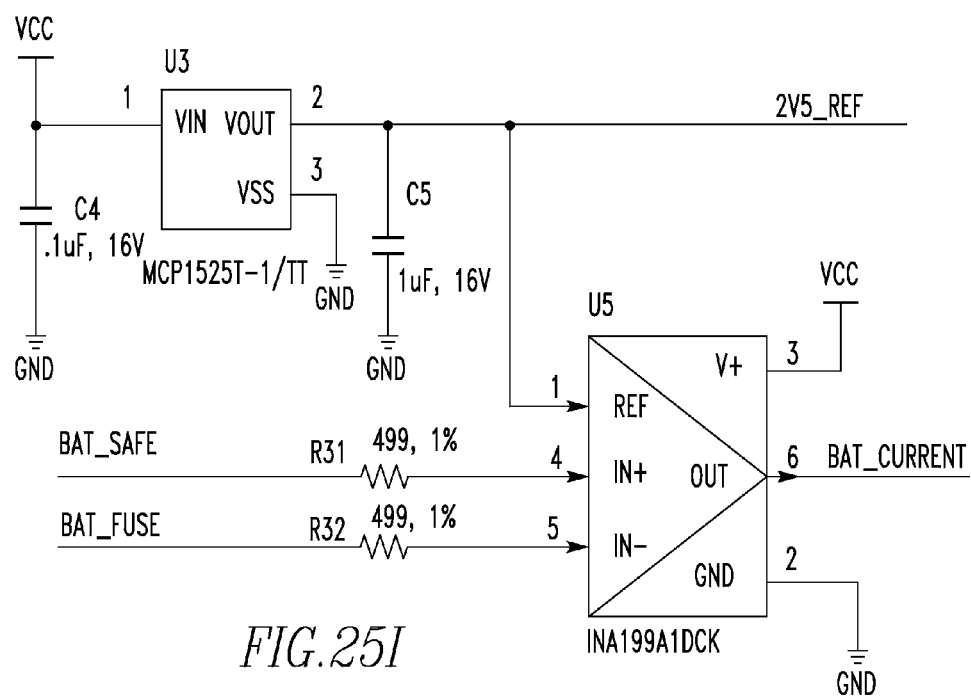
Figure 25J:
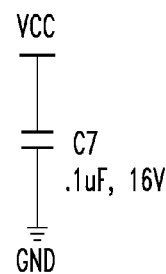
Figure 26A:
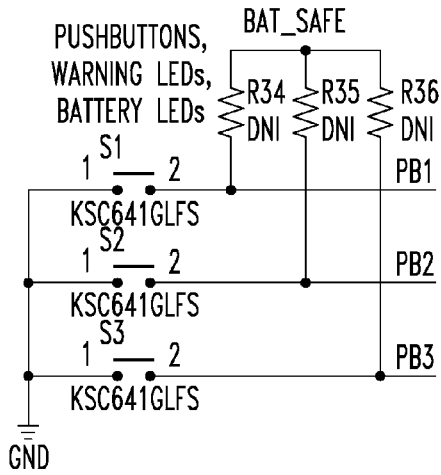
Figure 26B:
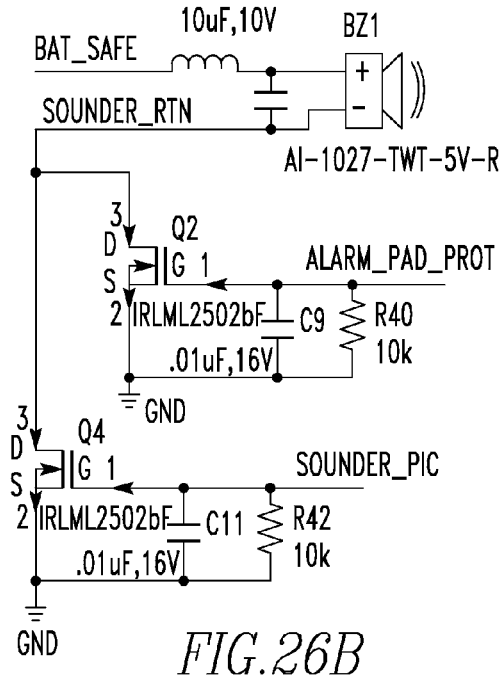
Figure 26C:
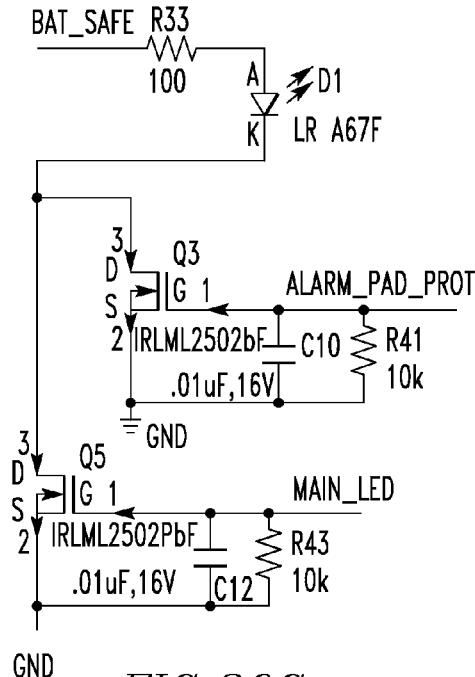
Figure 26D:
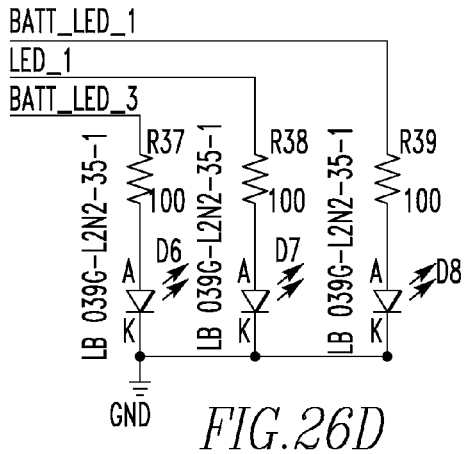
Figure 26E:
Figure 26F:
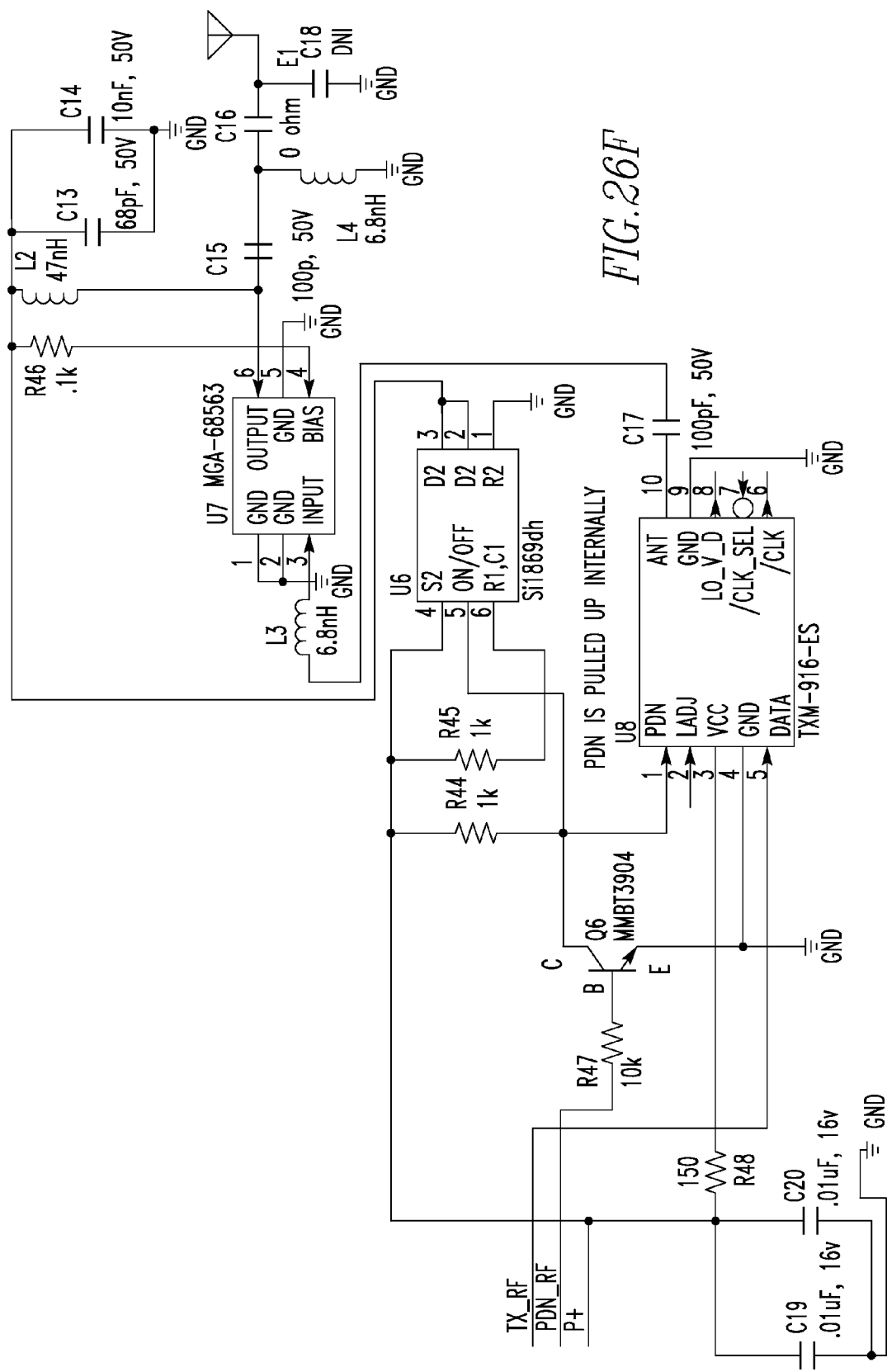
Figure 27A:
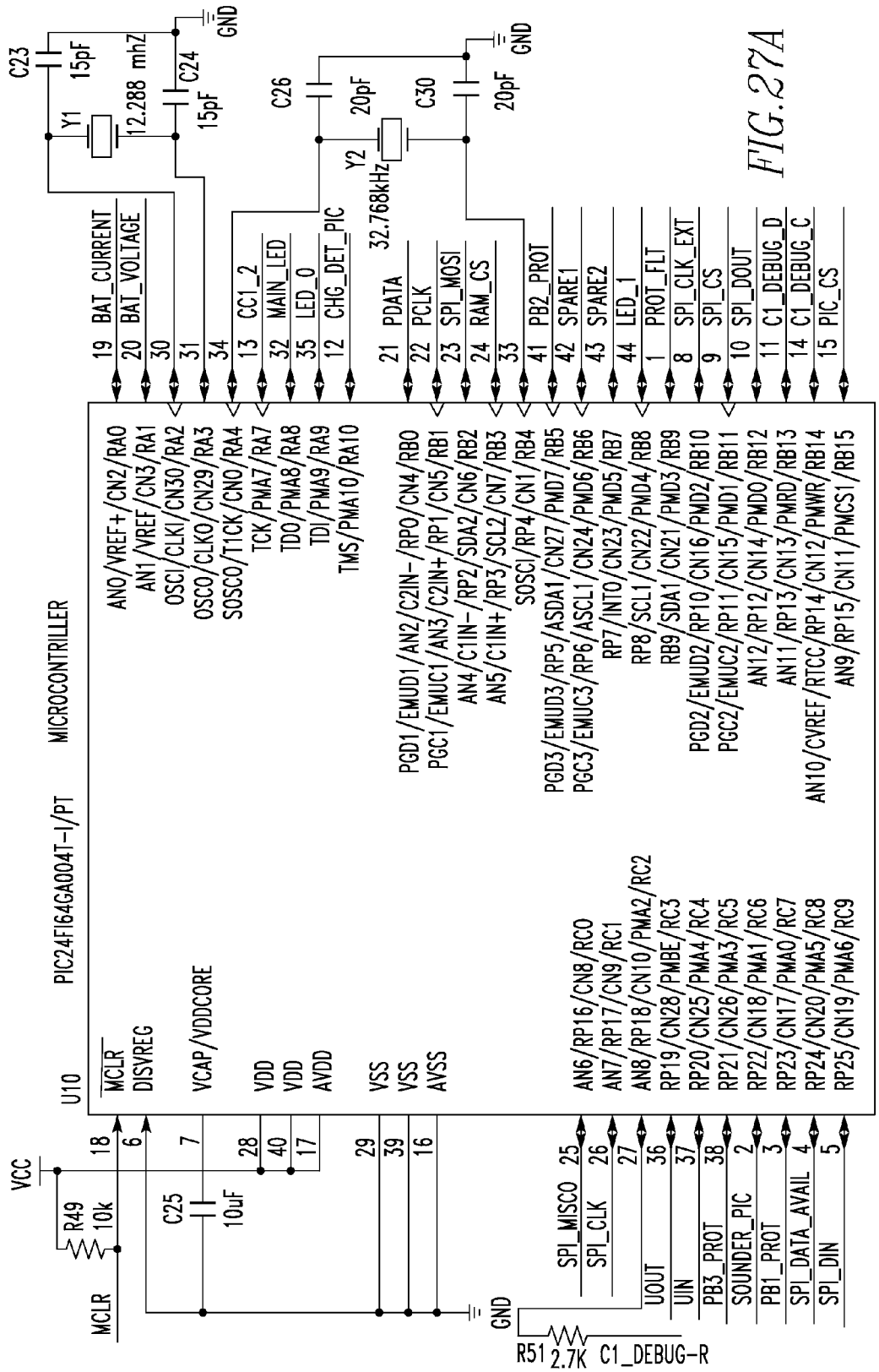
Figure 27B:
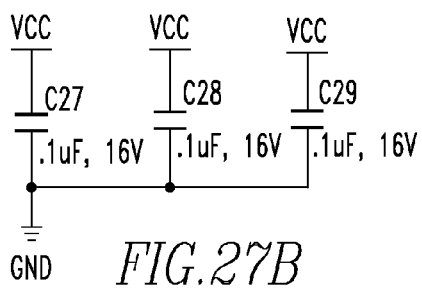
Figure 27C:
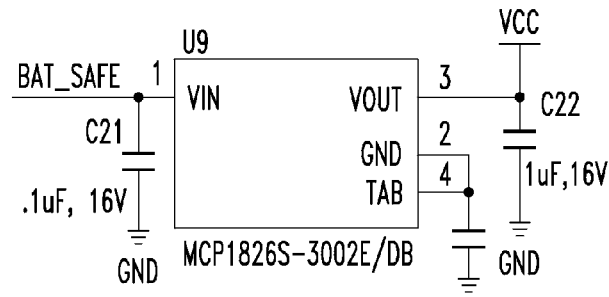
Figure 27D:
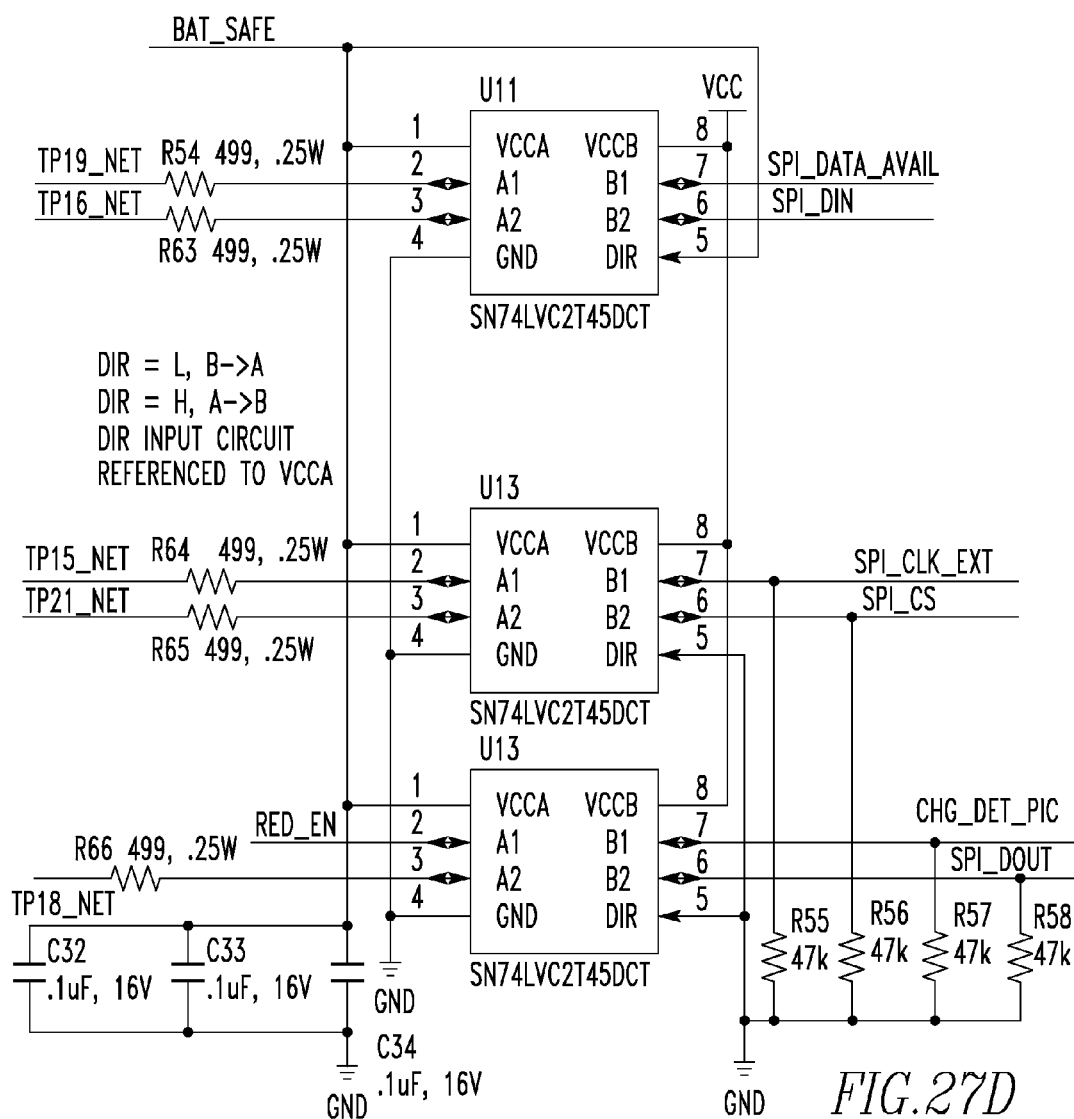
Figure 27E:
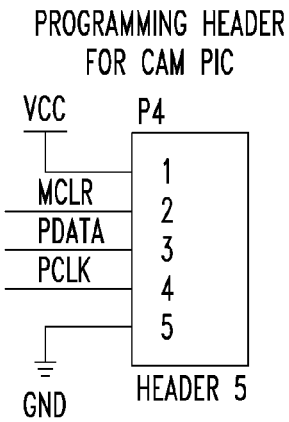
Figure 27F:
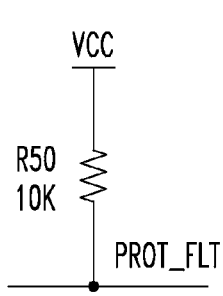
Figure 27G:
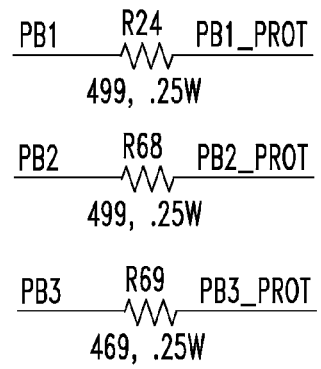
Figure 27H:
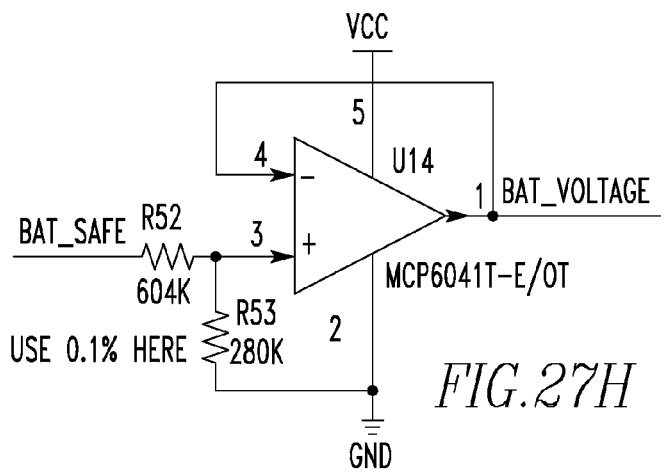
Figure 27I:
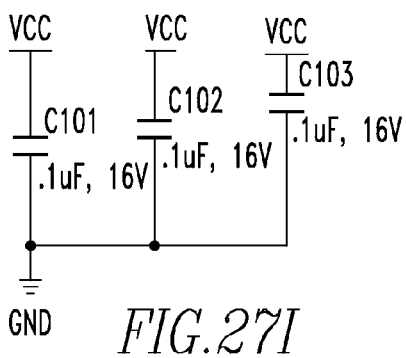
Figure 27J:
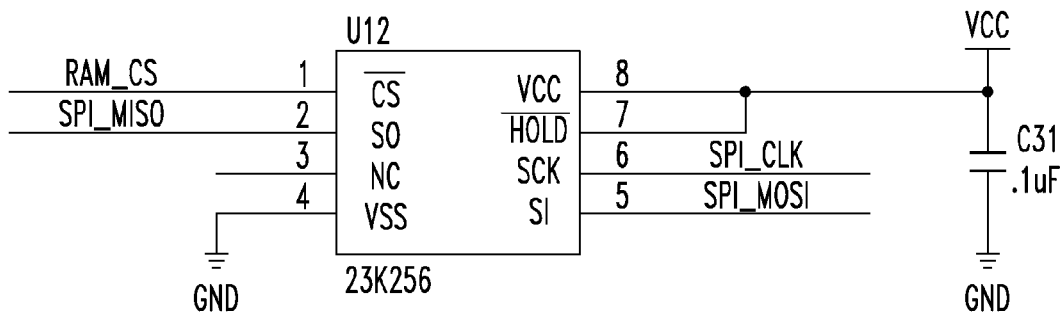
Figure 27K:
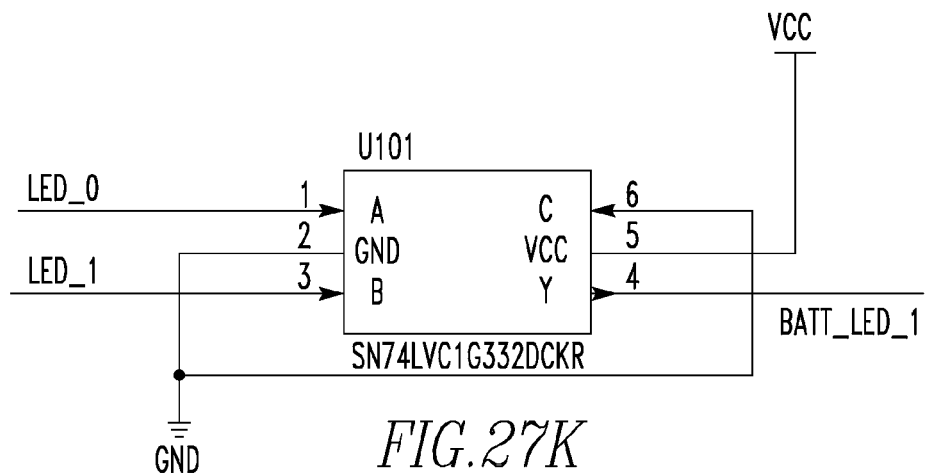
Figure 27L:
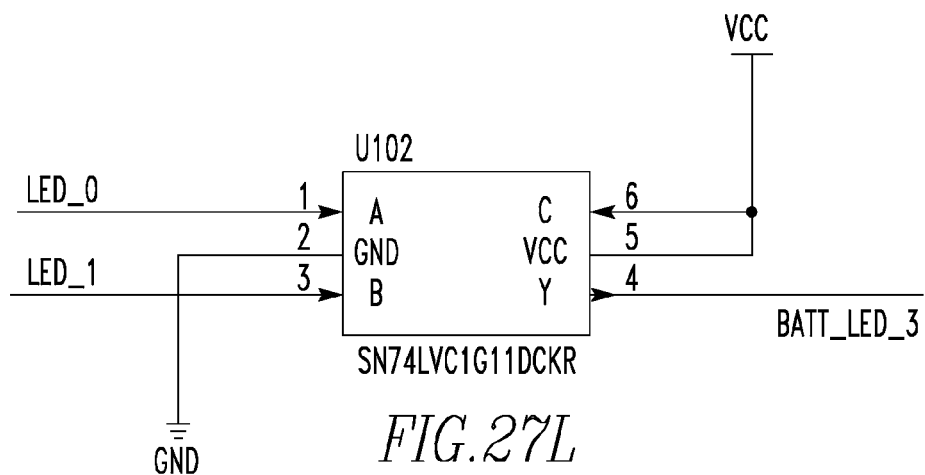
Figure 28A:
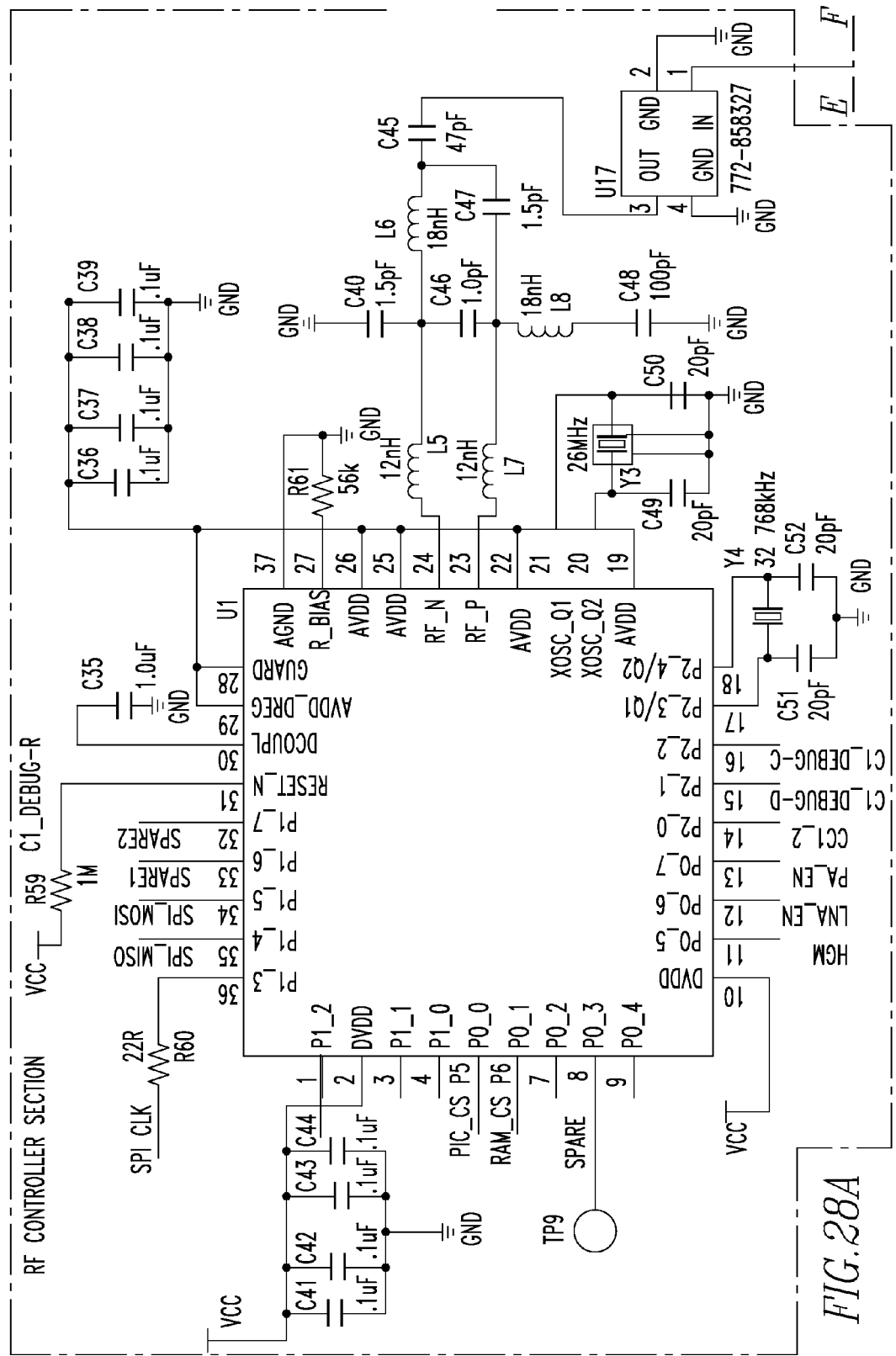
Figure 28B:
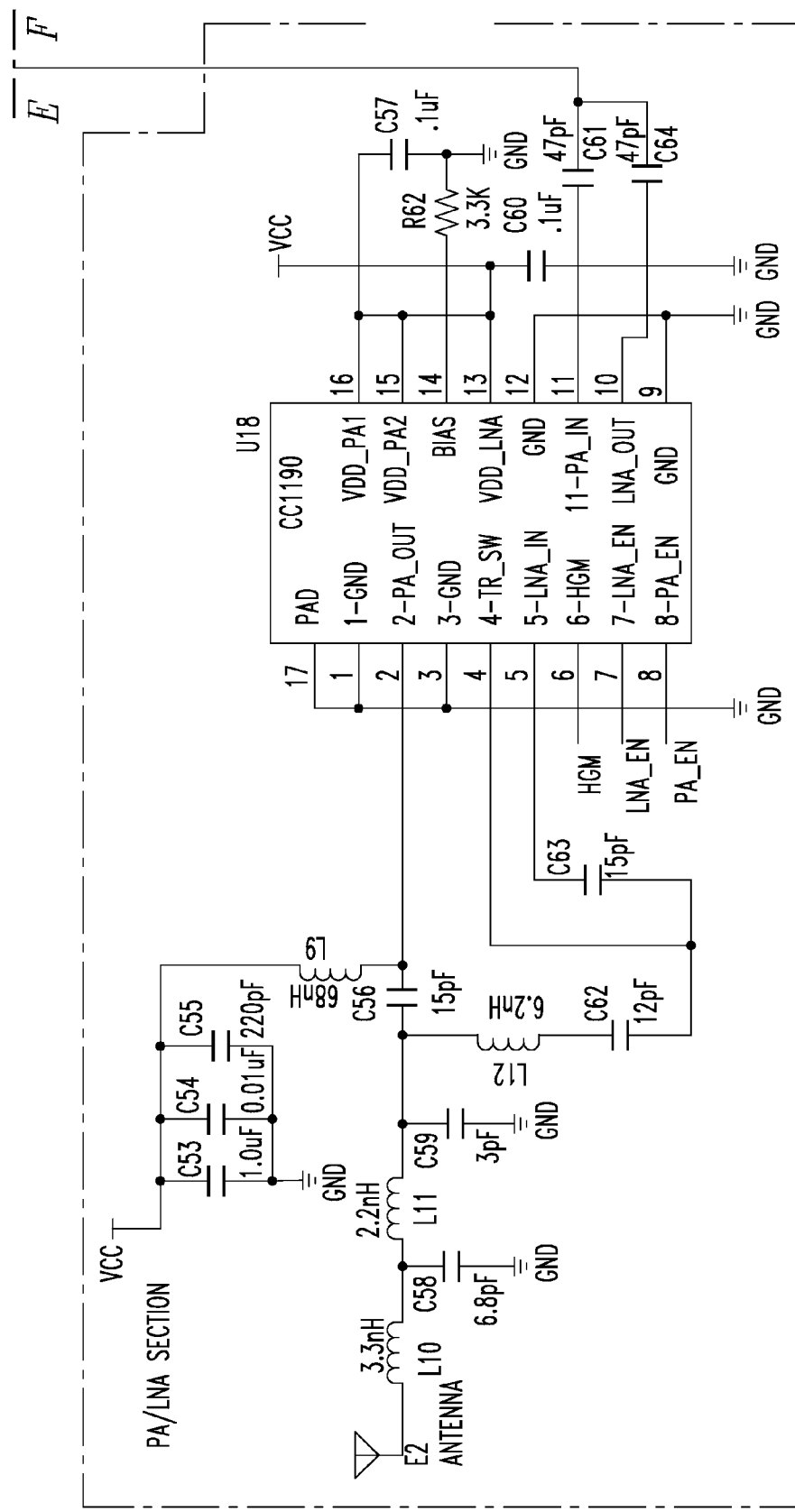

With reference to FIGS. 22A-22K and 23A-23E that are schematic circuit diagrams for the miner communicator 298, the following is a parts list for the communicator 298. The operation of the processor 22 and transceiver 48, that form the CIM 72 is the same, but there is additional circuitry for the features of the communicator 298. All of the following parts are themselves alone well-known and are identifiable by their part number, description and manufacturer. FIG. 24 shows an overhead view of the circuit board having the circuitry described in FIGS. 22 and 23.

| LineItem | Reference Designator | Quantity | Manufacturer | Part Number | Description |
|---|---|---|---|---|---|
| 1 | C1, C2, C3, C6, C7, C9, C32, C35, C36, C37, C38, C39 | 12 | Taiyo Yuden | EMK105B7104KV-F | CAP CER 0.1UF 16 V 10% X7R 0402 |
| 2 | C4, C18 | 2 | TDK Corporation | CGA2B2X7R1H102K050BA | CAP CER 1000PF 50 V 10% X7R 0402 |
| 3 | C5, C19 | 2 | TDK Corporation | C1005X5R1C105K050BC | CAP CHR 1UF 16 V 10% X5R 0402 |
|  | C8, C52, L14 | 3 | Panasonic Electronic Components | ERJ-2GE0R00X | RES 0.0 OHM 1/10 W JUMP 0402 SMD |
| 4 | C10 | 1 | TDK Corporation | C1005C0G111010C050BA | CAP CER 1PF 50 V NP0 0402 |
| 5 | C11 | 1 | TDK Corporation | C1005C0G1H101J050BA | CAP CER 100PF 50 V 5% NP0 0402 |
| 6 | C12, C13 | 2 | TDK Corporation | C1005C0G1H1R5B050BA | CAP CER 1.5PF 50 V NP0 0402 |
| 7 | C14, C15, C16 | 3 | TDK Corporation | C1005C0G1H470J050BA | CAP CER 47PF 50 V 5% NP0 0402 |
| 8 | C17 | 1 | Johanson Dielectrics Inc | 250R07N221JV4T | CAP CER 220PF 25 V 5% NP0 0402 |
| 10 | C20, C21, C45, C61 | 4 | TDK Corporation | C1005NP01H150J050BA | CAP CER 15PF 50 V 5% NP0 0402 |
| 11 | C22 | 1 | Johanson Dielectrics Inc | 500R07S120GV4T | CAP CER 12PF 50 V 2% NP0 0402 |
| 12 | C23, C27, C28, C31, C40, C41 | 6 | Murata Electronics North America | GRM1555C1H200GA01D | CAP CER 20PF 50 V 2% NP0 0402 |
| 13 | C24 | 1 | TDK Corporation | C1005C0G1H030C050BA | CAP CER 3PF 50 V NP0 0402 |
| 14 | C25, C51 | 2 | TDK Corporation | CGA2B2C0G1H6R8D050BA | CAP CER 6.8PF 50 V NP0 0402 |
| 15 | C26, C29, C30 | 3 | TDK Corporation | C1005C0G1H330J050BA | CAP CER 33PF 50 V 5% NP0 0402 |
|  | C33 | 1 | TDK Corporation | C1005C0G1H270J050BA | CAP CER 27PF 50 V 5% NP0 0402 |
| 16 | C34 | 1 | Taiyo Yuden | UMK105CG181JV-F | CAP CER 180PF 50 V 5% NP0 0402 |
| 17 | C42, C43, C44, C60 | 4 | TDK Corporation | C1608X5R1A106M080AC | CAP CER 10UF 10 V 20% X5R 0603 |

-continued

| LineItem | Reference Designator | Quantity | Manufacturer | Part Number | Description |
|---|---|---|---|---|---|
| 18 | C46, C49 | 0 | | DNP | |
| 19 | C47, C48, C50 | 3 | TDK Corporation | C2012X5R1A226M085AC | CAP CER 22UF 10 V 20% X5R 0805 0.95 MM THICK |
| | C59 | 1 | TDK Corporation | C1005C0G1H221J050BA | CAP CER 220PF 50 V 5% NP0 0402 |
| 20 | D1, D2 | 2 | Avago Technologies US Inc. | HSMZ-C170 | LED CHIP ALINGAP2 RED TOP MOUNT 0805 |
| 21 | D4, D5, D6 | 3 | Diodes | B0520WS-7-F | DIODE SCHOTTKY 20 V 0.5 A SOD323 |
| 22 | E1 | 1 | Vishay | VJ5301M915MXBSR | RF ANTENNA, 915 MHz |
| 23 | F1 | 1 | Littelfuse | 0466.500NR | FUSE .500 A 63 V FAST 1206 |
| | H1 | 1 | Tech-Etch | | EMI Shield 0.500 in. × 0.800 in. × 0.060 in. |
| 24 | J3 | 1 | Samtec | MTMM-105-05-F-D-250 | |
| 25 | L1, L2 | 2 | TDK Corporation | MLG1005S12NJ | INDUCTOR MULTILAYER 12NH 0402 |
| 26 | L3, L4 | 2 | TDK Corporation | MLG1005S18NJ | INDUCTOR MULTILAYER 18NH 0402 |
| 27 | L5 | 1 | Coilcraft | 0603HP-68NXJLU | INDUCTOR WIREWOUND 68NH 0603 5% |
| 28 | L6 | 1 | TDK Corporation | MHQ1005P6N2S | INDUCTOR MULTILAYER 6.2NH 0402 |
| 29 | L7 | 1 | TDK Corporation | MHQ1005P2N2S | INDUCTOR MULTILAYER 2.2NH 0402 |
| 30 | L8, L11 | 2 | TDK Corporation | MHQ1005P3N3S | INDUCTOR MULTILAYER 3.3NH 0402 |
| 31 | L9 | 1 | Taiyo Yuden | NR6045T6R3M | INDUCTOR 6.3UH 3.8 A 20% SMD |
| 32 | L10 | 1 | | DNP | |
| | L12, L13 | 2 | Murata Electronics North America | BLM15HG102SN1D | FILTER CHIP 1000 OHM 250 MA 0402 |
| | L15 | 1 | | DNP | |
| 34 | P1, P2, P3, P4, P5, P6 | 6 | Keystone | 56 | BATTERY CLIP AAA SMD |
| 35 | R1 | 1 | Panasonic Electronic Components | ERJ-2RKF5602X | RES 56K OHM 1/10 W 1% 0402 SMD |
| 36 | R2 | 1 | Panasonic Electronic Components | ERJ-2GEJ332X | RES 3.3K OHM 1/10 W 5% 0402 SMD |
| 37 | R3 | 1 | Panasonic Electronic Components | ERJ-2RKF4993X | RES 499K OHM 1/10 W 1% 0402 SMD |
| 38 | R4, R12 | 2 | Panasonic Electronic Components | ERJ-2RKF1133X | RES 113K OHM 1/10 W 1% 0402 SMD |
| 39 | R5, R7, R9, R29 | 4 | Panasonic Electronic Components | ERJ-2RKF1002X | RES 10K OHM 1/10 W 1% 0402 SMD |
| 40 | R6 | 1 | Panasonic Electronic Components | ERJ-8GEY0R00V | RES 0.0 OHM 1/4 W JUMP 1206 SMD |
| 41 | R8 | 1 | Yageo | RC0402FR-0722RL | RES 22.0 OHM 1/16 W 1% 0402 SMD |
| 42 | R10, R16 | 2 | Panasonic Electronic Components | ERJ-2RKF2701X | RES 2.7K OHM 1/10 W 1% 0402 SMD |
| 43 | R11 | 1 | Panasonic Electronic Components | ERJ-2RKF51R0X | RES 51 OHM 1/10 W 1% 0402 SMD |
| 44 | R13 | 1 | Panasonic Electronic Components | ERJ-2RKF1004X | R1ZS 1M OHM 1/10 W 1% 0402 SMD |
| | R14, R15 | 2 | Panasonic Electronic Components | ERJ-2RKF24R9X | RES 24.9 OHM 1/10 W 1% 0402 SMD |
| 45 | R17, R18, R19, R22, R23, R24, R25, R26 | 8 | Panasonic Electronic Components | ERJ-2RKF1001X | RES 1K OHM 1/10 W 1% 0402 SMD |
| 46 | R20 | 1 | Panasonic Electronic Components | ERJ-2RKF2003X | RES 200K OHM 1/10 W 1% 0402 SM |

| LineItem | Reference Designator | Quantity | Manufacturer | Part Number | Description |
|---|---|---|---|---|---|
| 47 | R21 | 1 | Panasonic Electronic Components | ERJ-2RKF6043X | RES 604K OHM 1/10 W 1% 0402 SMD |
|  | R27 | 1 | Panasonic Electronic Components | ERJ-2RKF10R0X | RES 10 OHM 1/10 W 1% 0402 SMD |
|  | R28 | 1 | Panasonic Electronic Components | ERJ-2RKF47R0X | RES 47 OHM 1/10 W 1% 0402 SMD |
| 48 | S4 | 1 | Coto Technology | CT05-1535-G1 | REED SWITCH MOLDED 140 V 15-35 AT |
| 49 | S2 | 1 | C&K Components | PTS645VH39-2 LFS | SWITCH TACTILE SPST-NO 0.05 A 12 V |
| 50 | S3 | 1 | SignalQuest | SQ-MIN-200 | SQ-MIN-200 |
| 51 | U1 | 1 | Texas Instruments | CC1190RGVT | IC RF FRONT-END 16 VQFN |
| 52 | U2 | 1 | Microchip | P1C24FJ64GA004-1/ML | IC MCU 16 BIT 64 KB FLASH 44QFN |
| 53 | U3 | 1 | Texas Instruments | TPS62040DGQR | IC REG BUCK SYNC ADJ 1.2 A 10MSOP |
| 54 | U4 | 1 | Epcos | B39921B3588U410 | Signal Conditioning 915 MHz 50 ohms 2.9 dB |
| 55 | U6 | 1 | Microchip | MCP6041T-I/OT | IC OPAMP GP 14 KHZ RRO SOT23-5 |
| 56 | U7 | 1 | Microchip | 23K256-I/ST | IC SRAM 256 KBIT 20 MHZ 8TSSOP |
| 57 | U8 | 1 | Texas Instruments | CC1110F32RHHT | IC SOC RF TXRX W/8051 MCU 36-VQF |
| 58 | Y1, Y4 | 2 | Abracon | ABS06-32.768KHZ-T | CRYSTAL 32.768 KHZ 12.5PF SMD |
| 59 | Y2 | 1 | TXC | 7M-12.288MAAJ-T | CRYSTAL 12.288 MHZ 18PF SMD |
| 60 | Y3 | 1 | CTS | 403C11A26M00000 | CRYSTAL 26 MHZ 10PF SMD |
|  | PCB | 1 | Strata Products Worldwide | PCBU000098 Rev C |  |

With reference to FIGS. 25A-25J, 26A-26F, 27A-27L, 28A and 28B, which are schematic circuit diagrams for the miner apparatus 450, the following is a parts list for the miner apparatus 450. The operation of the processor 22 and transceiver 48, that form the CIM 72 is the same, but there is additional circuitry for the features of the miner apparatus 450. All of the following parts are themselves alone are well known and are identifiable by their part number, description and manufacturer.

| Line Item | Designator | Quantity | Manufacturer | Part Number | Description |
|---|---|---|---|---|---|
| 1 | BZ1 | 1 | PUI AUDIO | A1-1027-TWT-5V-R | BUZZER MAGN 5 VDC 2.7 KHZ PCB |
| 2 | C1 | 1 | Kemet | T495D337K010ATE150 | CAP TANT 330UF 10 V 10% 2917 |
| 3 | C2, C3, C4, C7, C20, C21, C27, C28, C29, C32, C33, C34, C36, C37, C38, C39, C41, C42, C43, C44, C101, C102, C103 | 23 | Panasonic | C0603C104K4RACTU | CAP CER 0.1UF 16 V 10% X7R 0603 |
| 4 | C8 | 1 | Samsung Electro-Mechanics America | CL21B106KOQNNNE | CAP CER 10UF 16 V 10% X7R 0805 |
| 5 | C9, C10, C11, C12, C19 | 5 | Panasonic | C0603C103K4RACTU | CAP CER 0.1UF 16 V 10% X7R 0603 |
| 6 | C13 | 1 | TDK Corporation | C1005C0G1H680J050BA | CAP CER 68PF 50 V 5% NP0 0402 |
| 7 | C14 | 1 | TDK Corporation | C1005X7R1H103K050BB | CAP CER 10000PF 50 V 10% X7R 0402 |
| 8 | C15, C17, C48 | 3 | TDK Corporation | C1005C0G1H101J050BA | CAP CER 100PF 50 V 5% NP0 0402 |

-continued

| Line Item | Designator | Quantity | Manufacturer | Part Number | Description |
|---|---|---|---|---|---|
| 9 | C16 | 1 | Panasonic | ERJ-2GE0R00X | JUMPER 0 OHM 1/10 W 0402 SMD |
| 10 | C18, R34, R35, R36, TP9 | 5 | | | DO NOT INSTALL |
| 11 | C5, C22 | 2 | Kemet | C0603C105K4RACTU | CAP CER 1UF 16 V 10% X7R 0603 |
| 12 | C23, C24, C56, C63 | 4 | TDK Corporation | C1005NP01H150J050BA | CAP CER 15PF 50 V 5% NP0 0402 |
| 13 | C25 | 1 | TDK Corporation | C1608X5R1E106M080AC | CAP CER 10UF 25 V 20% X5R 0603 |
| 14 | C26, C30, C49, C50, C51, C52 | 6 | Kemet | CBR04C200F5GAC | CAP CER 20PF 50 V 1% NP0 0402 |
| 15 | C31, C57, C60 | 3 | TDK Corporation | C1005X5R1A104K050BA | CAP CER 0.1UF 10 V 10% X5R 0402 |
| 16 | C35, C53 | 2 | TDK Corporation | C1005X5R1C105K050BC | CAP CER 1UF 16 V 10% X5R0402 |
| 17 | C40, C47 | 2 | TDK Corporation | C1005C0G1H1R5B050BA | CAP CER 1.5PF 50 V ± 0.1PF NP0 0402 |
| 18 | C45, C61, C64 | 3 | TDK Corporation | C1005C0G1H470J050BA | CAP CER 47PF 50 V 5% NP0 0402 |
| 19 | C46 | 1 | TDK Corporation | C1005C0G1H010C050BA | CAP CER 1PF 50 V ± 0.25PF NP0 0402 |
| 20 | C54 | 1 | TDK Corporation | C1005X7R1C103K050BA | CAP CER 10000PF 16 V 10% X7R 0402 |
| 21 | C55 | 1 | Johanson Dielectrics Inc | 250R07N221JV4T | CAP CER 220PF 25 V 5% NP0 0402 |
| 22 | C58 | 1 | TDK Corporation | CGA2B2C0G1H6R8D050BA | CAP CER 6.8PF 50 V NP0 0402 |
| 23 | C59 | 1 | TDK Corporation | CGJ2B2C0G1H030C050BA | CAP CER 3PF 50 V NP0 0402 |
| 24 | C62 | 1 | Johanson Technology Inc | 500R07S120GV4T | CAP CER 12PF 50 V 5% NP0 0402 |
| 25 | D1 | 1 | OSRAM Opto Semiconductors | LR A67F-U2AB-1-7 | LED SIDELED RED 625 NM CLR RA SMD |
| 26 | D6, D7, D8 | 3 | OSRAM Opto Semiconductors | LB Q39G-L2N2-35-1 | LED CHIPLED BLUE 470 NM 0603 SMD |
| 27 | E1, E2 | 2 | Pulse Electronics Corporation | W3113, W3114 | |
| 28 | F1 | 1 | Littelfuse | 0466002.NR | FUSE 2 A 63 V FAST 1206 |
| 29 | L1 | 1 | Panasonic | ELL-6RH8R2M | COIL 8.2UH 1200 MA CHOKE SMD |
| 30 | L2 | 1 | TDK Corporation | MLG1005S47NJT000 | INDUCTOR MULTILAYER 47NH 0402 |
| 31 | L3, L4 | 2 | TDK Corporation | MLG1005S6N8JT000 | INDUCTOR MULTILAYER 6.8NH 0402 |
| 32 | L5, L7 | 2 | TDK Corporation | MLG1005S12NJ | INDUCTOR MULTILAYER 12NH 0402 |
| 33 | L6, L8 | 2 | TDK Corporation | MLG1005S18NJ | INDUCTOR MULTILAYER 18NH 0402 |
| 34 | L9 | 1 | Pulse Electronics Corporation | PE-0603CD680JTT | INDUCTOR WW RF 68NH 600 MA 0603 |
| 35 | L10 | 1 | TDK Corporation | MLG1005S3N3S | INDUCTOR MULTILAYER 3.3NH 0402 |
| 36 | L11 | 1 | TDK Corporation | MLK1005S2N2S | INDUCTOR MULTILAYER 2.2NH 0402 |
| 37 | L12 | 1 | TDK Corporation | MLG1005S6N2S | INDUCTOR MULTILAYER 6.2NH 0402 |
| 38 | P1 | 1 | Samtec | SSW-106-01-L-D | Header, 6-Pin, Dual row |
| 39 | P2 | 1 | Samtec | TSW-104-06-L-S | Header, 4-Pin, Single row |
| 40 | P3 | 1 | Samtec | TSW-105-06-L-S | Header, 5-Pin, Single row |
| 41 | P4 | 1 | Samtec | SLW-105-01-L-S | |
| 42 | Q1, Q2, Q3, Q4, Q5 | 5 | International Rectifier | IRLMI.2502TRPBI | MOSFET N-CH 20 V 4.2 A SOT-23 |
| 43 | Q6 | 1 | Fairchild Semiconductor | MMBT3904 | TRANSISTOR GP NPN AMP SOT-23 |
| 44 | R1, R12, R24, R29, R30, R31, R32, R54, R63, R64, R65, R66, R67, R68, R69 | 15 | Bourns | ERJ-8ENF4990V | RES 499 OHM 1/4 W 1% 1206 SMD |
| 45 | R2 | 1 | Panasonic | ERJ-M1WSF20MU | RES 0.02 OHM 1 W 1% 2512 SMD |
| 46 | R3 | 1 | Bourns | CRM1206-FZ-R050ELF | RES 0.05 OHM 1/2 W 1% 1206 SMD |

-continued

| Line Item | Designator | Quantity | Manufacturer | Part Number | Description |
|---|---|---|---|---|---|
| 47 | R4, R5, R9, R10, R15, R16, R19, R20, R22, R23 | 10 | Bourns | CRA2512-FZ-R100ELF | RES 0.1 OHM 3 W 1% 2512 SMD |
| 48 | R6 | 1 | Panasonic | ERJ-3EKF5102V | RES 51K OHM 1/10 W 1% 0603 SMD |
| 49 | R7, R8, R13, R14, R18 | 5 | Stackpole Electronics | CSRN2512FKR680 | RES 0.68 OHM 2 W 1% 2512 |
| 50 | R11 | 1 | Panasonic | ERJ-3EKF10R0V | RES 10 OHM 1/10 W 1% 0603 SMD |
| 51 | R17 | 1 | Panasonic | ERJ-14NF40R2U | RES 40.2 OHM 1/2 W 1% 1210 SMD |
| 52 | R21 | 1 | Panasonic | ERJ-3EKF1502V | RES 15K OHM 1/10 W 1% 0603 SMD |
| 53 | R25, R44, R45, R46 | 4 | Panasonic | ERJ-3EKF1001V | RES 1K OHM 1/10 W 1% 0603 SMD |
| 54 | R26 | 1 | Panasonic | ERJ-3EKF2001V | RES 2K OHM 1/10 W 1% 0603 SMD |
| 55 | R27 | 1 | Panasonic | ERJ-3EKF1003V | RES 100K OHM 1/10 W 1% 0603 SMD |
| 56 | R28, R40, R41, R42, R43, R47, R48, R49, R50 | 9 | Panasonic | ERJ-3EKF1002V | RES 10K OHM 1/10 W 1% 0603 SMD |
| 57 | R33, R37, R38, R39 | 4 | Panasonic | ERJ-3EKF1000V | RES 100 OHM 1/10 W 1% 0603 SMD |
| 58 | R51 | 1 | Panasonic | ERJ-2RKF270IX | RES 2.7K OHM 1/10W 1% 0603 SMD |
| 59 | R52 | 1 | Panasonic | ERJ-8ENF6043V | RES 604K OHM 1/4 W 1% 1206 SMD |
| 60 | R53 | 1 | Panasonic | ERJ-3EKF2803V | RES 280K OHM 1/10 W 1% 0402 SMD |
| 61 | R55, R56, R57, R58 | 4 | Panasonic | ERJ-3EKF4702V | RES 47K OHM 1/10 W 1% 0603 SMD |
| 62 | R59 | 1 | Panasonic | ERJ-2GEJ105X | RES 1M OHM 1/10 W 1% 0603 SMD |
| 63 | R60 | 1 | Panasonic | ERJ-2RKF22R0X | RES 22 OHM 1/10 W 1% 0402 SMD |
| 64 | R61 | 1 | Panasonic | ERJ-2RKF5602X | RES 56K OHM 1/10 W 1% 0402 SMD |
| 65 | R62 | 1 | Panasonic | ERJ-2GEJ332X | RES 3.3K OHM 1/10 W 1% 0402 SMD |
| 66 | S1, S2, S3 | 3 | C&K Components | KSC641GLFS | SWITCH TACTILE SPST-NO 0.05 A 32 V |
| 67 | U1 | 1 | International Rectifier | IRF8714PbF | MOSFET N-CH 30 V 13.8 A 8-SOIC |
| 68 | U2 | 1 | Linear Tech | LT43561S-1#PBF | IC OVERVOLT PROT REG 16-SOIC |
| 69 | U3 | 1 | Microchip | MCP1525T-I/TT | IC VREF SERIES PREC 2.5 V SOT23-3 |
| 70 | U4 | 1 | International Rectifier | IRF7406TRPBF | MOSFET P-CH 30 V 5.8 A 8-SOIC |
| 71 | U5 | 1 | Texas Instruments | INA199A1DCK | IC OPAMP CURR SENSE 14 KHZ SC70-6 |
| 72 | U6 | 1 | Vishay Siliconix | SI1869DH-T1-E3 | IC LOAD SW LVL SHIFT 20 V SC70-6 |
| 73 | U7 | 1 | Avago Technologies US | MGA-68563-TR1G | IC AMP LNA MMIC GAAS SMD SOT-363 |
| 74 | U8 | 1 | Linx Technologies | TXM-916-ES | TRANSMITTER RF 916 MHZ 10PIN SMD |
| 75 | U9 | 1 | Microchip | MCP1826S-3002E/DB | IC REG LDO 3 V 1 A SOT223-3 |
| 76 | U10 | 1 | Microchip Technology | PIC24FJ64GA004-I/PT | IC MCU 16 BIT 64 KB FLASH 44TQFP |
| 77 | U11, U13, U15 | 3 | Texas Instruments | SN74LVC2T45DCT | IC BUS TRANSCVR 2BIT N-INV SM8 |
| 78 | U12 | 1 | MICROCHIP | 23K256-I/ST | IC SRAM 256 KBIT 20 MHZ 8TSSOP |
| 79 | U14 | 1 | Microchip Technology | MCP6041T-E/OT | IC OPAMP GP 14 KHZ RRO SOT23-5 |
| 80 | U16 | 1 | Texas Instruments | CC1110F32RHHR | IC SOC RF TXRX W/805 1 MCU 36-VQF |
| 81 | U17 | 1 | TriQuint Semiconductor | 856327 | Signal Condition ing 915/26 MHz Filter |

-continued

| Line Item | Designator | Quantity | Manufacturer | Part Number | Description |
|---|---|---|---|---|---|
| 82 | U18 | 1 | Texas Instruments | CC1190RGVT | RF Front Fnd 850-950 MHz |
| 83 | U101 | 1 | Texas Instruments | SN74LVC1G332DCKR | 1C GATK OR 1CH 3-1NP SC-70-6 |
| 84 | U102 | 1 | Texas Instruments | SN74LVC1G11DCKR | 1C GATE AND 1CH 3-INP SC-70-6 |
| 85 | Y1 | 1 | TXC CORPORATION | AX-12.288MAGV-T | CRYSTAL 12.288MHZ8PF SMD |
| 86 | Y2, Y4 | 2 | Abracon Corporation | ABS06-32.768KHZ-T | CRYSTAL 32.768 KHZ 12.5PF SMD |
| 87 | Y3 | 1 | CTS-Frequency Controls | 403C11A26M00000 | CRYSTAL 26 MHZ 10PF SMD |

FIG. 29 is an exploded view of the miner apparatus 450, and specifically the TPL. The housing 12 encases the tracking portion 310 that carries the circuitry shown in FIGS. 25-28, which includes the CIM 72. There is the proximity device 402 which is a standard proximity device 402 that is currently available and exists in the proximity device sold by Strata Products Worldwide, LLC. There is the battery 14 and circuitry 602 through which the battery and the tracking portion 310 and the proximity detector 402 is connected to the terminals 600 in the housing 12. There is a data port cover 606 that covers over a port to which the software operations can be reprogrammed if necessary in the apparatus 450. There is also a cover plate 612 that covers the terminals 600 on the outside of the housing 12. In the cover 612, there is a wiring port 604 through which the wiring from the terminals 600 extend to the cap lamp 400 to power and trigger the components of the cap lamp 400.

Figure 30:
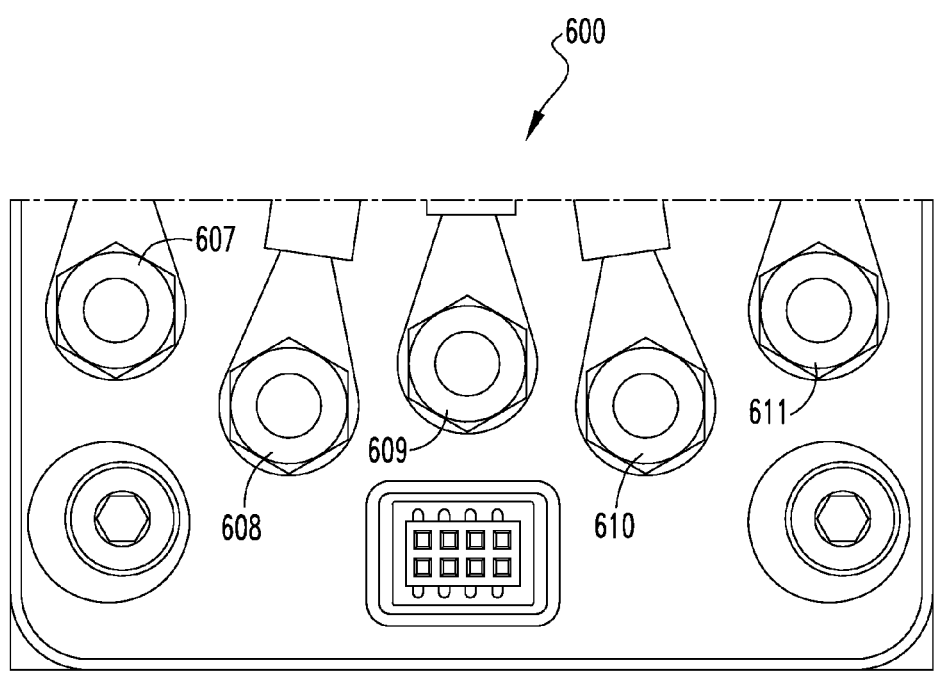
FIG. 30 shows the terminals of the miner apparatus.

FIG. 30 is a close-up view of the terminals 600. Wiring from terminal 607 extends to power the light in the cap lamp 400. Wiring from the terminal 608 extends to the battery 14 to receive power from the battery 14. Wiring from terminal 609 extends to an LED in the cap lamp 400 to power the LED. Wiring from the terminal 610 extends to a sounder in the cap lamp 400 that makes a noise to alert the miner when they have come to close to a proximity detector 404 and a warning or a hazard state is triggered. Terminal 611 receives wiring from the cap lamp 400 and provides a ground or a return from the cap lamp 400.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. A communication system in a mine comprising:
a remote station;
a data network in the mine on which solely data is sent throughout the mine to the remote station;
a wireless network in the mine on which voice and data is sent bidirectionally throughout the mine to the remote station separate and independent from the data network to the remote station; and
a plurality of nodes distributed and apart from each other that form the data network and the wireless network, each node having a data portion which receives and sends data on the data network, a wireless portion which receives and sends voice signals on the wireless network, and a power supply portion in electrical communication with the data portion and the wireless portion which powers the data portion and the wireless portion, at least a first node of the plurality of nodes receiving power from another node of the plurality of nodes, the first node in electrical connection with the another node, the remote station monitoring the nodes.

2. The system of claim 1 wherein data on the data network includes tracking information of an individual.

3. The system of claim 2 wherein the data on the data network is sent and received at least one node of the plurality of nodes and the data network is bidirectional.

4. The system of claim 3 wherein the data from the data network is sent on the data network and the wireless network.

5. The system of claim 4 wherein each node includes a data converter in communication with the data portion and the wireless portion which converts the data from the data network into a transmission signal that is transmitted on the wireless network.

6. A communication node of a data network and a wireless network in a mine comprising;
a housing;
a data portion disposed in the housing which receives data on the data network in the mine, the data network in the mine on which solely data is sent throughout the mine to a remote station which monitors nodes in the mine;
a wireless portion disposed in the housing which receives and sends voice signals on the wireless network in the mine, the wireless network in the mine on which voice and data is sent bidirectionally throughout the mine to the remote station separate and independent from the data network to the remote station;
a power supply portion disposed in the housing in electrical communication with the data portion and the wireless portion which powers the data portion and the wireless portion the power supply portion having a power port which receives power from another node; and
a data converter disposed in the housing in communication with the data portion and the wireless portion which converts the data from the data network into a transmission signal that is transmitted on the wireless network.

7. The node of claim 6 wherein the wireless portion includes a first radio disposed in the housing to transmit the transmission signal.

8. The node of claim 7 wherein the wireless portion includes a switch disposed in the housing in communication with the first radio and the data converter.

9. The node of claim 8 wherein the wireless portion includes an external fiber connector in communication with the switch to connect with an external fiber to transmit the transmission signal.

10. A method for communicating in a mine comprising the steps of:
- receiving data wirelessly at a data portion of a first node of a plurality of nodes in the mine from a data network on which solely data is sent throughout the mine and to a remote station which monitors the nodes, the plurality of nodes distributed and apart from each other and form the data network and a wireless network separate and independent from the data network through which voice and data are sent throughout the mine to the remote station bidirectionally separate and independent from the data network to the remote station;
- converting with a data converter in communication with the data portion the data from the data network into a transmission signal that is transmitted on the wireless network, the wireless network transmitting and receiving voice and data bidirectionally;
- transmitting the transmission signal from the first node on the wireless network with a wireless portion of the first node; and
- powering the data portion and the data portion with a power supply portion in electrical communication with the data portion and the wireless portion, at least a first node of the plurality of nodes receiving power from another node of the plurality of nodes, the first node in electrical connection with the another node.

* * * * *